(12) United States Patent
Burns et al.

(10) Patent No.: US 7,432,302 B2
(45) Date of Patent: Oct. 7, 2008

(54) COMPOSITION CONTAINING POLYAMINE TRANSPORT INHIBITOR AND USE THEREOF

(75) Inventors: Mark R. Burns, Kenmore, WA (US); Gerard F. Graminski, Madison, CT (US); Nand Baindur, Kendall Park, NJ (US); Reitha S. Weeks, Seattle, WA (US)

(73) Assignee: MediQuest Therapeutics, Inc., Bothell, WA (US)

( * ) Notice: Subject to any disclaimer, the term of this patent is extended or adjusted under 35 U.S.C. 154(b) by 223 days.

(21) Appl. No.: 11/062,481

(22) Filed: Feb. 23, 2005

(65) Prior Publication Data

US 2005/0245615 A1    Nov. 3, 2005

Related U.S. Application Data

(63) Continuation-in-part of application No. 10/296,259, filed as application No. PCT/US02/00347 on Jan. 8, 2002, now Pat. No. 6,963,010.

(60) Provisional application No. 60/260,415, filed on Jan. 8, 2001.

(51) Int. Cl.
*A61K 31/65* (2006.01)

(52) U.S. Cl. .............. 514/616; 514/623; 514/624; 514/625; 514/626; 514/629

(58) Field of Classification Search ............ 514/461, 514/601, 602, 603, 605, 616, 623, 62, 624, 514/625, 626, 629; 549/487, 488; 564/84, 564/86, 98, 152, 155, 198
See application file for complete search history.

(56) References Cited

U.S. PATENT DOCUMENTS

| | | | |
|---|---|---|---|
| 5,541,230 A | | 7/1996 | Basu et al. |
| 5,648,394 A | * | 7/1997 | Boxall et al. ............ 514/567 |
| 5,654,287 A | | 8/1997 | Prakash et al. |
| 6,172,261 B1 | | 1/2001 | Vermeulin et al. |
| 6,235,737 B1 | * | 5/2001 | Styczynski et al. ....... 514/237.8 |
| 6,963,010 B2 | * | 11/2005 | Burns et al. ............. 564/152 |

FOREIGN PATENT DOCUMENTS

| | | |
|---|---|---|
| WO | WO-91/00853 A1 | 1/1991 |
| WO | WO-97/33560 | 9/1997 |
| WO | WO-99/03823 A2 | 1/1999 |
| WO | WO-00/46187 A2 | 8/2000 |

OTHER PUBLICATIONS

Golub, Science, vol. 286, 1999, pp. 531-537.*
Huff, J. Med. Chem., 34(8), 2305-14, 1991.*

* cited by examiner

*Primary Examiner*—Shailendra Kumar
(74) *Attorney, Agent, or Firm*—Connolly Bove Lodge & Hutz LLP

(57) ABSTRACT

Proliferative cutaneous disease states or conditions are treated by administering a polyamine transport inhibitor R-X-L-polyamine wherein R is a straight or branched C10-50 saturated or unsaturated aliphatic, carboxyalkyl, carbalkoxyalkyl, or alkoxy; a C1-8 alicyclic; a single or multiring aryl substituted or unsubstituted aliphatic; and aliphatic-substituted or unsubstituted single or multiring aromatic; a single or multiring heterocyclic; a single or multiring heterocyclic aliphatic; an aryl sulfonyl;

X is —CO—, —$SO_2$—, or —$CH_2$—; and

L is a covalent bond or a naturally occurring amino acid, lysine, ornithine, 2,4-diaminobutyric acid, or pharmaceutically acceptable salts thereof or prodrug thereof, and a polyamine biosynthesis inhibitor.

9 Claims, 23 Drawing Sheets

| 7 | 8 | 9 | 10 | 11 | 12 | 13 | 14 | 15 |
|---|---|---|---|---|---|---|---|---|
| (structure 6) | (structure 5) | (structure 4) | (structure 2) | (structure 1) | (structure 2) | (structure 3) | (structure 4) | (structure) |
| IA7 | IA8 | IA9 | IA10 | IA11 | IA12 | IA13 | IA14 | IA15 |
| IB7 | IB8 | IB9 | IB10 | IB11 | IB12 | IB13 | IB14 | IB15 |
| IC7 | IC8 | IC9 | IC10 | IC11 | IC12 | IC13 | IC14 | IC15 |
| ID7 | ID8 | ID9 | ID10 | ID11 | ID12 | ID13 | ID14 | ID15 |
| IE7 | IE8 | IE9 | IE10 | IE11 | IE12 | IE13 | IE14 | IE15 |
| IF7 | IF8 | IF9 | IF10 | IF11 | IF12 | IF13 | IF14 | IF15 |

FIG. 2B

| | IA16 | IB16 | IC16 | ID16 | IE16 | IF16 |
|---|---|---|---|---|---|---|
| 16 | | | | | | |
| 17 | IA17 | IB17 | IC17 | ID17 | IE17 | IF17 |
| 18 | IA18 | IB18 | IC18 | ID18 | IE18 | IF18 |
| 19 | IA19 | IB19 | IC19 | ID19 | IE19 | IF19 |
| 20 | IA20 | IB20 | IC20 | ID20 | IE20 | IF20 |
| 21 | IA21 | IB21 | IC21 | ID21 | IE21 | IF21 |
| 22 | IA22 | IB22 | IC22 | ID22 | IE22 | IF22 |
| 23 | IA23 | IB23 | IC23 | ID23 | IE23 | IF23 |

FIG. 2C

| | | IA24 | IB24 | IC24 | ID24 | IE24 | IF24 |
|---|---|---|---|---|---|---|---|
| 24 | (benzoyl chloride) | IA24 | IB24 | IC24 | ID24 | IE24 | IF24 |
| 25 | (2-furoyl chloride) | IA25 | IB25 | IC25 | ID25 | IE25 | IF25 |
| 26 | (4-biphenylcarbonyl chloride) | IA26 | IB26 | IC26 | ID26 | IE26 | IF26 |
| 27 | (nicotinoyl chloride) | IA27 | IB27 | IC27 | ID27 | IE27 | IF27 |
| 28 | (4-aminobenzoyl chloride) | IA28 | IB28 | IC28 | ID28 | IE28 | IF28 |
| 29 | (diphenylacetyl chloride) | IA29 | IB29 | IC29 | ID29 | IE29 | IF29 |
| 30 | (1-adamantanecarbonyl chloride) | IA30 | IB30 | IC30 | ID30 | IE30 | IF30 |

FIG. 2D

| | | IA31 | IB31 | IC31 | ID31 | IE31 | IF31 |
|---|---|---|---|---|---|---|---|
| 31 | (adamantyl-C(O)Cl) | IA31 | IB31 | IC31 | ID31 | IE31 | IF31 |
| 32 | (cyclohexyl-C(O)Cl) | IA32 | IB32 | IC32 | ID32 | IE32 | IF32 |
| 33 | ((H₃C)₂CH-C(O)Cl) | IA33 | IB33 | IC33 | ID33 | IE33 | IF33 |
| 34 | ((H₃C)₃C-C(O)Cl) | IA34 | IB34 | IC34 | ID34 | IE34 | IF34 |
| 35 | (H₃C-C(CH₃)-C(O)Cl) | IA35 | IB35 | IC35 | ID35 | IE35 | IF35 |
| 36 | ((H₃C)₂CH-CH₂-C(O)Cl) | IA36 | IB36 | IC36 | ID36 | IE36 | IF36 |
| 37 | (norbornyl-CH₂-C(O)Cl) | IA37 | IB37 | IC37 | ID37 | IE37 | IF37 |
| 38 | (menthyl-O-C(O)Cl) | IA38 | IB38 | IC38 | ID38 | IE38 | IF38 |
| 39 | (F₃CF₂CF₂C(O)Cl) | IA39 | IB39 | IC39 | ID39 | IE39 | IF39 |

FIG. 2E

| SERIES II | A ![structure] A (ε-L-Lys) | B ![structure] B (ε-D-Lys) | C ![structure] C (α-L-Lys) | D ![structure] D (α-L-Lys) | E ![structure] E (α,ε-L-Lys) | F ![structure] F (α, ε-D-Lys) |
|---|---|---|---|---|---|---|
| 1 | CH₃SO₂Cl | IIA1 | IIB1 | IIC1 | IID1 | IIE1 | IIF1 |
| 2 | CH₃CH₂SO₂Cl | IIA2 | IIB2 | IIC2 | IID2 | IIE2 | IIF2 |
| 3 | CH₃(CH₂)₂SO₂Cl | IIA3 | IIB3 | IIC3 | IID3 | IIE3 | IIF3 |
| 4 | CH₃(CH₂)₃SO₂Cl | IIA4 | IIB4 | IIC4 | IID4 | IIE4 | IIF4 |
| 5 | CH₃(CH₂)₄SO₂Cl | IIA5 | IIB5 | IIC5 | IID5 | IIE5 | IIF5 |
| 6 | CH₃(CH₂)₈SO₂Cl | IIA6 | IIB6 | IIC6 | IID6 | IIE6 | IIF6 |
| 7 | CH₃(CH₂)₁₀SO₂Cl | IIA7 | IIB7 | IIC7 | IID7 | IIE7 | IIF7 |
| 8 | CH₃(CH₂)₁₂SO₂Cl | IIA8 | IIB8 | IIC8 | IID8 | IIE8 | IIF8 |
| 9 | CH₃(CH₂)₁₄SO₂Cl | IIA9 | IIB9 | IIC9 | IID9 | IIE9 | IIF9 |
| 10 | CH₃(CH₂)₁₅SO₂Cl | IIA10 | IIB10 | IIC10 | IID10 | IIE10 | IIF10 |
| 11 | CH₃(CH₂)₁₆SO₂Cl | IIA11 | IIB11 | IIC11 | IID11 | IIE11 | IIF11 |
| 12 | CH₃(CH₂)₁₇SO₂Cl | IIA12 | IIB12 | IIC12 | IID12 | IIE12 | IIF12 |
| 13 | CH₃(CH₂)₁₈SO₂Cl | IIA13 | IIB13 | IIC13 | IID13 | IIE13 | IIF13 |
| 14 | CH₃(CH₂)₁₉SO₂Cl | IIA14 | IIB14 | IIC14 | IID14 | IIE14 | IIF14 |
| 15 | CH₃(CH₂)₂₀SO₂Cl | IIA15 | IIB15 | IIC15 | IID15 | IIE15 | IIF15 |

FIG. 2G

|    |           | IIA16 | IIB16 | IIC16 | IID16 | IIE16 | IIF16 |
|----|-----------|-------|-------|-------|-------|-------|-------|
| 16 | (benzenesulfonyl chloride) | IIA16 | IIB16 | IIC16 | IID16 | IIE16 | IIF16 |
| 17 | (mesitylenesulfonyl chloride) | IIA17 | IIB17 | IIC17 | IID17 | IIE17 | IIF17 |
| 18 | (2-naphthalenesulfonyl chloride) | IIA18 | IIB18 | IIC18 | IID18 | IIE18 | IIF18 |
| 19 | (1-naphthalenesulfonyl chloride) | IIA19 | IIB19 | IIC19 | IID19 | IIE19 | IIF19 |
| 20 | (5-dimethylamino-1-naphthalenesulfonyl chloride) | IIA20 | IIB20 | IIC20 | IID20 | IIE20 | IIF20 |
| 21 | (5-(4-chlorobenzamido)thiophene-2-sulfonyl chloride) | IIA21 | IIB21 | IIC21 | IID21 | IIE21 | IIF21 |

FIG. 2H

| | IIIA6 | IIIB6 | IIIC6 | IIID6 | IIIE6 | IIIF6 |
|---|---|---|---|---|---|---|
| 6 | | | | | | |
| 7 | IIIA7 | IIIB7 | IIIC7 | IIID7 | IIIE7 | IIIF7 |

FIG. 2J

| SERIES IV | A A (α-L-Lys) | B B (ε-D-Lys) | C C (α-L-Lys) | D D (α-L-Lys) | E E (α,ε-L-Lys) | F F (α, ε-D-Lys) |
|---|---|---|---|---|---|---|
| 1 ![CH3] | IVA1 | IVB1 | IVC1 | IVD1 | IVE1 | IVF1 |
| 2 ![CH3] | IVA2 | IVB2 | IVC2 | IVD2 | IVE2 | IVF2 |
| 3 ![CH3] | IVA3 | IVB3 | IVC3 | IVD3 | IVE3 | IVF3 |
| 4 ![CH3] | IVA4 | IVB4 | IVC4 | IVD4 | IVE4 | IVF4 |
| 5 ![CH3] | IVA5 | IVB5 | IVC5 | IVD5 | IVE5 | IVF5 |
| 6 ![CH3] | IVA6 | IVB6 | IVC6 | IVD6 | IVE6 | IVF6 |

FIG. 2K

| | | | | | | | |
|---|---|---|---|---|---|---|---|
| 7 | 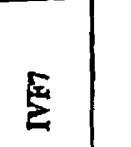 | IVA7 | IVB7 | IVC7 | IVD7 | IVE7 | IVF7 |
| 8 | 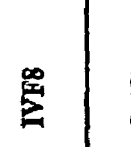 | IVA8 | IVB8 | IVC8 | IVD8 | IVE8 | IVF8 |
| 9 | 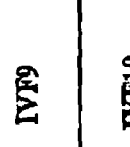 | IVA9 | IVB9 | IVC9 | IVD9 | IVE9 | IVF9 |
| 10 | 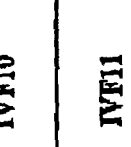 | IVA10 | IVB10 | IVC10 | IVD10 | IVE10 | IVF10 |
| 11 | 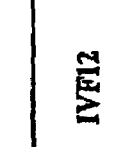 | IVA11 | IVB11 | IVC11 | IVD11 | IVE11 | IVF11 |
| 12 |  | IVA12 | IVB12 | IVC12 | IVD12 | IVE12 | IVF12 |
| 13 | 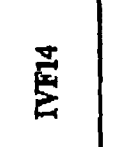 | IVA13 | IVB13 | IVC13 | IVD13 | IVE13 | IVF13 |
| 14 |  | IVA14 | IVB14 | IVC14 | IVD14 | IVE14 | IVF14 |
| 15 |  | IVA15 | IVB15 | IVC15 | IVD15 | IVE15 | IVF15 |
FIG. 2L

| 16 | | IVA16 | IVB16 | IVC16 | IVD16 | IVE16 | IVF16 |
|---|---|---|---|---|---|---|---|
| 17 | | IVA17 | IVB17 | IVC17 | IVD17 | IVE17 | IVF17 |
| 18 | | IVA18 | IVB18 | IVC18 | IVD18 | IVE18 | IVF18 |
| 19 | | IVA19 | IVB19 | IVC19 | IVD19 | IVE19 | IVF19 |
| 20 | | IVA20 | IVB20 | IVC20 | IVD20 | IVE20 | IVF20 |
| 21 | | IVA21 | IVB21 | IVC21 | IVD21 | IVE21 | IVF21 |
| 22 | | IVA22 | IVB22 | IVC22 | IVD22 | IVE22 | IVF22 |
| 23 | | IVA23 | IVB23 | IVC23 | IVD23 | IVE23 | IVF23 |

FIG. 2M

| | | | | | | | |
|---|---|---|---|---|---|---|---|
| 24 | 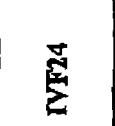 | IVA24 | IVB24 | IVC24 | IVD24 | IVE24 | IVF24 |
| 25 | 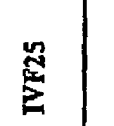 | IVA25 | IVB25 | IVC25 | IVD25 | IVE25 | IVF25 |
| 26 | 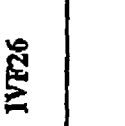 | IVA26 | IVB26 | IVC26 | IVD26 | IVE26 | IVF26 |
| 27 | 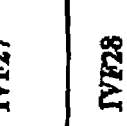 | IVA27 | IVB27 | IVC27 | IVD27 | IVE27 | IVF27 |
| 28 | 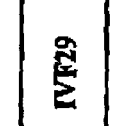 | IVA28 | IVB28 | IVC28 | IVD28 | IVE28 | IVF28 |
| 29 |  | IVA29 | IVB29 | IVC29 | IVD29 | IVE29 | IVF29 |
| 30 |  | IVA30 | IVB30 | IVC30 | IVD30 | IVE30 | IVF30 |
| 31 |  | IVA31 | IVB31 | IVC31 | IVD31 | IVE31 | IVF31 |
FIG. 2N

| | | | | | | |
|---|---|---|---|---|---|---|
| 32 | [3-phenylbenzaldehyde] | IVA32 | IVB32 | IVC32 | IVD32 | IVE32 | IVF32 |
| 33 | [4-phenylbenzaldehyde] | IVA33 | IVB33 | IVC33 | IVD33 | IVE33 | IVF33 |
| 34 | [3-bromobenzaldehyde] | IVA34 | IVB34 | IVC34 | IVD34 | IVE34 | IVF34 |
| 35 | CH$_2$O | IVA35 | IVB35 | IVC35 | IVD35 | IVE35 | IVF35 |

FIG. 20

| SERIES V | | A <br> (ε-L-Lys) | B <br> (ε-D-Lys) | C <br> (α-L-Lys) | D <br> (α-L-Lys) | E <br> (α,ε-L-Lys) | F <br> (ε,α-D-Lys) |
|---|---|---|---|---|---|---|---|
| 1 | | VA1 | VB1 | VC1 | VD1 | VE1 | VF1 |
| 2 | | VA2 | VB2 | VC2 | VD2 | VE2 | VF2 |
| 3 | | VA3 | VB3 | VC3 | VD3 | VE3 | VF3 |
| 4 | | VA4 | VB4 | VC4 | VD4 | VE4 | VF4 |
| 5 | | VA5 | VB5 | VC5 | VD5 | VE5 | VF5 |
| 6 | | VA6 | VB6 | VC6 | VD6 | VE6 | VF6 |
| 7 | | VA7 | VB7 | VC7 | VD7 | VE7 | VF7 |

FIG. 2P

| | VA | VB | VC | VD | VE | VF |
|---|---|---|---|---|---|---|
| 8  H₃C-C(O)-...CH₃/10  | VA8  | VB8  | VC8  | VD8  | VE8  | VF8  |
| 9  H₃C-C(O)-...CH₃/12  | VA9  | VB9  | VC9  | VD9  | VE9  | VF9  |
| 10 H₃C-C(O)-...CH₃/13  | VA10 | VB10 | VC10 | VD10 | VE10 | VF10 |
| 11 H₃C-C(O)-...CH₃/14  | VA11 | VB11 | VC11 | VD11 | VE11 | VF11 |
| 12 H₃C-C(O)-...CH₃/15  | VA12 | VB12 | VC12 | VD12 | VE12 | VF12 |
| 13 H₃C-C(O)-...CH₃/16  | VA13 | VB13 | VC13 | VD13 | VE13 | VF13 |
| 14 H₃C-C(O)-...CH₃/17  | VA14 | VB14 | VC14 | VD14 | VE14 | VF14 |
| 15 H₃C-C(O)-...CH₃/18  | VA15 | VB15 | VC15 | VD15 | VE15 | VF15 |
| 16 H₃C-C(O)-...CH₃/20  | VA16 | VB16 | VC16 | VD16 | VE16 | VF16 |

FIG. 2Q

| | | VA | VB | VC | VD | VE | VF |
|---|---|---|---|---|---|---|---|
| 17 | 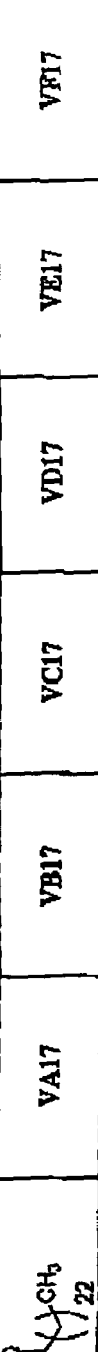 | VA17 | VB17 | VC17 | VD17 | VE17 | VF17 |
| 18 | 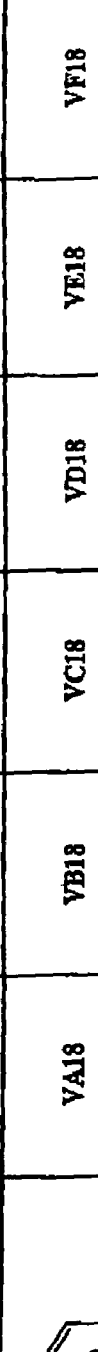 | VA18 | VB18 | VC18 | VD18 | VE18 | VF18 |
| 19 |  | VA19 | VB19 | VC19 | VD19 | VE19 | VF19 |
| 20 |  | VA20 | VB20 | VC20 | VD20 | VE20 | VF20 |
| 21 |  | VA21 | VB21 | VC21 | VD21 | VE21 | VF21 |
| 22 |  | VA22 | VB22 | VC22 | VD22 | VE22 | VF22 |
| 23 | 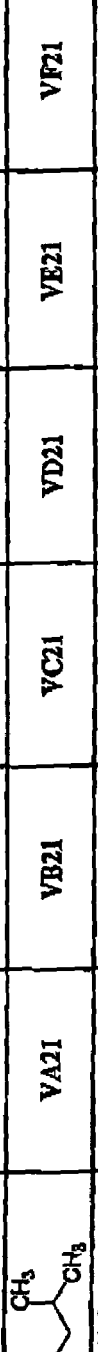 | VA23 | VB23 | VC23 | VD23 | VE23 | VF23 |
| 24 | 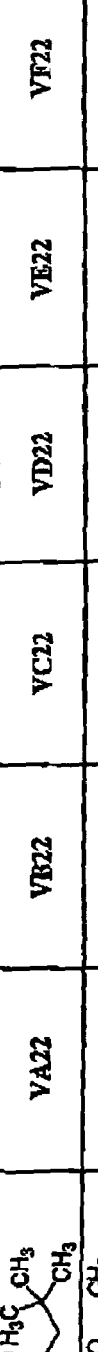 | VA24 | VB24 | VC24 | VD24 | VE24 | VF24 |
FIG. 2R

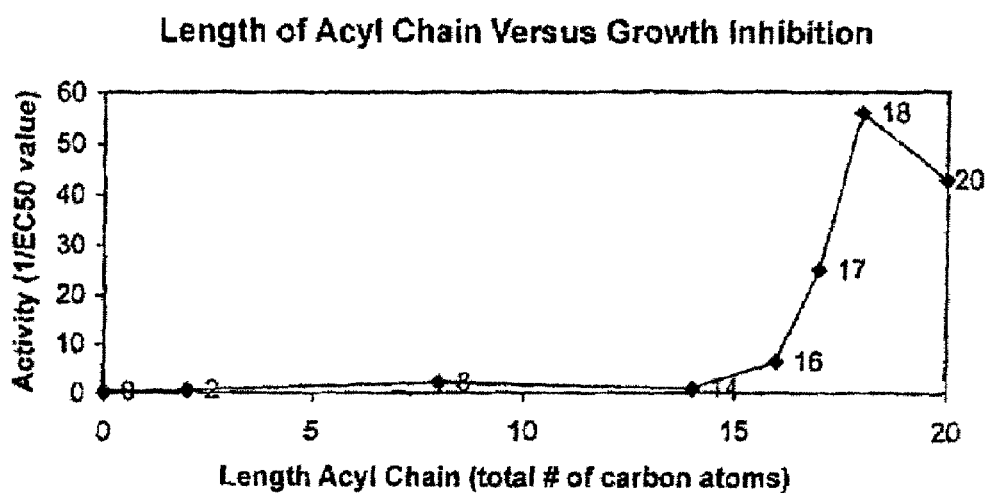
FIG. 4
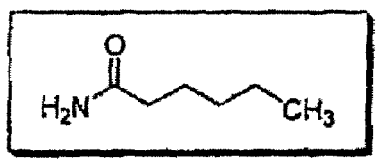
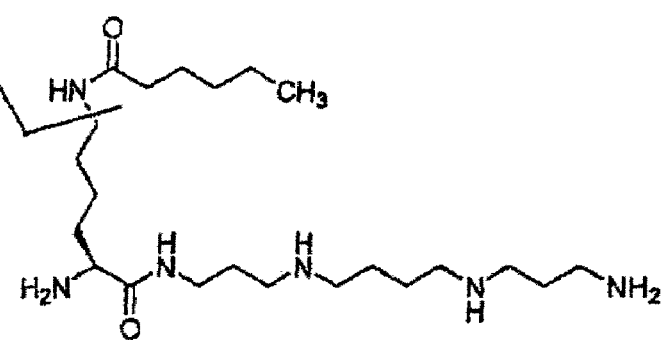
IA9 As an Example
FIG. 5

COMPOSITION CONTAINING POLYAMINE TRANSPORT INHIBITOR AND USE THEREOF

CROSS REFERENCE TO RELATED APPLICATIONS

This application is a continuation-in-part of application U.S. Ser. No. 10/296,259 entitled "Hydrophobic Polyamine Analogs and Methods for Their Use" now U.S. Pat. No. 6,963,010, which is a 371 national stage of PCT/US02/00347, entitled "Hydrophobic Polyamine Analogs and Methods for Their Use," filed Jan. 8, 2002, which in turn claims priority from U.S. Ser. No. 60/260,415, entitled "Hydrophobic Polyamine Analogs and Methods for Their Use," filed Jan. 8, 2001 and now abandoned; the entire disclosures of which are incorporated herein by reference.

TECHNICAL FIELD

This disclosure in the field of skin biology and biological chemistry relates to the combination use of a polyamine transport inhibitor together with a polyamine biosynthesis inhibitor to potently deplete skin cells of polyamines and is thus useful for treating proliferative cutaneous disease states or conditions. These disease states are characterized by higher than normal cellular growth rate that is dependant upon an abundant supply of polyamines.

BACKGROUND

Decades of research on the myriad of biological activities that the polyamines, putrescine, spermidine and spermine play in cellular processes have shown the profound role they play in life (Cohen, S. S., "A Guide to the Polyamines" 1998, Oxford University Press, New York). As polycations at physiological pH, they bind tightly to and strongly modulate the biological activities of all of the anioinic cellular components.

Many stimuli involved in both normal and neoplastic growth activate the polyamine biosynthetic pathway. A great number of multidisciplinary studies have shown that the intracellular concentrations of the polyamines is highly regulated at many steps in their biosynthesis, catabolism and transport. The fact that cells contain such complex apparatus for the tight control of the levels of these molecules shows that only a very narrow concentration range is tolerated.

Polyamine transport into mammalian cells is energy and temperature dependent, saturable, carrier-mediated and operates against a substantial concentration gradient (Seiler, N. et al. Polyamine transport in mammalian cells. *Int. J. Biochem.* 1990, 22, 211-218; Khan, N. A.; Quemener, V. et al. Characterization of polyamine transport pathways, in *Neuropharmacology of Polyamines* (Carter, C., ed)., 1994, Academic, San Diego, pp. 37-60). Ample experimental evidence exists that polyamine concentration homeostasis is mediated via this transport system. Changes in the requirements for polyamines in response to growth stimulation is reflected by increases in the transport activity. Stimulation of human fibroblasts to cell proliferation by serum or epidermal growth factor was followed by an 18-100 fold increase in the uptake of putrescine (Dipasquale, A. et al. Epidermal growth factor stimulates putrescine transport and ornithine decarboxylase activity in cultures human fibroblasts. *Exp. Cell Res.* 1978, 116, 317-323; Pohjanpelto, P. Putrescine transport is greatly increased in human fibroblasts initiated to proliferate. *J. Cell Biol.* 1976, 68, 512-520). Tumors have been shown to have an increased rate of putrescine uptake (Volkow, N. et al. Labeled putrescine as a probe in brain tumors. *Science*, 1983, 221, 673-675; Moulinoux, J-P. et al. Biological significance of circulating polyamines in oncology. *Cell. Mol. Biol.* 1991, 37, 773-783).

Inhibition of polyamine biosynthesis in cells in culture by α-difluoromethylornithine (DFMO), a well-studied mechanism-based inhibitor of ODC, causes a substantial depletion of intracellular putrescine and spermidine with resultant cell growth inhibition. Upon supplementing the culture media with exogenous polyamines this depletion causes transport activity to rise several-fold (Bogle, R. G. et al. Endothelial polyamine uptake: selective stimulation by L-arginine deprivation or polyamine depletion. *Am. J. Physiol.* 1994, 266, C776-C783; Alhonen-Hongisto, L. et al. Intracellular putrescine deprivation induces uptake of the natural polyamines and methylglyoxal bis(guanylhydrozone). *Biochem. J.* 1980, 192, 941-945). The cells then returned to their original rate of growth.

Genes for the polyamine transport protein or complex have been cloned from *Escherichia coli* and yeast (Kashiwagi, K. et al. *J. Biol. Chem.* 1990, 265, 20893-20897; Tomitori, H. et al. Identification of a gene for a polyamine transport protein in yeast. *J. Biol. Chem.* 1999, 274, 3265-3267). The genes for the mammalian transporter await identification. A subunit of the transporter from *E. coli* has been crystallized and its X-ray structure has been determined (Sugiyama, S. et al. Crystal structure of PotD, the primary receptor of the polyamine transport system in *Escherichia Coli. J. Biol. Chem.* 1996, 271, 9519-9525). This structure represents one of a few but growing number solved for spermidine-binding proteins. Since this structure was determined on a prokaryotic species its use in the design of mammalian transport inhibitors was deemed to be of limited value.

Several researchers have studied the ability of polyamine analogs to inhibit the uptake of 3H-spermidine into cells. Bergeron and coworkers studied the effect of addition of different alkyl group substitutions on the terminal nitrogen atoms of spermidine or spermine analogs (Bergeron, R. J. et al. Antiproliferative properties of polyamine analogs: a structure-activity study. *J. Med. Chem.* 1994, 37, 3464-3476). They showed that larger alkyl groups diminished the ability to prevent uptake of radiolabeled spermidine. They later concluded that increases in the number of methylenes between the nitrogen atoms decreased the ability to compete for 3H spermidine uptake (Bergeron, R. J. et al. A comparison of structure-activity relationships between spermidine and spermine antineoplastics. *J. Med. Chem.* 1997, 40, 1475-1494). They also concluded that the polyamine transport apparatus requires only three cationic centers for polyamine recognition and transport (Porter, C. W. et al. *J. Cancer Res.* 1984, 44, 126-128). Two groups have analyzed literature examples of the polyamine analogs' ability to inhibit 3H spermidine uptake into L1210 cells by CoMFA and QSAR methods (Li, Y. et al. Comparative molecular field analysis-based predictive model of structure-function relationships of polyamine transport inhibitors in L1210 cells. *Cancer Res.* 1997, 57, 234-239; Xia, C. Q. et al. QSAR analysis of polyamine transport inhibitors in L1210 cells. *J. Drug Target.* 1998, 6, 65-77).

A radiochemical assay is used for biochemical analysis of transport and has been used to study polyamine transport in yeast and a variety of mammalian cells (Kakinuma, Y. et al., *Biochem. Biophys. Res. Comm.* 216:985-992, 1995; Seiler, N. et al, *Int. J. Biochem. Cell Biol.* 28:843-861, 1996). See, for example Huber, M. et al. *Cancer Res.* 55:934-943, 1995.

Many undesirable skin conditions are defined by uncharacteristically proliferative cell growth of the underlying tissue. Clinical conditions range into various broad classes from the extremely fast growth and life-threatening malignant cancerous disease states to immunological disease states such as cutaneous lupus, atopic dermatitis and psoriasis. The inhibition of unwanted hair growth, although not a life-threatening disease state, is nevertheless a very important cosmetic problem. Any therapeutic or treatment that could reduce that growth of the skin tissue or hair would be useful in these conditions.

Mammalian hair growth is cyclic and is composed of anagen (hair growth), catagen (follicle regression) and telogen (resting) phases. In mice, ornithine decarboxylate (ODC) is expressed in ectodermal cells at sites where hair follicles develop during embryonic development (Nancarrow, M. J., et al., *Mech. Dev.* 84: 161-164 (1999); Schweier, J. In: *Molecular Biology of the Skin: The Keratinocyte*, Darmon M, et al., Eds., Academic Press, New York, 1993, pp 33-78).

In proliferating bulb cells of anagen follicles, ODC is abundantly expressed except for a pocket of cells at its base. It has been hypothesized that local mediators such as fibroblast growth factors or BMPs induce the expression of ODC in a transitory fashion resulting in the hair follicle to enter the anagen phase of growth (Soler, et al., Modulation of murine hair follicle function by alterations in ornithine decarboxylase activity. *J. Invest. Dermatol.* 1996, 106 (5), 1108-1113).

After the local concentration of these growth factors decline, ODC activity is also reduced allowing the follicles to enter catagen phase. ODC protein expression does not resume until new follicle growth cycle commences. A more complex expression of ODC is found in vibrissae (beard hair). ODC is expressed in the keratinocytes of the vibrissal hair shaft as well as in the bulb and outer root sheath cells near the follicle bulge. In comparison, ODC expression is very low in interfollicular epidermis. For a review of the biology of hair growth control, see Messenger, A. G. The control of hair growth: an overview. *J. Invest. Dermatol.*, 1993, 101(1), 4S-9S. The polyamine concentrations in normal human epidermis have been measured. (El Baze et al., Distribution of polyamines in human epidermas. *British J. Dermatology* 1985, 112, 393-396).

It has been shown that polyamine levels, together with the levels of their biosynthetic enzymatic activities are elevated in proliferative states. (Cohen, S. S. A Guide to the polyamines, Oxford University Press, 1998, New York).

The first, dedicated and rate-limiting step in polyamine biosynthesis is the well-examined enzyme ornithine decarboxylase (ODC). Elevated levels of this enzyme in a variety of proliferating tissue types has led to the designation of its gene as a protooncogene. (Auvinen et al., Ornithine decarboxylase activity is critical for cell transformation. *Nature,* 1992, 360, 355-358). Despite its consistent appearance in transformed tissues, its overexpression is not in itself sufficient for tumor formation. (Clifford, A et al., *Cancer Res.* 1995, 55, 1680-1686).

An initiation event, either chemical or physical, appears to be required for transformation to occur. An example of a physical initiation event and the resulting increase in levels of skin polyamines can be found in the work of Seiler and Knodgen. (Seiler et al., Effects of ultraviolet light on epidermal polyamine metabolism. *Biochemical Med.,* 1979, 21, 168-181). Following a 10 minute UV exposure, the concentrations of skin polyamines, putrescine and spermidine, were shown to be elevated by 5-fold and 2-fold respectively.

O'Brien and coworkers explored the effect of a variety of chemical inducing agents including 12-O-tetradecanoyl-phorbol-13-acetate (TPA) on the skin levels of ODC activity. (O'Brien et al., Induction of the polyamine-biosynthetic enzymes in mouse epidermis by tumor-promoting agents. *Cancer Res.* 1975, 35(7), 1662-70). The activity reached a peak (230-fold greater than control) at 4 to 5 hr after TPA treatment and returned to control level by 12 hr. Numerous other studies showed that treatment of skin with chemical or physically insults results in an increase in the enzymatic activity of ODC with a corresponding increase in the levels of the polyamines. (Scalabrino et al., Levels of activity of the polyamine biosynthetic decarboxylases as indicators of degree of malignancy of human cutaneous epitheliomas. *J. Invest Dermatol.* 1980, 74(3), 122-4; O'Brien T G. The induction of ornithine decarboxylase as an early, possibly obligatory, event in mouse skin carcinogenesis. *Cancer Res.* 1976, 36(7 PT 2), 2644-53; Young et al., UV wavelength dependence for the induction of ornithine decarboxylate activity in hairless mouse epidermis. *Carcinogenesis,* 1986, 7(4), 601-604).

It has been hypothesized that increases in ODC activity associated with skin is almost entirely due to high cellular turnover time of hair follicles (18-23 h) and hence a reflection of their highly proliferative state. (Hynd, P. I. et al., Inhibition of polyamine synthesis alters hair follicle function and fiber composition. *J. Invest. Dermtol.* 1996, 106(2), 249-253).

In a study by Hynd and coworkers, sheep were treated systemically with DFMO and minimal effects on fiber growth (10% decline), fiber diameter (14% increase) and sulfur content (increased) of hair were measured. Detailed experiments into the effects of DFMO treatment on the protein composition of fibers and levels of keratin gene mRNA were performed in an attempt to explain the unexpected lack of effects on growth. These authors also used a cultured follicle fiber growth assay to explore other treatment options. The inclusion of 500 µM DFMO, a well studied inhibitor of ODC, to the culture media had no effect on the growth of cultured follicles, paralleling the result on the animal. It was found that treatment with the AdoMet decarboxylase inhibitor MGBG caused potent ($ED_{50}$~5 µM) inhibition of the growth of cultured follicles. This growth inhibition was paralleled by the effects of MGBG on DNA synthesis as measured by a tritiated thymidine incorporation assay.

An experiment in strong support of the requirement of spermidine for hair growth was the addition of spermidine (50 µM) to the MGBG (10 mM) treated cultured hair follicles. Complete recovery of DNA synthesis was observed. Addition of spermine (50 µM) did not overcome the MGBG-mediated inhibition. This would seem to suggest the important role played by spermidine in hair growth. Furthermore, the use of a specific spermine synthase inhibitor (N-butyl-1,3-diaminopropane (50 µM)) had no effect on the growth of the cultured follicles. This study suggests that prior experiments associating ODC activity to hair growth were mistakenly directed towards that enzyme's product, putrescine and not the higher polyamines, especially spermidine. The authors of this paper state that "This suggests that spermidine is the essential polyamine for normal fiber growth . . . "

The importance of a specific individual polyamine to cellular growth and metabolism has been debated routinely in the scientific literature. Discussed herein below, it has been found to be very difficult to specifically perturb individual polyamines in an experimental setting. Compensatory mechanisms give rise to adjustments elsewhere in the pathway allowing the system to overcome whatever block has been imposed. An important modem tool has recently been brought to bear on this problem. Through the transgenic introduction of the rate-limiting catabolic enzyme responsible for the elimination of polyamine, spermidine/spermine acetyltransferase (SSAT), a marked change of the polyamine pools was noted. (Pietila et al., Activation of polyamine catabolism profoundly alters tissue polyamine pools and affects hair growth and female fertility in transgenic mice overexpressing spermidine/spermine N1-acetyltransferase. *J. Biol. Chem.* 1997, 272(30), 1876-51). Dramatic increases in the levels of putrescine together with increased enzymatic levels of S-adenosylmethioninedecarboxylase (AdoMetDC) were observed in the skin of transgenic mice. Only slight changes in the levels of the other polyamines, spermidine and spermine, were noted. The increased putrescine levels were explained by the metabolic disassembly of the higher polyamines via the introduced enzyme SSAT. This introduction of SSAT into these transgenic animals had a profound effect on their hair growth. Normal hair follicles were replaced with large cysts filled with a keratin-like substance. The epidermis of the transgenics was thickened and no hair shafts were seen. Pietila et al concluded that the increased level of putrescine in the skin of these animals led to the profound phenotypical changes observed.

An additional transgenic study supports the hypothesis that perturbations in the controls on putrescine levels have a dramatic effect on hair growth control. In 1996 O'Brien and coworkers reported on their studies on the transgenic introduction of gene for mutated ODC specifically associated with skin into mice. (Soler et al., supra). The transgene used in these studies used a skin-specific keratin 6 promoter. This study measured increased levels of putrescine in the skin of transgenic mice with little effect on the levels of spermidine or spermine. Follicular cysts with no hair growth were noted in these animals. DFMO given at 1% in the drinking water prevented this loss of hair growth when given before the first hair cycle had started. Furthermore, DFMO given after the above loss of hair caused the partial restoration of hair growth and completely regenerated normal follicle appearance. Soler et al. concluded that intracellular putrescine acts as a molecular switch regulating the behavior of the keratinocytes of the hair follicle. These studies were followed by an additional study using double transgenic mice over-expressing both SSAT and ODC. (Pietila et al., Relation of skin polyamines to hairless phenotype in transgenic mice overexpressing spermidine/spermine N1-acetyltransferase. *J. Invest. Dermatol.* 2001, 116(5), 801-805). Similar phenotypical changes were observed in this case also. In all of these studies the introduction of the SSAT or ODC transgene or both, despite paradoxical expectations to decrease or increase total polyamine levels respectively, resulted in elevated levels of putrescine. The resulting common phenotype of lack of hair growth and keratin filled cysts points to the importance of putrescine in skin biology.

Weekes et al showed that putrescine and its chain-extended analogs act as potent inhibitors of ODC induction when applied topically to mice prior to TPA treatment. (Weekes et al., Inhibition by putrescine of the induction of epidermal ornithine decarboxylase activity and tumor promotion caused by 12-O-tetradecanoylphorbol-13-acetate. *Cancer Res.,* 1980, 40, 4013-4018). They showed that the topical application of 20 μmole of putrescine 2 hr after the TPA treatment inhibited the induction of ODC activity by 50%. Treatment with spermidine, 1,7-diaminoheptane and spermine gave 90% inhibition when used at the same concentration. These same concentrations, when added directly to the assay medium, had no effect on the assay system. Furthermore, putrescine did not induce the production of detectable levels of ODC-antizyme in the mouse epidermis. Therefore, these diamines are inhibiting the induction of ODC by TPA. In the transgenic studies referenced above, the elevated putrescine produced maybe acting in a similar fashion, inhibiting the induction of ODC enzymatic activity.

It is now apparent that perturbations of cutaneous polyamine levels will affect hair growth. Numerous studies have shown that inhibition of ODC with α-difluoromethylornithine (DFMO), an irreversible inhibitor of ODC, reduces hair growth in mammals. Mice were found to have reduced hair growth when DFMO was systemically delivered via the drinking water (Takigawa, M. et. al., *Cancer Res.* 43:3732-3738 (1983)). Intravenous administration of DFMO decreased wool growth in sheep (Hynd, P. I. et. al., *J. Invest. Dermatol.* 106:249-253 (1996)) and oral administration of DFMO in cats and dogs produced alopecia and dermatitis (Crowell, J. A. et. al, *Fundam. Appl. Toxicol.* 22:341-354 (1994)). Additional evidence that ODC plays a role in hair follicle regulation resulted from a study in humans that were being treated for acute *Trypanosoma brucei* infections (African sleeping sickness) (Pepin, J. et. al. *Lancet* 2:1431-1433 (1987)) using DFMO. Patients using this treatment showed signs of hair loss mainly on the scalp but it was reversible after discontinuing treatment.

Polyamine biosynthesis has also been shown to be essential during the activation of immunocompetent cells (Fillingame, R. H. et. al., *Proc.Natl.Acad.Sci. USA* 72:4042-4045, (1975); Korpela, H. et. al., *Biochem. J.* 196:733-738 (1981)). Studies with DFMO confirm that polyamine depletion therapy can inhibit the immune response and may be a successful therapy against a number of autoimmune diseases. Both humoral and cell-mediated immune responses were affected by the anti-proliferative effect of polyamine depletion.

DFMO treatment of mice challenged with tumor allografts resulted in modified cytotoxic T-lymphocyte and antibody responses (Ehrke, J. M. et. al., *Cancer Res.* 46:2798-2803 (1986)). Reports by Singh et al. indicate that DFMO treatment may also ameliorate acute lethal graft versus host (ALGVH) disease in mice (Singh, A. B. et. al., *Clin.Immunol. Immunopathol.* 65:242-246 (1992)). Murine ALGVH represents a model of human GVH that contributes to the morbidity and mortality of bone marrow transplantation in humans and is characterized by anemia and the loss of T cell function and numbers. In this study, treatment of ALGVH mice with DFMO decreased mortality and anemia while preserving the cytotoxic T cell and natural killer cell population of the host.

Polyamine depletion therapy using DFMO has also been shown to benefit lupus-prone female NZB/W mice (Thomas, T. J. et. al., *J.Rheumatol.* 18:215-222 (1991)). Anti-DNA antibody production, immunoglobulin G and A synthesis, proteinuria and blood urea nitrogen were significantly reduced in treated mice. These studies indicate that polyamine depletion may beneficially treat several clinical autoimmune diseases including host versus graft disease, graft versus host disease and lupus. This antiproliferative strategy could be applied to other autoimmune diseases including cutaneous lupus, multiple sclerosis, atopic dermatitis, rheumatoid arthritis, scleroderma, inflammatory bowel disease, transplantation rejection and diabetes.

In modern societies the basic biological function of human hair, protection from the environment, has been lost. It is now desired that hair be removed from many parts of the human body in order to give a more cosmetically pleasing and socially acceptable appearance. There are many currently used methods to remove unwanted hair, none of which is entirely acceptable. These methods include; shaving, electrolysis, depilatory creams or lotions, waxing, tape-striping, depilatory devices, laser-mediated removal, tweezers plucking. Additionally, there are many examples of less than effective chemical hair growth inhibitors. Many of these currently used methods cause the undesired effect of thicker hair regrowth.

Examples of agents used in skin care products that have the effect of hair growth inhibition include agmatine, BHT or BHA, cetyl pyridinium chloride, bexamidine, ursolic acid, green tea catechins, phytosterols. Other agents known in the art to inhibit hair growth include: 1,10-phenanthroline; 5'-para-fluorosulphonyl benzoyl adenosine; 5-keto-D-fructose; 5-keto-D-fructose-1,6-bisphosphate; 6-amino-6-deoxy-glucose; agaric acid, 8-bromo-cAMP; cysteine sulphinic acid, D-mannosamine; diethylaminomalonate; doxycycline; ethacrynic acid; ethoxyquin; eupacunin; euparoin acetate; fluvastatin; guanidinosuccinic acid; inhibitor of a cysteine pathway enzyme; methacycline; mevastatin; mevinolin; minocycline; N-alpha-(p-tosyl)-L-lysine chloromethyl ketone; N-acetyl-beta-D-mannosoamine; oxaloacetic acid; phosphoclycerate; pravastatin; protocatechuic aldehyde; quinaldic acid; rivastatin; simvastatin; squalestatin; taxodione; taxodone; tetracycline; vemolepin; 1,8-diaminooctane; 2-methyl-6-heptyne-2,5-diamine; 3-carboxypropyl disulphide; saw palmetto extract; willow herb extract; pumpkin seed extract; 5-(N-benzyloxycarboyl-1-phenylalanamidomethyl)-3-bromo-4,5-dihydroisoxazole; 5'-deoxy-5'-methylthioadenosine; 6-heptyne-2,4-diamine; actinonin; alpha-methyl-DL-methionine; alpha-ethyl-ornithine; apigenin; arginase inhibitor; batimitast; caffeic acid; captopril; chlorotaurine; cholesterol pathway enzyme inhibitor; cyclooxygenase inhibitor; cysteamine; cysteinyl-glycine; d-cysteine; D-penicillamine; difluoromethylornithine (DFMO); L-difluoromethylornithine (L-DFMO); diethyl glyoxalbis(quanylhydrazone); diethyldithiocarbamic acid; dimethylcysteamine; doxycycline; eicosapentaenoic acid; estramustine; ethacrynic acid; etoposide; H-homoarginine; inhibitor of the formation of glycoproteins; proteoglycans or glycosaminoglycans; inhibitor of hypusine biosynthetic pathway; L-alanosine; L-argininamide; L-asparaginamide; L-cysteine methyl ester; lipoic acid; lovastatin; marimistat; matlystatin-B; meso-dimercaptosuccinic acid; methacycline; methylglyoxal bis(guanylhydrazone); minocycline; N(gamma)-methyl-L-arginine; N-[N[((R)-1-phosphonopropyl)-(S)-leucyl]-(S)-phenylalanine-N-methylamide;
N-acetylcysteine; N-phosphonalkyl dipeptides; N-phosphonoacetyl-aspartic acid; nalidixic acid; N-alpha-acetyl-L-arginine methyl ester; N-gamma-L-arginine benzyl ester; N-gamma-nitro-L-arginine; N-gamma-nitro-L-arginine methyl ester; nordihydroguaianetic acid (NDGA); extract from creosote; oxaloacetic acid; pantothenic acid; pantothenic acid analogs; phosphocysteamine; propyl gallate; protein kinase C inhibitor; quercetin; S-carbamyl-L-cysteine; S-trityl-L-cysteine; sulphasalazine; suppressor of angiogenesis; tetracycline; thiosalicyclic acid; tyramine; herbimycin; HNMPA(AM)3; inhibitor of alkaline phosphatase; lavendustin A; methyl caffeate; protein-tyrosine kinase inhibitors; tryphosstin A47; O-p-nitrohydroxylamine; alpha-fluoromethyl-histidine; mycophenolic acid; bromocryptine; cromoglycate; quinoline-3-carboxamide; 16 alpha or beta-substituted 4-aza-5-alpha-androst-1-en-3-ones; 2-aryl-indole derivatives; 2-phenyl-3-aminoalkyl-indole derivatives; 3-oxo-4-aza-5-alpha-androstane derivatives; 5-alpha-androstan-3-ones; 5-(aminocarbonylalkyl)-3-heterobicyclyl-alkylaminoalkyl)-2-phenylindole derivatives; 6-azaindole derivatives; 7-azaindole derivatives; aryl-imidazo-pyridines; finasteride; GnRH inhibitors; aloe; carboxylalkylamine derivatives; clove; *Echinacea angustifolia; Echinacea purpurea*; elasatin decomposition enzyme inhibitor; extracts from ginger; hydrolyzing almond; lithosperumum; peptides; extract of rosaceae; extract of *sanguiosorba officinalis; tropaeolum majus*; extract of white birch and rubiaceae plant groups; extract of *juniperus* genus and/or malt extract; malonamide derivatives; elastase inhibitor; papain; trypsin; chymotrypsin; pepsin; bromelain; ficin or pancreatin; plant fruit enzyme extracts; compounds from pleinoe sp; *curcuma longa* L or *Biopyros kaki*; 2-indole carboxylic acid derivatives; alpha-TNF antagonist; aminopropanes; bacterium ribosomes; non-steroidal anti-inflammatory drugs (NSAIDS); diethylenediamines; histamine antagonist; interleukin-1 antagonist; lipoxygenase inhibitors and stimulants; phenothizaines; sulfotransferase inhibitors; tetrazolyl-benzofuran carboxamides; tetraazolylbenzothiophene carboxamides; cyanoguanidine derivatives; 17alpha-hydroxy-4,9(11)-pregnadiene-3,20-dione derivatives; anti-angiogenic steroids; pyrimidine-cyanoguanidine derivatives; substituted amidine or guanidine; benzothotphene derivatives; (–)-cis-6(S)-phenyl-5(R)-[4-(2-pyrrolidin-1-ylethoxyphenyl]-5,6,7,8-tetrahydronaphehenen-2-ol D-tartrate ietrahydronaphthalene derivatives; estrogen agonists or antagonists; tetrahydroisoquinolines; heptapeptide luteinising hormone releasing hormone (LHRH) analogs; 3-(anilinomethylene)oxindole derivatives; bezo-[f]-quinolin-3-one derivative; ((S-(–)-N-(alpha-ethylbenzyl)-3-hydroxy-2-phenylquinoline-4-carboxamide); 24-ethyl-(delta)-4,22-cholestadien-3-one; extracts from *Hydrangea macrophylla; Hydrangea serrata*; Iridaceae belamcanda adans; iridaceae *Iris* I; moraceae *humulus*; CDK binding proteins; chimeric polypeptide with cyclin-dependant binase (DK) binding motif; E6AP-binding polypeptides; 2-mercaptoethanol; 2-mercaptopropionic acid; cysteine; diethyldithiocarbamic acid; dithiothreitol; glutathione; homocysteine; lipoic acid; 3-mercaptopropionic acid; N-acetyl-L-cysteine; thiodiclycol; thiodicyclolic acid; thioglycerol; thioglycolic acid; thiolactic acid; thiomalic acid; thiosalicyclic acid; thioxanthine; benzoid acid lactone ether; 1-halomethyl-5-alpha-androstanes and delta-androstanes; hedgehog antagonists; patched antagonists; copper; iron; zinc; 1-dehydromelengestrol acetate; 1-dehydromegestrol acetate; chlormadinone acetate; cyproterone acetate; medroxyprogesterone acetate; megestrol acetate; melengestrol acetate; nomegestrol acetate; non-elastomeric polyolefin resin; partially fluorinated polyolefin resin; nucleic acid molecule; trypsin analogs; bacteriostatic or maemostyptic agnt; stannous fluoride; alpha- or gamma-linolenic acid; EGF; lipoxygenases; extract of regulo plant (*abelmoschus moschatus*); extract of wolo plant (*borassus flabellifer*); androstenedione analogs; activin A (polypeptide); hydrindanes; butyric acid derivatives; phytoestrogen; tetrahydroisoquinolines; tetrahydronaphthalenes; 3-amino-2,3-dihydrobenzoic acid; 6-fluoro-2,5-diamino hexanoic acid; (S)-2-amino-4-aminooxybutyric acid; extracts of fruits and other plant parts from *serenoa repens*; carrot oil; clove oil; diazo compounds; essential oil; honey; juniper oil; lavender oil; lemon juice; palmarosa oil; rosemary oil; sugar; sugary substance; *thuja* oil; triarylmethane compounds; S-nitrosoglutathione; 1-diethyl-2-hydroxy-2-nitrosohydrazine; S-nitrosocysteine; nitroglycerin; perfluoro-substituted aniline derivatives; 17-alpha-propyltestosterone; 4-androstene-3-one-17-beta-carboxylic acid; (4R)-5,10-seco-19-norpregna-4,5-diene-3,10,20-trione; chlormadinone acetate; cyproterone acetate; progesterone; spironolactone; melatonin; Boeman Birk inhibitor (soy derived); 2-substituted-6-tetrahydronaphthyl or indanyl naphthalene derivatives; aqueous alcoholic extract from genus *Centipeda*; antaonist of hedgehog signal transduction pathway; epidermal growth factor (EGF); finasteride; fatty acids; 2-phenylbenzothiophene derivatives; 2-arylimino-oxaza or thiaza heterocyclic compounds; glutathione synthesis stimulators; indole derivatives; *Cinnamonum verum; Curcurbita pepo; Epilobium roseum; Salvia officinalis; Serenoa repens; Cassia obtusifoila linne*; polynucleotide; dormant cell extracts; N-substituted benzyl or thienylmethyl-4-pyridone compounds; (1H)-benzo(c) quinolizin-3-one derivatives; 5-alpha reductase inhibitors; adenylsuccinate synthetase inhibitors; aspartate transcarbamylase inhibitor; gammaglutamyl traspeptidase inhibitor; ornithine decarboxylase inhibitors; citric acid; Dead Sea salt; vitamin K; Cucurbitaceae; extract of Ikurinin; phosphodiesterase inhibitors; phlondrin; phloretin; 5-alphaandrostene-3-alpha-17-betadiol; cyproterone; Hedera helix; Lithospermum root; medoroxyprogesterone; mestanolone; norethisterone; *Scutellaria* root; tomato; extract of *Commiphora myrrha; Cymbopogon nardus; Lagerstroemia speciosa; phyllanthus nuriri; Smilaz zeylanica; Woodfordia fruticosa*; chelating agents; chlorophenol; ortho-phenyl-phenol; niphtolide; peach oil; sorbic acid; *Cistanche salso; Plantago asiatica; Stachys sieboldii;* 2-amino-5-substituted benzophenone; aniline derivatives; bur marigold infusion; camphoroil; citric acid; conifer extract; daisy infusion; honey; sea-buckthorn oil; tannin solution; *capsicum; capsicum* extract (Solanaceae family); conjucate comprising active agent substituted with amino acid peptide or trisamine carrying fatty acid ester and dithioalkanoyl groups; recombinant DNA encoding EGF; recombinant DNA encoding TGFalpha; 11-beta-aryl-17-spiro-pyrrolin-2-ylidene N-oxide steroid progestins and antiprogestins; phenyl imidazolidines; ammonium salt of weaker acids; essential oils; vitamin F; coumarin derivatives; leuteinizing hormone-releasing hormone; leuteinizing hormone-releasing hormone analogs; hydroxamic acid derivatives; bomeol; cineole; linalool; methyl heptenone; oil of ginger; shogaol; zingerone; zingiberol; zingiberone; glutathione S-transferase modulator; aminoacid(s); lipoxydase; inhibitor of glutamine metabolism thiomolybdate compound; hairless protein inhibitor; aromatase inhibitor; trifluoroanilide derivatives; EGF; EGF analogs; and extract of seeds of Coix lachrymal-jobi.

Shander et.al. describes the use of sulfhydryl active compounds as mammalian hair growth inhibitors. (U.S. Pat. No. 6,743,419).

Other categories of agents that may be added to a therapeutic or cosmetic product suitable for various cutaneous applications include: surfactants; desquamation actives; anti-acne agents; anti-wrinkle actives and anti-atrophy agents; vitamin B3 compounds; retinoids; anti-oxidant or radical scavenging agents; chelators, flavonoids; anti-inflammatory agents; anti-cellulite agents such as caffeine, theophylline, theobromine or aminophylline; tanning agents such as dihydroxyacetone; skin lightening agents such as kojic acid, arbutin, transexamic acid; antimicrobial agents useful for destroying disease or odor causing bacteria; sunscreening agents; and skin conditioning agents.

Numerous biochemical studies have shown that cellular polyamine concentrations are tightly regulated at various control points. Overall, these control points can be divided into those that control the biosynthesis of polyamines from amino acid derived precursor molecules, those that control the transport into the cell from external sources and finally those that degrade the higher polyamines into their smaller components. Of these three ways to obtain and interconvert between the various forms of the polyamines only the biosynthetic and transport pathways allow the cell to gain additional carbon atoms into the cycle.

Polyamine biosynthesis involves two highly regulated enzymes, ornithine decarboxylase and S-adenosylmethionine decarboxylase, and two constitutively expressed enzymes, spermidine synthase and spermine synthase. The activities of the first two enzymes, the decarboxylases, are tightly regulated through a variety of growth factors and by the presence of their products. The activities of the other two enzymes, the aminopropyltransferases (spermidine synthase and spermine synthase), are mainly controlled by the availability of their substrates (i.e. the products of the decarboxylase enzymes). Furthermore, the cell can compensate for its requirements for polyamines by a specific polyamine transport system. Increased needs for polyamines following stimulation with growth factors or decreased needs following over-incorporation of polyamines results in compensatory changes in transport activity. The biochemical rheostat or regulator by which the cell can control both polyamine biosynthesis and transport has been defined as the antizyme system.

Bey et al discussed mechanism-based irreversible inhibitors of polyamine biosynthesis of both the enzyme ornithine decarboxylose (ODC) substrate and product of the ODC enzyme. (Bey, P. et al., *J. Med. Chem.* 1983, 26, 1551-1556). A review of this research can be found in Bey, P. et al., in "Inhibition of Polyamine Metabolism" pp. 1-31 eds. P. P. McCann, A. E. Pegg and A. Sjoerdsma, Academic Press. 1987. In their review, Bey et al., categorize inhibitors of ODC into three major types: (1) analogs of substrate or product which act as competitive inhibitors; (2) molecules capable of interacting or combining with the PLP cofactor; and (3) enzyme-activated irreversible inhibitors designed on either the substrate or product.

A good deal of research has defined the requirements for inhibitors of analogs of ornithine and putrescine. The L-configuration of the α-amino acid is preferred for substrate analogs of ornithine. A potent reversible inhibitor, α-methylornithine 1, shows this profound stereochemical preference (L-(S)-α-methylornithine $K_i$=19 µM; D-(R)-α-methylornithine $K_i$=1300 µM). (Bey et al., *J. Med. Chem.* 1978, 21 (1), 50-55). The carboxyl group can be substituted by a tetrazoyl group. A distance of about 6 Å between the nitrogen atoms is believed to be optimal for binding to the active site. Structural features, such as unsaturation in a trans geometry, which favor this stretched conformation, increase the affinity to the enzyme. (Relyea et al., *Biochem. Biophys. Res. Comm.* 1975, 67, 392-402). Reylea et al. suggested that an adduct forms between 1,4-diamino-trans-2-butene 3 and the PLP cofactor before binding to the enzyme. The authors of the previous report (Rey et al) suggest that a hydrophobic interaction favors the binding of this molecule. Substitutions on the α-carbon are allowed (see α-methylomithine above). Substitutions on the δ-nitrogen of ornithine are not allowed.

Substrate based ODC inhibitors are shown below.

α-methylornithine, 1 ($K_i$=40 µM) (Bey et al, supra)

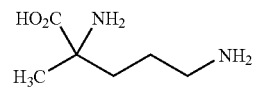

1 trans-1,4-diaminocyclohexane-1-carboxylic acid, 2 ($K_i$=70 μM) (Bey et al, supra)

1,4-Diamino-trans-2-butene, 3 ($K_i$=2 μM) (Reylea et al, supra)

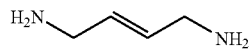

trans-3-dehydroornithine ($K_i$=4.4 μM) (Reylea et al, supra)

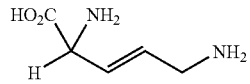

1,4-Phenylenediamine 4 ($K_i$=46 μM) (Solano et al., The 1,2 and 1,3 isomers of Phenylenediamine were essentially inactive; *Int. J. Biochem.* 1988, 20 (4), 463-470).

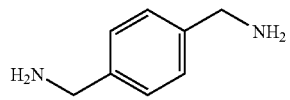

1,4-Dimethylputrescine (Moyano et al., *J. Med. Chem.* 1990, 33 (7), 1969-74

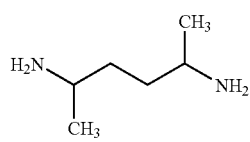

p-Aminomethyl-phenylglycine (Ben-ishai et al., *Tetrahedron,* 1977, 33, 2715-2717).

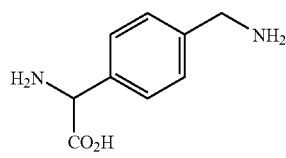

trans-1,4-diaminocyclohexane (CAS RN [2615-25-0])

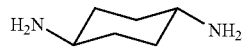

trans-1,4-diaminomethylcyclohexane

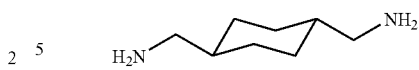

Di-α-methyl-p-phenylenediamine

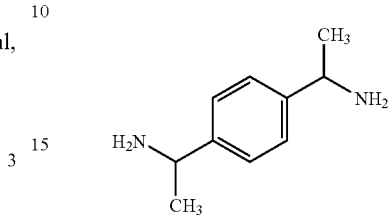

1,4-Diaminomethylnaphthylene

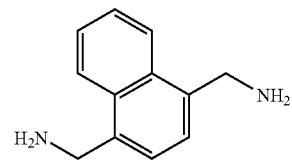

N,N'-Bis(3-aminopropyl)-2-butene-1,4-diamine (CAS RN [110319-68-1])

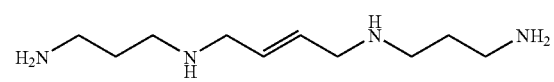

The x-ray crystal structure of ODC has recently been determined. (Almrud et al., *J. Mol. Biol.* 2000, 295(1), 7-16). A generally accepted assumption in the polyamine field is that it requires an irreversible ODC inhibitor to effectively deplete cellular polyamines. Explanations for this include the fast turnover of the enzyme, lack of specificity and the general lack of potency of competitive inhibitors. Furthermore, several of these have been shown to increase the apparent half-life of the enzyme through stabilization. (Harik et al., *Mol. Pharmacol.* 1974, 10, 41-47; McCann et al., *Biochem. Biophys. Res. Comm.* 1977, 76, 893-899).

Cofactor interaction-based inhibitors exploit the requirement in all α-amino acid decarboxylase enzymes for the vitamin $B_6$ cofactor pyridoxal phosphate (PLP). By incorporating a strongly nucleophilic moiety into a substrate or product analog an extremely stable adduct is formed between PLP and the inhibitor. Several of these molecules are extremely potent inhibitors with $K_i$ values into the low nanomolar range. α-Hydrazinoornithine showed a $K_i$ value of 0.5 μM. (Inoue et al., *J. Biochem* (Tokyo), 1975, 77, 879-893). An improved method of synthesis of this molecule has been reported. (Sawayama et al., *Chem Pharm. Bull.* 1976, 24, 326-329). A set of aminooxy putrescine analogs have been described which are extremely potent. (Khomutov et al., *Biochem Biophys Res. Commun.* 1985, 130, 596-602). The second of these shown below, 1-aminooxy-3-aminobutane, has a methyl group in the α-position to the amino functionality to prevent oxidative metabolism by amine oxidase enzymes.

α-Hydrazinoornithine ($K_i=0.5$ μM) (Kahana et al., *Proc Natl Acad Sci USA* 1984, 81(12), 3645-9).

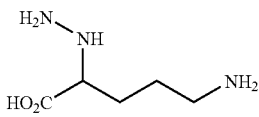

1-Aminooxy-3-aminopropane ($K_i=0.0032$ μM) (Sawayama et al., *Chem Pharm. Bull.* 1976, 24, 326-329).

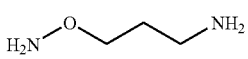

1-Aminooxy-3-aminobutane ($K_i=0.0028$ μM) (U.S. Pat. No. 5,610,195 to Frei et al).

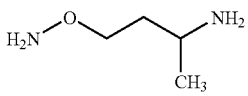

1-aminooxy-3-amino-2,2-difluoropropane

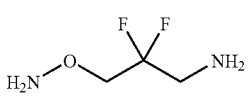

1-hyrazino-3-aminopropane

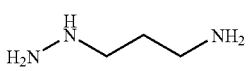

1-Aminooxy-3-amino-3-methylbutane

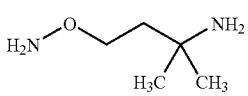

1,2-diaminooxyethane

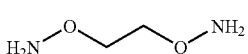

Because of microscopic reversibility of the protonation step in the mechanism of ODC, latent chemically reactive groups can be placed on either a substrate or product analog to produce a mechanism-based ODC inhibitor. (Bey et al., Inhibition of Polyamine Metabolism, supra). Tables 1 and 2 show various substrate analogs while Tables 3 and 4 show product analog inhibitors. In these tables $K_i$ is the apparent dissociation constant and $\tau_{1/2}$ is the time of half-inactivation extrapolated to infinite concentration of inhibitor. Lower numbers in both instances mean better inhibitors. Data in the tables are from rat liver enzyme.

Introduction of a double bond in the β,λ-position of these analogs generated analogs with much higher activity. The difluoromethyl analogs in both the saturated (DFMO) and unsaturated analogs have been resolved into their enatiomerically pure forms. The (−)-versions are more active.

TABLE 1

Reaction catalyzed by ODC and substrate analog mechanism-based inhibitors.

| R Group | Ki value (μM) | τ₅₀ (min) | Reference |
|---|---|---|---|
| —CHF₂ (DFMO) | 39 | 3.1 | Metcalf et al. J.Am. Chem. Soc. 1978, 100, 2551-2553 |
| —CH₂Cl | No satd kinetics | $t_{1/2}$ = 22 min at 100 μM | Sawayama et. al, supra |
| —CH₂F | 75 | 1.6 | Metcalf et al. J.Am. Chem. Soc. 1978, 100, 2551-2553 |
| —CH₂CN | 8700 | 29 | Sawayama et. al, supra |
| —CH=CH₂ | 810 | 27 | Danzin et al. J. Med. Chem. 1981, 24, 16-20 |
| —CCH | 10 | 8.5 | Metcalf et al. J.Am. Chem. Soc. 1978, 100, 2551-2553 |
| —CH=C=CH₂ | ? | ? | Castelhano, et al., J. Chem. Soc. 1984, 106, 2734-2735 |

TABLE 2

Unsaturated substrate mechanism-based ODC inhibitors.

| R Group | $K_i$ value (μM) | τ₅₀ (min) | Reference |
|---|---|---|---|
| —CH₃ | 2.7 | Not a mechanism-based inhibitor | U.S. Pat. No. 5,610,195 |

TABLE 2-continued

Unsaturated substrate mechanism-based ODC inhibitors.

[Structure: HO₂C-C(R)(NH₂)-CH=CH-CH₂-NH₂ with H₂N]

| R Group | $K_i$ value (µM) | $\tau_{50}$ (min) | Reference |
|---|---|---|---|
| —CH₂F | 2.7 | 2.6 | Metcalf et al, supra |
| —CHF₂ | 30 | 2.6 | U.S. Pat. No. 5,610,195 |

In terms of the latent reactive functionality, the product analogs shown in Table 3 generally follow the same trends in potency as the substrate analogs in Tables 1 and 2. An unfortunate coincidence occurs with α-ethynylputrescine and α-fluoromethyl-putrescine when used in vivo. These analogs inhibit not only ODC but also the enzyme 4-aminobutyrate transaminase (GABA-transaminase). Since these analogs are substrates for monoamine oxidase they are converted to the GABA analogs, which potently inhibit the GABA-transaminase. This is not acceptable due to the profound CNS effects of such inhibitors.

Introduction of a α-methyl group is known to prevent oxidation by monoamine oxidase enzymes and substituents are allowed on the δ-position of ODC substrates thus addition of such a methyl group was successfully tried. This analog, δ-methyl-α-ethynylputrescine, was resistant to oxidation and retained high ODC inhibitory properties. Introduction of this methyl group presents a substantial stereochemical problem since there are now 4 possible diastereoisomers. Each was synthesized and the active molecule was found to be the (2R, 5R) isomer. (Casara et al., *J. Chem. Soc. Perkin Trans. I*, 1985, 2201-2207).

Subsequent work utilized an alternative chemical approach to prevention of the monoamine oxidase metabolism. Introduction of two fluorine atoms in the β-position of α-ethynylputrescine provides a molecule without the stereochemical liability of the α-methyl derivative while also preventing the oxidation problem. (Kendrick et al., *J. Med. Chem.*, 1989, 32, 170-173). This molecule, 2,2-difluoro-5-hexyne-1,4-diamine, is shown in Table 3 ($K_i$=10 µM). In vivo data in rats using this inhibitor described in this paper shows a dramatically long-lasting dose-dependant inhibition of ODC of the ventral prostate tissue following oral administration (50 mg/kg by gavage still showed >50% inhibition after 24 h).

TABLE 3

Product analog mechanism-based inhibitors of ODC.

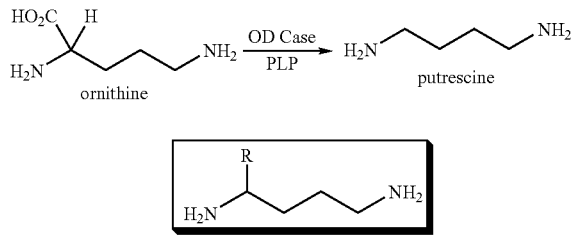

| R Group | $K_i$ value (µM) | $\tau_{50}$ (min) | Reference |
|---|---|---|---|
| —CH₃ | 520 | No time-dependant inhibition | Danzin et al., Biochem. Pharmacol. 1982, 31, 3871-3878 |
| —CH₂F | 56 | 4.4 | Casara et al, supra |
| —CHF₂ | 30 | 7.4 | Casara et al, supra |
| CH=CH₂ | 540 | 10 | Metcalf et al, supra |
| —CCH | 2.3 | 9.7 | Sawayama et al, supra |
| —CCHw/δ-CH₃ | 13.5 | 1.8 | Danzin et al., J. Biochem. Biophys. Res. Comm. 1983, 116, 237-243. |
| —CCHw/γ-CF₂ | 10 | 2.4 | Castechano et al, supra. |
| —CH=C=CH₂ | 160 | 8 | Danzin et al, FEBS Lett., 1984, 174, 275-278. |

TABLE 4

Unsaturated product analog mechanism-based inhibitors of ODC.

[Structure: H₂N-C(R)(H)-CH=CH-CH₂-NH₂]

| R Group | $K_i$ value (µM) | $\tau_{50}$ (min) | Reference |
|---|---|---|---|
| —CH₂F | 42 | 0.2 | Bey et al., J. Med Chem, supra. |

TABLE 4-continued

Unsaturated product analog mechanism-based inhibitors of ODC.

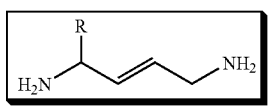

| R Group | K$_i$ value (μM) | τ$_{50}$ (min) | Reference |
|---|---|---|---|
| —CHF$_2$ | 60 | 0.7 | Bey et al., Inhibition of Polyamine Metabolism, supra. |
| —CCH | 1 | 5 | Sawayama et al.,supra. | d. Nitrosylation—The ODC enzyme protein has been shown to be nitrosylated resulting in inhibition of its activity. (Bauer et al., Nitric Oxide Inhibits Ornithine Decarboxylase via S-Nitrosylation of Cysteine 360 in the Active Site of the Enzyme. *J. Biol. Chem.*, 2001, 276, 34458-34464).

Other ODC inhibitors described include retinoic acid. (Zheng et al., Regulation of the induction of ornithine decarboxylase in keratinocytes by retinoids. Biochem J. 1995, 309, 159-65). The following agents were discovered through the use of an in vitro cell-based assay which inhibited the TPA-mediated increase in ODC activity in cultured mouse epidermal 308 (ME 308) cells: apigenin, benzylisothiocyanate, curcumin, diallyl disulfide, N-(4-hydroxyphenyl)retinamide (4-HPR), menadione, miconazole, nordihydroguaiaretic acid (NDGA) and phenethyl isothiocyanate. (Lee et al., Evaluation of the potential of cancer chemopreventive activity mediated by inhibition of 12-O-tetradecanoyl phorbol 13-acetate-induced ornithine decarboxylase activity. *Arch Pharm Res.* 1999, 22(6), 559-64).

There also exists a potential biological method to inhibit the induction of skin ODC activity caused by a variety of chemical or physical treatments. A number of studies have explored the ability of various agents to prevent the physical (UV radiation) or chemical (12-O-tetradecanoylphorbol-13-acetate (TPA)) induced increase in ODC activity in the skin. In 1986, Black and coworkers explored the mode of action of butylated hydroxytoluene-mediated photoprotection. (Koone et al., A mode of action for butylated hydroxytoluene-mediated photoprotection *J. Investig. Derm.* 1986, 87 (3), 343-347). They used orally ingested BHT in a murine model for protection from photocarcinogenesis. They noted that BHT significantly decreases UV radiation induction of epidermal ornithine decarboxylase activity. This paper examines the possibility that BHT provides this ODC inhibition and the resulting carcinogenesis protection by altering the chemical or physical properties of the stratum corneum. Mice were treated orally (in food) with 0.5% BHT for two weeks prior to ODC activity determination. The control group did not received any BHT. A 65% more UV radiation transmission in these controls was observed after excising stratum corneum samples. BHT caused a 70% inhibition of measured ODC activity. No differences in ODC activity were observed in comparisons between BHT-fed animals that had their stratum corneum stripped away prior to UV irradiation and those of UV irradiated non-stripped controls. Black et al suggested that irritation by the stripping could not account for the induction of ODC. Furthermore, it was shown that transmission differences could not be attributed to changes in the thickness or number of layers of stratum corneum. Black et al suggested that the protective role induced by BHT is due to its effects on the chemical not physical properties of the stratum corneum, possibly through an antioxidant effect.

Kozumbo and coworkers explored the ability of various antioxidant compounds to prevent TPA-induced epidermal ODC activity. (Kozumbo et al., Inhibition by 2(3)-tert-butyl-4-hydroxyanisole and other antioxidants of epidermal ornithine decarboxylase activity induced by 12-O-tetradecanoylphorbol-13-acetate. *Cancer Res.* 1983, 43, 2555-2559). They monitored the inhibition of the induction of ODC activity resulting following TPA treatment. Various antioxidant agents including BHA and 14 various analogs were tested by topical application to mice. A structure-activity study was performed that implied that hydroxyl and tert-butyl substituents played a significant role in their antioxidant-mediated antagonism of the induction of ODC by TPA. Their free radical scavenging mechanism of action is supported by the experiment showing no ODC inhibition when the agent is placed in the assay medium.

Another report described the inhibitory effects of anti-inflammatory drugs, a steroid triamcinolone and a NSAID indomethacin, on the UV-based induction of ODC activity in mouse skin. (Lowe et al., Antiinflammatory drug effects on ultraviolet light-induced epidermal ornithine decarboxylase and DNA synthesis. *J. Investig. Dermatol.*, 1980, 74, 418-420). Young and coworkers explored the wavelength dependence for the induction of ODC in the skin of UV irradiated mice. The results that this induction was highest between the 260 and 310 nm suggested that the chromophore was a protein. (Young et al., UV wavelength dependence for the induction of ornithine decarboxylate activity in hairless mouse epidermis. *Carcinogenesis*, 1986, 7(4), 601-604).

Work described by Shirahata showed that the design of specific and potent (<1 μM K$_i$) inhibitors of the aminopropyltransferase enzymes spermidine and spermine synthase is possible. (Shirahata et al., Putrescine or spermidine binding site of aminopropyltransferases and competitive inhibitors. *Biochem. Pharm.* 1991, 41(2), 205-212). The molecules described have the advantage of being small and simple to produce. They have outstanding appeal for use in dermal applications such as hair growth inhibition. Analogs for inhibition of spermidine synthase include (IC$_{50}$ in μM): cyclohexylamine (8.1), trans-4-methylcyclohexylamine (1.7) and exo-2-aminonorbornane (5.5). Furthermore, the simple molecules 5-amino-1-pentene, 1-butylamine (3.8) and 1-pentylamine (3.6) compounds showed respectable activity.

The effect of treatment with spermidine and spermine synthase inhibitors on the levels of polyamines in rat tissues is described in Shirahata et al., Effects of inhibitors of spermidine sythase and spermine synthase on polyamine synthesis in rat tissues. *Biochem Pharmacol.* 1993, 45(9), 1897-903. Oral administration of 4-methylcyclohexylamine (4MCHA) or N-(3-aminopropyl)cyclohexylamine (APCHA) at 0.02% or 0.1% in drinking water resulted in significantly reduced levels of spermidine or spermine in rat prostate. Lesser reductions were observed in rat liver, kidney or brain. Only very small amounts of drugs were seen in these tissues following this delivery method. A note was made to the relatively low toxicities of these two compounds. The LD$_{50}$ values in rats are more than 250 mg/kg for 4MCHA and 500 mg/kg for APCHA for a 10-day treatment with drug in drinking water. A further point made by the paper was the inability of spermine depletion alone to affect the weight of the tissues.

Baillon et al describe the effect of some simple analogs of diaminopropane against spermine synthase using both isolated enzyme and whole cells. (Baillon et al., Inhibition of mammalian spermine synthase by N-aklylated-1,3-diaminopropane derivatives in vitro and in cultured rat hepatoma cells. *Euro. J. Biochem.* 1989, 179, 17-21). Potent inhibition of the enzyme was noted in both settings. Treatment of cells resulted in the appearance of drug in the cell (N-butyl-1,3-diaminopropane was the best with a $K_i$ of 11.9 nM) showing effective uptake of the molecule. No great effect was seen on cellular polyamine levels (spermine and putrescine were reduced while spermidine levels were higher) following treatment with 50 µM N-butyl-1,3-diaminopropane. Baillon et al confirmed the potent activity of n-butylamine against the enzyme spermidine synthase ($K_i$=0.52 µM). They conclude with the statement, "altogether these findings are consistent with the idea that spermine synthesis is not needed for a normal growth rate provided that a compensatory increase in spermidine occurs."

Other spermidine or spermine synthase inhibitors include the multisubstrate analog inhibitors reported by Coward and coworkers. These include adenosylspermidine AdoDATO, and AdoDATAD. (Lakanen et al., Synthesis and biochemical evaluation of adenosylspermidine, a nucleoside-polyamine adduct inhibitor of spermidine synthase. *J. Med. Chem.* 1995, 38(14), 2714-27; Tang et al., Synthesis and evaluation of some stable multisubstrate adducts as specific inhibitors of spermidine synthase. *J. Med. Chem.* 1981, 24(11), 1277-84; and Woster et al., Synthesis and biological evaluation of S-adenosyl-1, 12-diamino-3-thio-9-azadodecane, a multisubstrate adduct inhibitor of spermine synthase. *J. Med. Chem.* 1989, 32(6), 1300-7; respectively).

Polyamine transport into mammalian cells is energy and temperature dependent, saturable, carrier mediated and operates against a substantial concentration gradient. (Seiler, N. et al., Polyamine transport in mammalian cells. *Int. J. Biochem.* 1990, 22, 211-218; and Khan, et al., Characterization of polyamine transport pathways, in *Neuropharmacology of Polyamines* (Carter, C., ed.), 1994, Academic, San Diego, pp. 37-60). Ample experimental evidence exists that polyamine concentration homeostasis is mediated via this transport system. Changes in the requirements for polyamines in response to growth stimulation are reflected by increases in the transport activity. Stimulation of human fibroblasts to cell proliferation by serum or epidermal growth factor was followed by an 18-100 fold increase in the uptake of putrescine (DiPasquale, A. et al., Epidermal growth factor stimulates putrescine transport and ornithine decarboxylase activity in cultures human fibroblasts. *Exp. Cell Res.* 1978, 116, 317-323; and Pohjanpelto, P. Putrescine transport is greatly increased in human fibroblasts initiated to proliferate. *J. Cell Biol.* 1976, 68, 512-520). Tumors have been shown to have an increased rate of putrescine uptake. (Volkow, N. et al., Labeled putrescine as a probe in brain tumors. *Science*, 1983, 221, 673-675; and Moulinoux, J-P. et al., Biological significance of circulating polyamines in oncology. *Cell. Mol. Biol.* 1991, 37, 773-783).

Genes for the polyamine transport protein or complex have been cloned from *Escherichia coli* and yeast. (Kashiwagi, K. et al., *J. Biol. Chem.* 1990, 265, 20893-20897; and Tomitori, H. et al., Identification of a gene for a polyamine transport protein in yeast. *J. Biol. Chem.* 1999, 274, 3265-3267). The genes for the mammalian transporter await identification although Belting has hypothesized that glypican-1 may be involved. (Belting et al., Glypican-1 is a vehicle for polyamine uptake in mammalian cells: a pivital role for nitrosothiol-derived nitric oxide. *J. Biol. Chem.* 2003, 278(47), 47181-9). A subunit of the transporter from *E. coli* has been crystallized and its X-ray structure has been determined. (Sugiyama, S. et al. Crystal structure of PotD, the primary receptor of the polyamine transport system in *Escherichia Coli. J. Biol. Chem.* 1996, 271, 9519-9525). Since this structure was determined on a prokaryotic species, its use in the design of mammalian transport inhibitors was deemed to be of limited value.

The ability of polyamine analogs to inhibit the uptake of $^3$H-spermidine into cells has been studied. Bergeron and coworkers studied the effect of addition of different alkyl group substitutions on the terminal nitrogen atoms of spermidine or spermine analogs. (Bergeron, R. J. et al. Antiproliferative properties of polyamine analogs: a structure-activity study. *J. Med. Chem.* 1994, 37, 3464-3476).

Bergeron et al showed that larger alkyl groups diminished the ability to prevent uptake of radiolabeled spermidine. It was later concluded that increases in the number of methylenes between the nitrogen atoms decreased the ability to compete for $^3$H spermidine uptake. (Bergeron, R. J. et al., A comparison of structure-activity relationships between spermidine and spermine antineoplastics. *J. Med. Chem.* 1997, 40, 1475-1494). Bergeron et al also concluded that the polyamine transport apparatus requires only three cationic centers for polyamine recognition and transport. (Porter, C. W. et al. *J. Cancer Res.* 1984, 44, 126-128). Examples of the polyamine analogs' ability to inhibit $^3$H spermidine uptake into L1210 cells by CoMFA and QSAR methods have also been analyzed. (Li, Y. et al. Comparative molecular field analysis-based predictive model of structure-function relationships of polyamine transport inhibitors in L1210 cells. *Cancer Res.* 1997, 57, 234-239; and Xia, C. Q. et al. QSAR analysis of polyamine transport inhibitors in L1210 cells. *J. Drug Target.* 1998, 6, 65-77). A radiochemical assay is used for biochemical analysis of transport and has been used to study polyamine transport in yeast and a variety of mammalian cells. (Kakinuma, Y. et al., *Biochem. Biophys. Res. Comm.* 1996, 216, 985-992; and Seiler, N. et al., *Int. J. Biochem. Cell Biol.* 1996, 28, 843-861).

A number of series of polyamine transport inhibitors has been reported in Covassin et al., Xylylated dimers of putrescine and polyamines: influence of the polyamine backbone on spermidine transport inhibition. *Bioorg Med Chem Lett.* 2003, 13(19), 3267-71; Covassin et al., Synthesis of spermidine and norspermidine dimers as high affinity polyamine transport inhibitors. *Bioorg Med Chem Lett.* 1999, 9(12), 1709-1714; and Huber et al., 2,2'Dithiobis(N-ethylspermine-5-caboxamide) is a high affinity, membrane-impermeant antagonist of the mammalian polyamine transport system. *J Biol. Chem.* 1996, 271(44), 27556-63.

A series of amino acid spermine conjugates has been described. (Burns et al., Amino acid/spermine conjugates: polyamine amides as potent spermidine uptake inhibitors. *J. Med. Chem.* 2001, 44, 3632-44; Weeks et al., *Exp. Cell Res.* 2000, 261, 293-302; and Devens et al., *Prostate Cancer and Prostatic Diseases* 2000, 3, 275-279). A group of spermine dimers have been shown to be excellent polyamine uptake inhibitors. (Graminski et al., Synthesis of bis-spermine dimers that are potent polyamine transport inhibitors. *Bioorg Med. Chem. Lett.* 2002, 12, 35-40). Several potent polyamine transport inhibitors are disclosed in Vermeulen, N. et al., Polyamine analogues as therapeutic and diagnostic agents, U.S. Pat. No. 6,172,261 to Burns, M. R. et al., Hydrophobic polyamine analogs and methods of their use and PCT patent application WO/02053519.

Increasing concentrations of intracellular polyamine levels induce the production of antizyme which negatively regulates ODC by binding to it and targeting it for destruction. Antizyme has also been shown to inhibit polyamine uptake (Mitchell, J. L. et. al., *Biochem. J.* 299:19-22 (1994); Suzuki, T. et. al., *Proc. Natl. Acad. Sci. USA* 91: 8930-8934 (1994); Sakata, K et. al., *Biochem. Biophys. Res. Commun* 238:415-

419 (1997)) and recent evidence suggests that antizyme may increase polyamine excretion (Sakata, K. et. al., *Biochem J.* 347:297-303 (2000)). Therefore, antizyme can very effectively limit the accumulation of cellular polyamines.

Antizyme has been found in vertebrates, fungi, nematodes, insects and eukaryotes (Ivanov, I. et. al., *Nucleic Acids Res.* 28:3185-3196 (2000)). Three antizyme isoforms, AZ1, AZ2 and AZ3, have now been identified among vertebrates. Both AZ1 and AZ2 have wide tissue distribution but AZ2 mRNA is less abundantly expressed. AZ3 is expressed only in the testis germ cells (Ivanov, I. et. al., *Proc. Natl. Acad. Sci. USA* 97: 4808-4813 (2000); Tosaka, Y. et. al., *Genes to Cells* 5:265-276 (2000)) where expression begins early in spermiogenesis and finishes in the late spermatid phase. Antizyme production is controlled by a unique regulatory mechanism known as translational frameshifting (Matsufuji; S. et. al., *Cell* 80: 51-60 (1995)). The antizyme gene consists of two overlapping open reading frames (ORFs). The bulk of the coding sequence is encompassed in the second (ORF2) but it does not contain an initiation codon. ORF1 is short but contains two AUG initiation codons. Either one of the initiation codons can be used to initiate translation but normally little full length mRNA is made unless a +1 frameshift occurs just before the ORF1 UGA stop codon enabling translation to continue. Only minute quantities of antizyme are generally present in mammalian tissues.

Polyamines and agmatine have been found to greatly enhance the efficiency of frameshifting (Hayashi, S. et. al., *Trends Biochem. Sci.* 21:27-30 (1996); Satriano, J. et. al., *J. Biol. Chem.* 273:15313-15316 (1998)). Vertebrates possess three elements that control frameshifting, the UGA stop codon in ORF1, a stem-loop structure 3' to the ORF1 UGA that can base pair with a portion of the loop and conserved sequence motifs within the 3' region of ORF1 (Matsufuji, S. et. al., *Cell* 80: 51-60 (1995)). It is unclear how or if polyamines interact directly with these structural elements to induce frameshifting. There may exist unknown mediators that may involve the ribosome.

In one of the first systematic assessments of antizyme induction by polyamine analogs, oligoamines such as octamines, decamines and dodecamines were found to induce antizyme to varying degrees (Mitchell, et al., Antizyme induction by polyamine analogues as a factor of cell growth inhibition, *Biochem. J.*, 2002, 366, 663-671). These levels correlated with the cellular levels of antizyme as measured by Western blotting. A number of compounds such as bisethylnorspermine, bisethylhomospermine and 1,19-bis(ethylamino)-5,10,15-triazanonadecane (BE-4-4-4-4) were found to induce antizyme as well as spermine. However, certain conformational restrictions within the polyamine analogs such as three, four and five-membered rings or triple bonds between the central nitrogens negatively affected antizyme induction. Many of the oligoamines greatly exceeded spermine in their ability to induce antizyme (super-induction) when tested at the same concentration (10 μM). The amount of antizyme frameshifting was found to correlate with the degree of growth inhibition. The oligoamines induced immediate cessation of cell growth, which was speculated to result from the super-induction of frameshifting. However, Mitchell et al also noted that these compounds might have other mechanisms of action leading to their observed cytotoxicity.

A number of putrescine analogs have been found to be potent reversible inhibitors of ODC. For example, 1,4-diamino-trans-2-butene inhibits ODC with a $K_i$ of 2 μM and 1,4-phenylenediamine somewhat less potently inhibits ODC with a $K_i$ of 46 μM (Relyea, N. et. al., *Biochem. Biophys. Res. Comm.* 67:392-402 (1975); Solano, F. et. al., *Int. J. Biochem.* 20:463-470 (1988)).

A number of studies have looked at both transient and inducible overexpression of antizyme in cell lines and animal models. Anti-tumor activity was shown in a study by Iwata and colleagues (Iwata, S. et. al., *Oncogene* 18:165-172 (1999)) using ectopically expressed inducible antizyme. In this study, nude mice were inoculated with H-ras transformed NIH3T3 cells expressing an inducible antizyme vector. Induction of antizyme blocked tumor formation in these mice and induced cell death in vitro. Intracellular polyamine levels were also measured. Both putrescine and spermidine were completely depleted within 12 hours of induction. Spermine was also significantly reduced but over a slower time frame. Some of these observations were verified in another report that used a glucocorticoid (dexamethasone)-inducible promoter to force expression of antizyme in HZ7 cells (Murakami, Y. et. al., *Biochem. J.* 304:183-187 (1994)). Dexamethasone inhibited growth of this cell line, depleted putrescine levels, severely decreased spermidine levels but did not affect spermine levels. Addition of exogenous putrescine restored the intracellular putrescine levels and partially restored spermidine levels. In another study, Tsuji and colleagues (Tsuji, T. et. al., *Oncogene* 20:24-33 (2001)) developed a hamster malignant oral keratinocyte (HCPC-1) cell line that stably expressed antizyme. Ectopic expression of antizyme suppressed tumor mass in nude mice by about 50%. In vitro, ectopic expression significantly increased the doubling time of antizyme transfectants and the antizyme transfectants demonstrated significantly less growth in soft agar. There was also a substantial increase in Gi phase cells with a corresponding decrease in S phase cells. These cells also showed morphological alterations suggesting terminal differentiation. This was accompanied by an increase in demethylation of DNA CCGG sites of 5-methyl cytosines. It was proposed that antizyme mediates a novel mechanism in tumor suppression by reactivating key cellular genes silenced by DNA hypermethylation during cancer development. In yet another example, transgenic mice that overexpress ODC in keratinocytes have been shown to develop a high rate of spontaneous and induced skin cancer (Megosh, L. et. al., *Cancer Res.* 55:4205-4209 (1995)). A reduction in the frequency of induced skin-tumors was observed in the skin of these transgenic mice expressing antizyme (Feith, D. et. al. *Cancer Res.* 61:6073-6081 (2001)). All of these studies suggest that antizyme can reduce or inhibit tumor growth by both depleting polyamines and interfering with cell cycle progression. Examples of antizyme inducing agents can be found in Vermeulen, et al., Antizyme modulators and their use. August 2000, PCT patent WO/0046187; and Burns, M. R. Polyamine analogs that activate antizyme frameshifting, March 2004, US Pat Appl. Pub. 2004/0058954

A mutant L1210 leukemia cell line was shown to have greatly reduced polyamine transport activity following selection for resistance to methylglycoxal bis(guanylhydrazone) (MGBG), a cytotoxic AdoMetDC inhibitor that is taken up by the same transport system as the polyamines. Mice inoculated with these cells had a much greater response to DFMO treatment (87% increase in median survival time; 13 of 40 mice cured) than mice inoculated with the parental cell line (22% increase in median survival time). (Persson et al., Curative effect of d,1-2-difluoromethylornithine on mice bearing mutant L1210 leukemia cells deficient in polyamine uptake, *Cancer Res.* 1988, 48, 4807-4811).

A second experimental approach is based on the fact that the microbial flora in the gastrointestinal tract produces a significant source of extracellular polyamines. (Sarhan et al., The gastrointestinal tract as polyamine source for tumor growth, *Anticancer Res.* 1989, 9, 215-224). When this source of polyamines is removed by antibiotic treatment, DFMO's previously moderate growth inhibitory effects on Lewis lung carcinoma or L1210 cells are markedly potentiated. (Hessels et al., Limitation of dietary polyamines and arginine and the gastrointestinal synthesis of putrescine potentiates the cytostatic effect of α-difluoromethylornithine in L1210 bearing mice, *Int. Symp. Polyamines in Biochemical and Clinical Research*, Sorrento (Italy), 1988, Abstr. P105). Finally, an additional source of polyamines is from the diet. (Bardocz et al., Polyamines in food; implications for growth and health, *J. Biochem Nutr.* 1993, 4, 66-71). By feeding a polyamine-free diet to DFMO-treated nude mice, MCF-7 human breast cancer xenografts contained greatly reduced levels of putrescine in comparison to DFMO treatment alone. (Levêque et al., J-Ph. The gastrointestinal polyamine source depletion enhances DFMO induced polyamine depletion in MCF-7 human breast cancer cells in vivo, *Anticancer Res.* 1998, 18, 2663-2668). In additional animal models, complete polyamine deprivation also enhanced DFMO's growth inhibitory effectiveness. (Moulinoux et al., Inhibition of growth of the U-251 human glioblastoma in nude mice by polyamine deprivation, *Anticancer Res.* 1991, 11, 175-180; Quemener et al., Polyamine deprivation enhances antitumoral efficacy of chemotherapy, *Anticancer Res.* 1992, 12, 1447-1454; and Chamaillard et al., Polyamine deprivation prevents the development of tumour-induced immune suppression, *Br. J. Cancer* 1997, 76, 365-370).

Given the importance of extracellular sources of polyamines to the growth of cells, pharmacological agents that block polyamine transport are desired. A series of simple amino acid/spermine conjugates compounds were designed, synthesized and biologically evaluated and shown to act as potent polyamine transport inhibitors in the MDA-MB-231 human breast cancer cell line. (Burns et al., Amino acid/spermine conjugates: polyamine amides as potent spermidine uptake inhibitors, *J. Med. Chem.* 2001, 44(22), 3632-3644). These compounds were evaluated based on their: 1) ability to inhibit the uptake of radiolabeled spermidine into MDA-MB-231 breast cancer cells; 2) their ability to increase the growth inhibitory effects of DFMO on MDA-MB-231 cells in culture even in the presence of 1 µM extracellular spermidine; 3) their inability to rescue cells from the growth inhibitory effects of DFMO in the absence of extracellular polyamines, and 4) their ability to deplete the intracellular levels of polyamines after combination treatment with DFMO. These compounds have limited cytotoxic properties when used alone, thus increasing the potential of providing tumor selectivity.

Park et.al. explored the mechanism of cell growth inhibition exerted by a series of monoguandino diamines. (Park et al, Antiproliferative effects of inhibitors of deoxyhypusine synthase, *J. Bio. Chem.* 1994, 269 (45), 27827-27832). Their data suggests that their effects are through the inhibition of deoxyhypusine synthase. No effects on the polyamine levels of cells were noted. N¹-guanyl-1,7-diaminoheptane was shown to be the most active and its antiproliferative effects appeared to be reversible.

Additional agents, especially agmatine, are disclosed in WO 2004/078157 A2 to Oblong et al, September, 2004 Regulation of mammalian hair growth.

WO 99/03823 and its corresponding U.S. patent application Ser. No. 09/341,400, filed Jul. 6, 1999, (both of which are herby incorporated in their entireties as if fully set forth) as well as the recent publications of Burns, M. R.; Carlson, C. L.; Vanderwerf, S. M.; Ziemer, J. R.; Weeks, R. S.; Cai, F.; Webb, H. K.; Graminski, G. F. Amino acid/spermine conjugates: polyamine amides as potent spermidine uptake inhibitors, *J. Med. Chem.* 2001, 44, 3632-44 and Graminski, G. F.; Carlson, C. L.; Ziemer, J. R.; Cai, F., Vermeulen, N. M.; Vanerwerf, S. M.; Burns, M. R. synthesis of bis-spermine dimers that are potent polyamine transport inhibitors, *Bioorg. Med. Chem. Lett.* 2002, 12, 35-40 describe some extremely potent polyamine transport inhibitors.

Citation of any reference herein is not intended as an admission that any of the foregoing is pertinent prior art, nor does it constitute any admission as to the contents or date of these documents.

SUMMARY

The present disclosure relates to treating proliferative cutaneous disease states or conditions by administering a polyamine transport inhibitor represented by the formula:

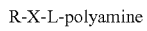

Wherein R is straight or branched C10-50 saturated or unsaturated aliphatic, carboxyalkyl, carbalkoxyalkyl, or alkoxy; a C1-8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; an aryl sulfonyl;

X is —CO—, —SO$_2$—, or —CH$_2$; and

L is a covalent bond or a naturally occurring amino acid, lysine, ornithine, 2,4-diaminobutyric acid;

or pharmaceutically acceptable salts thereof or prodrugs thereof; and a polyamine biosynthesis inhibitor.

The present disclosure is especially related to inhibiting or reducing hair growth by administering a polyamine transport inhibitor represented by the formula disclosed above, and a polyamine biosynthesis inhibitor.

The present disclosure is also especially related to treating a patient suffering from a cutaneous autoimmune disease which comprises administering a polyamine transport inhibitor represented by the formula disclosed above, and a polyamine biosynthesis inhibitor.

Also disclosed is a composition comprising:

a polyamine transport inhibitor represented by the formula:

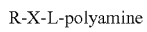

Wherein R is straight or branched C10-50 saturated or unsaturated aliphatic, carboxyalkyl, carbalkoxyalkyl, or alkoxy; a C1-8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; an aryl sulfonyl;

X is —CO—, —SO$_2$—, or —CH$_2$; and

L is a covalent bond or a naturally occurring amino acid, lysine, ornithine, 2,4-diaminobutyric acid;

or pharmaceutically acceptable salts thereof or prodrugs thereof;

and a polyamine biosynthesis inhibitor.

Examples of suitable polyamine biosynthesis inhibitors are ODC inhibitors, spermidine synthase inhibitors, spermine synthase inhibitors, deoxyhypusine synthase inhibitors, inhibitors of ODC enzyme induction and antizyme inducing agents.

BRIEF DESCRIPTION OF THE DRAWINGS

FIG. 4 shows the relationship between the length of the hydrocarbon substituent at the ε-position of the L-lysine analogs and the resulting activity as polyamine transport inhibitors as defined by $EC_{50}$.

FIG. 5 representatively shows the portion of the compounds for calculation of logP values.

BEST AND VARIOUS MODES

Figure 1A:
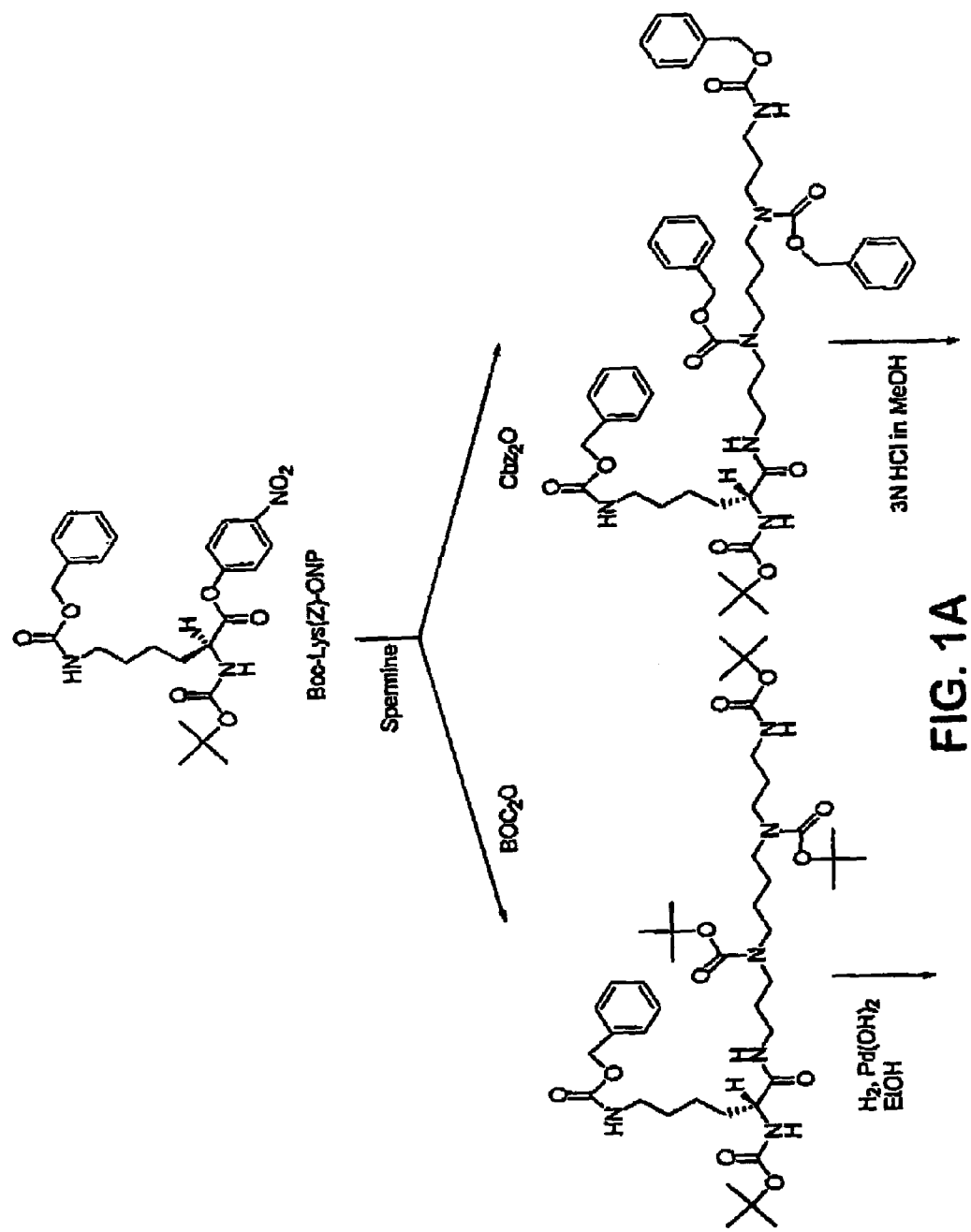
FIG. 1 shows Scheme 1, a pathway for the synthesis of selectively acylated lysine-spermine derivatives. The pathway may be readily adapted for the synthesis of other polyamine derivatives by the use of an analogous protected "NH—X—COO" starting material (wherein X is CH—$(CH_2)_d$—NH—COO—$CH_2$—Ph, wherein d is 0 to 30 and "Ph" is phenyl) and/or the use of any primary polyamine including spermine.

The polyamine transport inhibitors employed according to the present disclosure include those encompassed by the following formula I:

R-X-L-polyamine

Wherein R is selected from H or from the group of a straight or branched C1-50 saturated or unsaturated aliphatic, carboxyalkyl, carbalkoxyalkyl, or alkoxy; a C1-8 alicyclic; a single or multiring aryl substituted aliphatic; an aliphatic-substituted single or multiring aromatic; a single or multiring heterocyclic; a single or multiring heterocyclic aliphatic; a C1-10 alkyl; an aryl sulfonyl; or cyano;

"X" may be —CO—, or —$SO_2$—, or —$CH_2$—,

L is a covalent bond or a naturally occurring amino acid, lysine, ornithine, 2,4-diaminobutyric acid; and "polyamine" may be any naturally occurring, such as putrescine, spermine or spermidine, or synthetically produced polyamine.

Typically, R is at least about C5, at least about C10, at least about C11, at least about C12, at least about C13, at least about C14, at least about C15, at least about C16, at least about C17, at least about C18, at least about C19, at least about C20, or at least about C22.

The linkage between X and the polyamine may be direct, wherein there are no atoms between X and the nitrogen of the amine group of the polyamine, or indirect, where there may be one or more atoms between X and the nitrogen of the amine group of the polyamine. The linkage between X and the polyamine may occur via any amino group within the polyamine, although a primary amino group is used in more typical embodiments of this disclosure.

In those embodiments where the linkage between X and the polyamine is indirect, the intervening one or more atoms are typically those of an amino acid or a derivative thereof. In more typical embodiments of this type, the intervening one or more atoms are those of lysine, aspartic acid, glutamic acid, ornithine, or 2,4-diaminobutyric acid. Typical compounds of this type may be represented as:

R-X-L-polyamine

Wherein R is straight or branched C10-50 saturated or unsaturated aliphatic, carboxyalkyl, carbalkoxyalkyl, or alkoxy; a C1-8 alicyclic; a single or multiring aryl substituted or unsubstituted aliphatic; an aliphatic-substituted or unsubstituted single or multiring aromatic; a single or multiring heterocyclic; a single or multiring heterocyclic aliphatic; an aryl sulfonyl;

"X" may be —CO—, or —$SO_2$—, or —$CH_2$—, and

L is a covalent bond or a naturally occurring amino acid, lysine, ornithine, 2,4-diaminobutyric acid, or derivatives thereof.

The analogs and derivatives may be optionally further substituted at one or more other positions of the polyamine. These include, but are not limited to, internal nitrogen and/or internal carbon atoms. In one aspect, typical substituents are structures that increase polyamine transport inhibition, binding affinity or otherwise enhance the irreversibility of binding of the compound to a polyamine binding molecule, such as the polyamine transporter, an enzyme or DNA. Such additional substituents include the aziridine group and various other aliphatic, aromatic, mixed aliphatic-aromatic, or heterocyclic multi-ring structures. Reactive moieties which, like aziridine, bind covalently to a polyamine transporter or another polyamine binding molecule, are also within the scope of this disclosure. Examples of reactive groups that react with nucleophiles to form covalent bonds include chloro-, bromo- and iodoacetamides, sulfonylfluorides, esters, nitrogen mustards, etc. Such reactive moieties are used for affinity labeling in a diagnostic or research context, and may contribute to pharmacological activity in inhibiting polyamine transport or polyamine synthesis. The reactive group can be a reactive photoaffinity group such as an azido or benzophenone group. Chemical agents for photoaffinity labeling are well-known in the art (Flemming, S. A., *Tetrahedron* 1995, 51, 12479-12520).

One class of a polyamine analog or derivative of the disclosure that binds to a polyamine-binding site of a molecule and/or inhibits polyamine transport, is described by the following formula II:

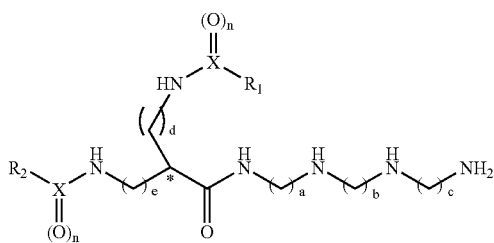

wherein a, b, and c independently range from 1 to 10; d and e independently range from 0 to 30; each X is independently either a carbon (C) or sulfur (S) atom, and $R_1$ and $R_2$ are as described below, or each of $R_1X\{O\}_{n-}$ and $R_2X\{O\}_{n-}$ are independently replaced by H; and * denotes a chiral carbon position. Where if X is C, then n is 1; if X is S then n is 2; and if X is C, then the XO group may be $CH_2$ such that n is 0.

In the above formula, $R_1$ and $R_2$ are independently selected from H or from the group of a straight or branched C1-50 saturated or unsaturated aliphatic, carboxyalkyl, carbalkoxyalkyl, or alkoxy; a C1-8 alicyclic; a single or multiring aryl substituted aliphatic; an aliphatic-substituted single or multiring aromatic; a single or multiring aromatic or saturated heterocyclic; a single or multiring heterocyclic aliphatic; a C1-10 alkyl; and aryl sulfonyl; or cyano.

Examples of heterocyclic rings as used herein include, but are not limited to, pyrrole, furan, thiophene, imidazole, oxazole, thiazole, pyrazole, 3-pyrroline, pyrrolidine, pyridine, pyrimidine, purine, quinoline, isoquinoline, and carbazole.

All of the above described aliphatic carboxyalkyl, carbalkoxyalkyl, alkoxy, alicyclic, aryl, aromatic, and heterocyclic moieties may, of course, also be optionally substituted with 1-3 substituents independently selected from halo (fluoro, chloro, bromo or iodo), lower alkyl (1-6C) and lower alkoxy (1-6C).

As used herein, carboxyalkyl refers to the substituents —R'—COOH wherein R' is alkylene; and carbalkoxyalkyl refers to —R'—COOR wherein R' and R are alkylene and alkyl respectively. In preferred embodiments, alkyl refers to a saturated straight- or branched-chain hydrocarbyl radical of 1-6 carbon atoms such as methyl, ethyl, n-propyl, isopropyl, n-butyl, t-butyl, n-pentyl, 2-methylpentyl, n-hexyl, and so forth. Alkylene is the same as alkyl except that the group is divalent. Aryl or alkyl sulfonyl moieties have the formula —$SO_2R$, and alkoxy moieties have the formula —O—R, wherein R is alkyl, as defined above, or is aryl wherein aryl is phenyl, optionally substituted with 1-3 substituents independently selected from halo (fluoro, chloro, bromo or iodo), lower alkyl (1-6C) and lower alkoxy (1-6C).

A particular group of compounds encompassed by the above is where d is 4 and e is 0.

An additional class of a polyamine analog or derivative of the disclosure that binds to a polyamine-binding site of a molecule and/or inhibits polyamine transport, is described by the following formula III:

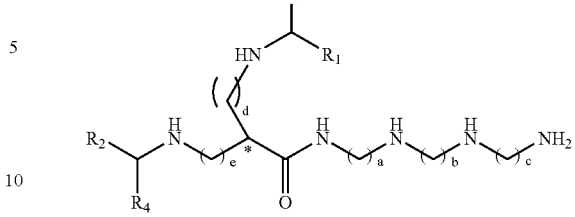

wherein a, b, and c independently range from 1 to 10 and d and e independently range from 0 to 30. $R_1$ and $R_2$ are defined as above for formula II and $R_3$ and $R_4$ are independently selected from organic substituents including —$CH_3$ and as defined above for $R_1$ and $R_2$ in formula II above. This grouping of analogs is produced by reductive amination of the free amino precursor with a ketone. Some members of this group of analogs are shown in Series V (see FIG. 2).

In one particular embodiment of the invention $R_1$ and $R_2$ are identical and as described for formula II. Positions $R_3$ and $R_4$ may also be identical, and all of $R_1$ through $R_4$ may also be identical. Additionally, each of positions $R_1$, $R_2$, $R_3$ and $R_4$ in formula III may also be independently H.

In an additional aspect of the disclosure, the proximal and/or the distal amino group relative to the polyamine (such as spermine) can be di-alkylated to form tertiary amines. These materials can be synthesized by reductive amination with a large excess of the carbonyl component. Additionally, these materials may be produced by a conjugate addition of the amine precursor to an α,β-unsaturated nitrile. Each of $R_1$, $R_2$, $R_3$ and $R_4$ can be independently varied and are as defined as above for formula III. Each of $R_1$, $R_2$, $R_3$ and $R_4$ may also be independently H. The values of a, b, c, d and e are as described above for formula III. This aspect of the invention is depicted in the following formula IV:

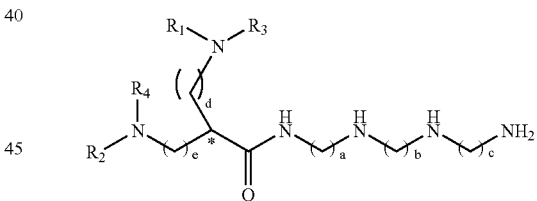

In a further aspect of the disclosure, compounds which lack the proximal or distal amino group on the acyl portion of the molecule are also provided. These are represented by formula V:

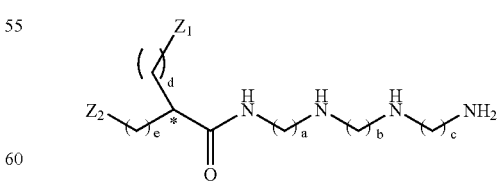

where $Z_1$ is $NR_1R_3$ and $Z_2$ is selected from —$R_1$, —$CHR_1R_2$ or —$CR_1R_2R_3$ (wherein $R_1$, $R_2$, and $R_3$ are as defined above for formula III) or $Z_2$ is $NR_2R_4$ and $Z_1$ is selected from —$R_1$, —$CHR_1R_2$ or —$CR_1R_2R_3$ (wherein $R_1$, $R_2$, and $R_3$ are as defined above for formula III). Values for a, b, and c independently range from 1 to 10; d and e independently range from 0 to 30. Compounds encompassed by formula V maybe prepared by first coupling amino acid derivatives (modified to contain the non-amine containing Z group) to a polyamine followed by appropriate derivatization of the amine containing Z group. Chemistries for such reactions are known in the art and disclosed herein.

In particular embodiments of the disclosure, positions $R_1$, $R_2$, $R_3$ and $R_4$ of all the formulas set forth above are independently selected from the following, where each of g, h, I, j, and k are independently selected from 0 to 15:

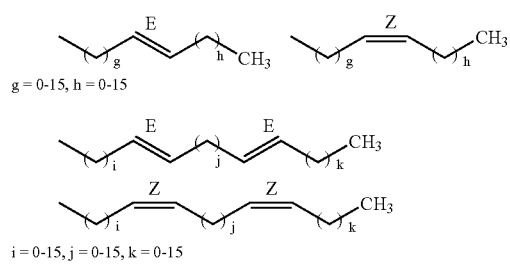

wherein E refers to "entgegen" and Z refers to "zusammen".

The present disclosure includes the free base or acid forms, as well as salts thereof, of the polyamine analogs and derivative described by the above formulas. The disclosure also includes the optical isomers of the above described analogs and derivatives, especially those resulting from the chiral center indicated above with a*. In a further embodiment of mixtures of enantiomers and/or diastereoisomers, resulting from a single preparative step, combination, or interconversion are encompassed.

The disclosure also provides prodrug forms of the above described analogs and derivatives, wherein the prodrug is metabolized in vivo to produce an analog or derivative as set forth above. Indeed, some of the above described analogs or derivatives may be a prodrug for another analog or derivative.

Pharmaceutically acceptable salts of the compounds employed according to the present disclosure include those derived from pharmaceutically acceptable inorganic or organic acids. Examples of suitable acids include hydrochloric, hydrobromic, sulfuric, nitric, perchloric, fumaric, maleic, phosphoric, glycollic, lactic, salicyclic, succinic, toluene-p-sulfonic, tartaric, acetic, citric methanesulfonic, formic, benzoic, malonic, naphthalene-2-sulfonic, trifluoroacetic and benzenesulfonic acids. Salts derived from appropriate bases include alkali such as sodium and ammonia.

Prodrug forms of the compounds bearing various nitrogen functions (amino, hydroxyamino, amide, etc). may include the following types of derivatives where each R group individually may be hydrogen, substituted or unsubstituted alkyl, aryl, alkenyl, alkynyl, heterocycle, alkylaryl, aralkyl, arakenyl, aralkynl, cycloalkyl or cycloalkenyl groups as defined earlier.

(a) Carboxamides, —NHC(O)R (b) Carbamates, —NHC(O)OR (c) (Acyloxy)alkyl Carbamates, NHC(O)OROC(O)R (d) Enamines, —NHCR(=CHCO$_2$R) or —NHCR(=CHCONR$_2$)

(e) Schiff Bases, —N=CR$_2$ (f) Mannich Bases (from carboximide compounds), RCONHCH$_2$NR$_2$ Preparations of such prodrug derivatives are discussed in various literature sources (examples are: Alexander et al., J. Med. Chem. 1988, 31, 318; Aligas-Martin et al., PCT WO pp/41531, p. 30). The nitrogen function converted in preparing these derivatives is one (or more) of the nitrogen atoms of a compounds of the invention.

It is of course understood that the compounds used according to the present disclosure relate to all optical isomers and stereo-isomers at the various possible atoms of the molecule.

As used herein, the term "polyamine" includes putrescine, spermine or spermidine, as well as longer linear polyamines, branched polyamines, and the like, which may have between 2 and about 10 nitrogens. Also included in this definition are polyamine derivatives or analogs comprising a basic polyamine chain with any of a number of functional groups bound to a C atom or a terminal or internal N atom. For modification at a primary amino group, a polyamine must of course, contain such a group.

Polyamine "analogs" and/or "derivatives" generally refer to any modified polyamine molecule disclosed or described herein. These molecules are generally modifications of existing polyamines, whether naturally occurring or synthetically produced, and may also be referred to as "polyamine agents", "PA" or "agents" of the disclosure. The scope of this definition includes any modification to produce a PA from an existing polyamine or the isolation of a structurally identical PA from a naturally occurring source. Especially the modification is the addition of one or more chemical moieties to the polyamine.

The PAs used according to this disclosure generally have an acylated primary amine functionality and are expected to bind to a cell's polyamine transporter apparatus with a very high affinity. Measurements of $K_i$ were determined by using an assay that shows the inhibition of polyamine uptake, such as uptake of $^3$H-spermidine.

The PAs were also analyzed with a secondary assay to show inhibition of cellular polyamine uptake based on a measurement of cellular growth inhibition in combination with a potent inhibitor of polyamine biosynthesis. This assay was conducted in the presence of polyamines thereby overcoming the polyamine biosynthesis inhibition with DFMO (difluoromethylornithine). Due to the trend that polyamine mono-amides give high potency in both of these assays, it has been inferred, without limiting the disclosure thereto, that there is a site on the transporter protein for tight binding of the inhibitor's amide functionality.

Specific embodiments of these PAs are the result of acylation at a polyamine molecule with two or more primary amine groups. The linkage between the acyl group and the primary amine group is preferably an amide linkage (indicated below as the bond between "CO" and "NH") and the results in a molecule with the following general formula.

rest of acyl group-CO—NH-rest of polyamine

As noted above, other linkages, whether direct or indirect, may also be used. The "polyamine" in the above formula may be any polyamine with at least one primary amine group, but more typically with two or more primary groups, for linkage to the acyl group.

One particular class of acyl groups for inclusion in the above formula contains two primary amines for further acylation. The resultant class of PAs may be described by the following formula (formula II).

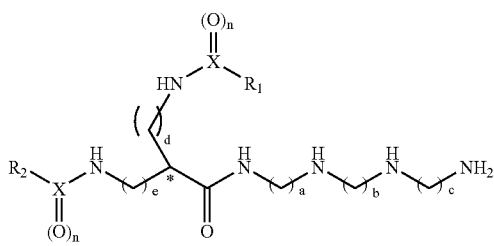

as defined above. Non-limiting examples of alkyl moieties as present in these compounds include straight or branched chains of at least about 8 carbon atoms for increased hydrophobicity (or lipophilicity), such as least about 10, at least about 12, at least about 14, at least about 16, at least about 18, at least about 20, at least about 22, at least about 24, at least about 26, at least about 28, and at least about 30. In yet another set of embodiments, the chain is of at least about 19, 21, 23, 25, or 27 carbon atoms, with at least about 20 to at least about 24 or 26 as even more typical.

A particularly typical group of PAs encompassed by the above formula where d is 4 and e is 0, although generally excluded from this group are PAs where $R_2X\{O\}_{n\text{-}}$ is an H and $R_1X\{O\}_{n\text{-}}$ is $R_1SO_2$— wherein $R_1$ is a thiophene moiety linked to the S atom via the 2 position, and substituted at the 5 position, of the thiophene. Preferably excluded are such PAs wherein the substitution at the 5 position, of the thiophene. Preferably excluded are such PAs wherein the amide linkage is attached to a chlorinated aromatic group, such as the compound identified as ORI 1340 in U.S. patent application Ser. No. 09/396,523, filed Sep. 15, 1999.

Other classes of PAs used according to this disclosure are set forth as formulas I, III, IV, and V as described above. In all of the formulas, the term "single or multiring alicyclic" includes adamantyl type structures. Moreover, the term "substituted" used in conjunction with the description of any chemical moiety for a formula of the invention includes the attachment of the moiety to the rest of the formulas by way of the "substitution". The term also indicates that "unsubstituted" forms of the described chemical moiety is also within the scope of this disclosure.

By analyzing the relationship between a polyamine analog's structure and its ability to act as a polyamine transport inhibitor, it was discovered that increases in the lipophilic character of the hydrophobic substituent on the polyamine may increase transport inhibition. While the nature of the interaction between a lipophilic polyamine analog and the polyamine transport apparatus remains unclear at this time, the disclosure includes, but is not limited to, situations where the hydrophobic (lipophilic) moiety may serve as an anchor to some hydrophobic pocket on the transporter or in a region nearby. This may result in the interaction of the polyamine portion of the analog with the polyamine transporter.

There are a number of ways one might analyze the hydrophobic character of compounds used according to this present disclosure. The following two scales describe ways to measure relative degrees of lipophilicity.

The logP coefficient is the logarithm of the ratio of distribution of a compound in a mixture of 1-octanol and $H_2O$. Compounds with logP values greater than 1 are considered lipophilic (greater solubility in 1-octanol versus $H_2O$). The presence of ionizable groups in the compound has a dramatic effect on this parameter. Ionization will greatly increase a compound's $H_2O$ solubility. For this reason, a compound's ionization potential must be taken into consideration when correlating lipophilicity with activity. One can use a variety of computerized protocols to perform calculated estimates of the logP value. One such computer program is ChemDraw Pro Version 5.0 from CambridgeSoftCorporation. One of the several methods that this program uses to calculate the logP coefficient is through Crippen's fragmentation method (Crippen et. al., *J. Chem. Inf. Comput. Sci.* 1987, 27, 21). This method was used to calculate logP values for fragments of the described molecules. These fragments were generated in the fashion depicted in FIG. 5. The results of these calculations are provided in Table 5 for the D-stereoisomers of the ε-acyl substituted Lys-spm conjugates (FIG. 2, Series I) and in Table 6 for the D-stereoisomers of the ε-alkyl substituted Lys-spm conjugates (FIG. 2, Series IV and V).

TABLE 5

Figure 2A:
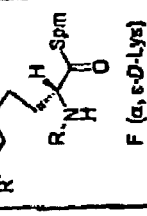
FIG. 2 illustrates exemplary polyamine structures employed according to this disclosure. They have been divided into Series I-VI based upon the character of the chemical moiety attached to a spermine backbone to produce exemplary analogs and derivatives of the invention. Other polyamines may also be used as the backbone. The structures depicted in the first, left-most column of each table represent the specific chemical starting materials utilized in the synthesis of individual polyamine structures. The synthetic steps used result in the end products that are carboxamides from a reaction between an acyl chloride and an amine (series I), sulfonamides from the reaction between a sulfonyl chloride and an amine (series II), carboxamides from the reaction of a DCC, HBTU or PyBOP activated carboxylic acid and an amine (series III), alkylated secondary amines from the reductive amination of the amine with an aldehyde (series IV), alkylated secondary amines with α-alkyl substituents from the reductive amination of the free amino precursor with a ketone (Series V) and di-alkylate tertiary amine products by reductive amination with a large excess of a carbonyl containing (e.g. aldehyde or ketone) component (Series VI). Additionally the Series VI compounds may also be produced by a conjugate addition of the amine precursor of an α,β-unsaturated carbonyl or a α,β-unsaturated nitrile. Columns E and F are directed to doubly derivatized forms of the base chemical structure.
Figure 2F:
Figure 21:
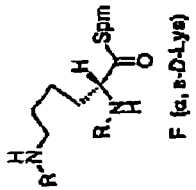
Figure 3A:
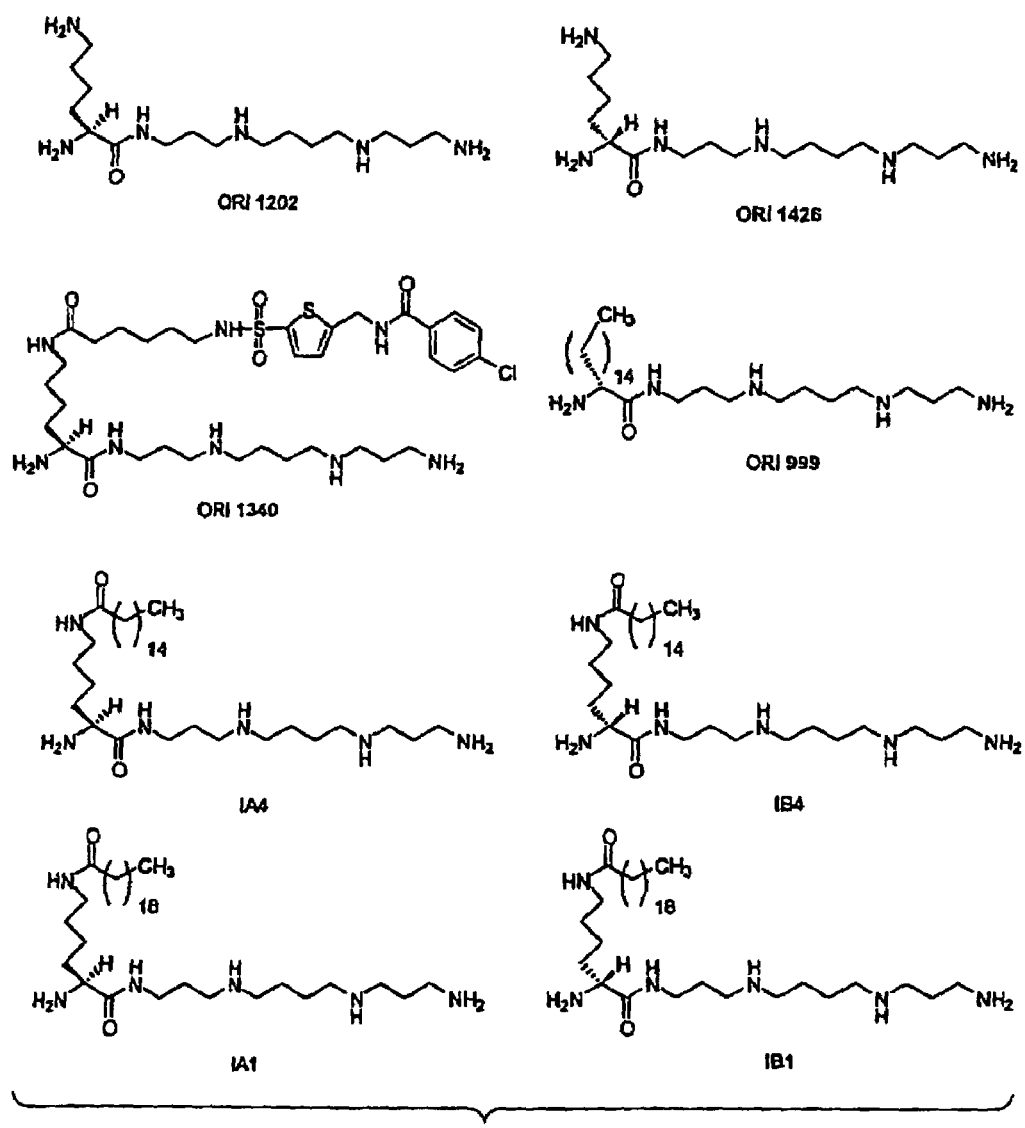
FIGS. 3A to 3B show representative structures of polyamine analogs that can be used according to the present disclosure.
Figure 3B:
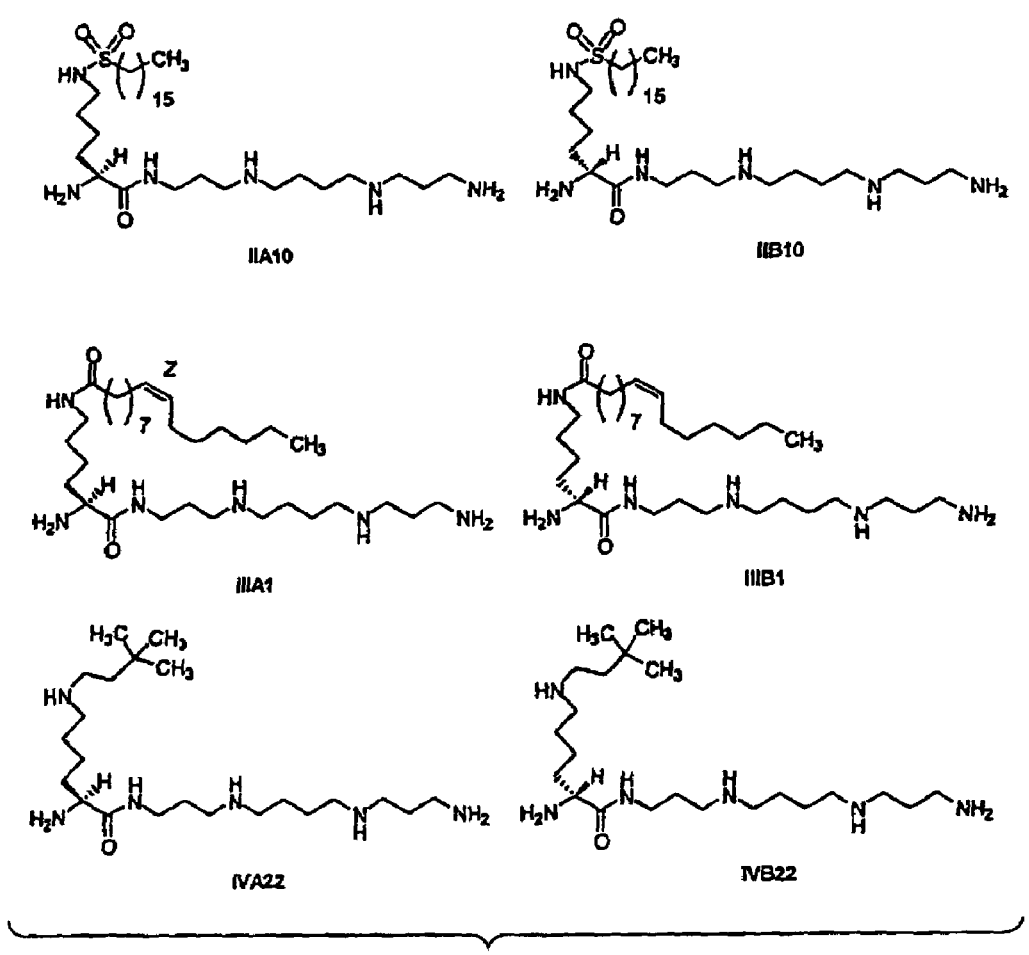

Chemical structure (with ID relative to FIG. 2), logP Calculations, HPLC data and average $EC_{50}$ values for D-stereoisomers of ε-acyl-substituted spermine based analogs (FIG. 2, Series I). Compound 1426 and one Series V compound are included for comparison.

| ID | Structure | LogP | Ret Time-Std | Ave $EC_{50}$ value |
|---|---|---|---|---|
| IB38 | 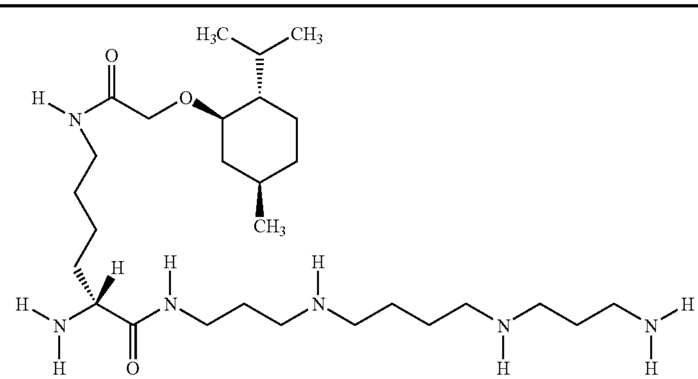 | 1.73 | 9.63 | 13 |

TABLE 5-continued
Chemical structure (with ID relative to FIG. 2), logP Calculations, HPLC data
and average $EC_{50}$ values for D-stereoisomers of ε-acyl-substituted spermine based analogs
(FIG. 2, Series I). Compound 1426 and one Series V compound are included for
comparison.
| ID | Structure | LogP | Ret Time-Std | Ave $EC_{50}$ value |
|---|---|---|---|---|
| IB37 | 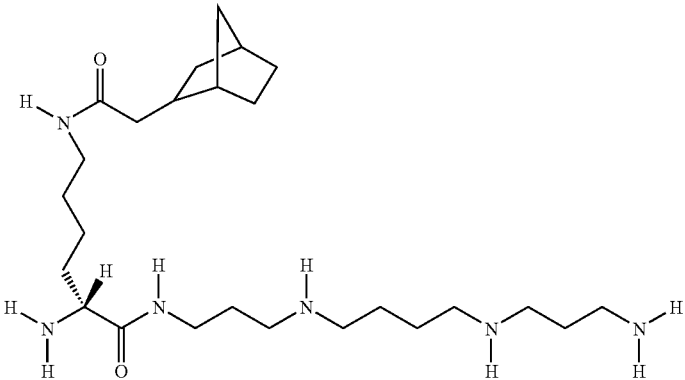 | 1.03 | 6.33 | 41 |
| IB2 | 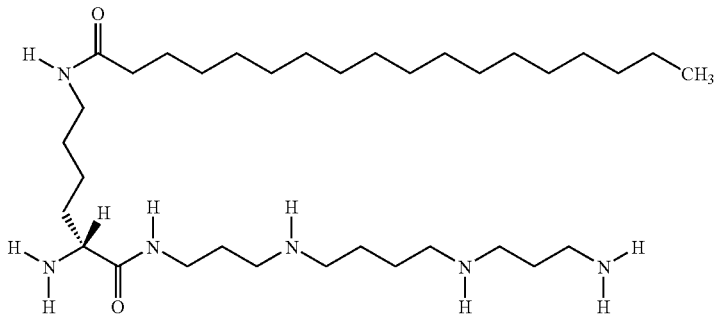 | 6.59 | 21.1 | 0.083 |
| IB4 | 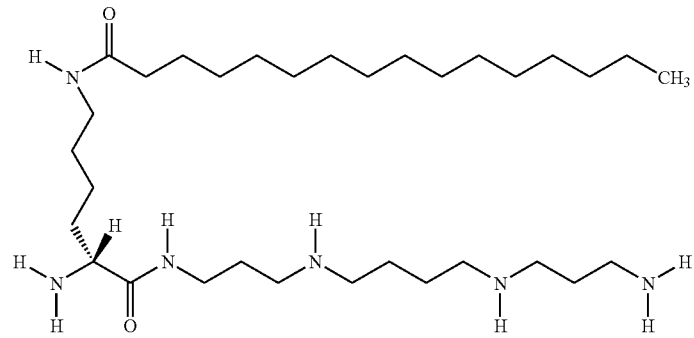 | 5.68 | 15.82 | 0.084 |
| IB8 | 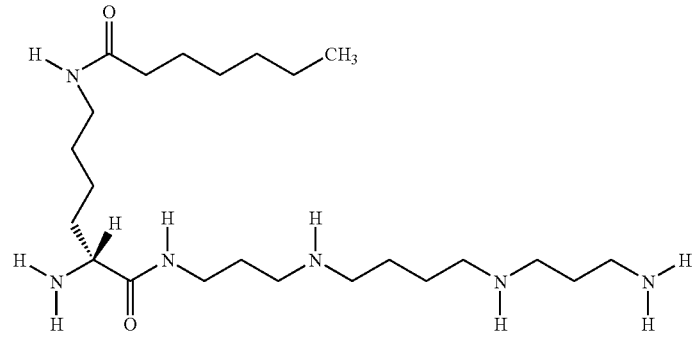 | 1.57 | 6.07 | 3.5 |

TABLE 5-continued

Chemical structure (with ID relative to FIG. 2), logP Calculations, HPLC data
and average EC$_{50}$ values for D-stereoisomers of ε-acyl-substituted spermine based analogs
(FIG. 2, Series I). Compound 1426 and one Series V compound are included for
comparison.

| ID | Structure | LogP | Ret Time-Std | Ave EC$_{50}$ value |
|---|---|---|---|---|
| IB26 | 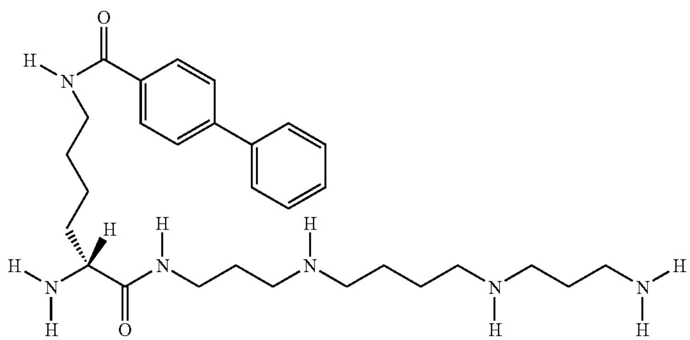 | 2.01 | 6.34 | 1.1 |
| IB36 | 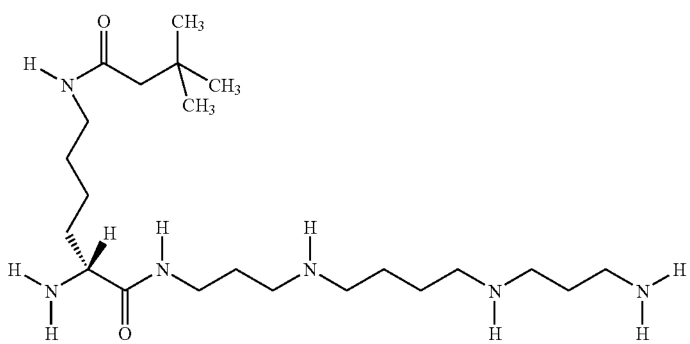 | 1.21 | 4.91 | 27 |
| IB34 | 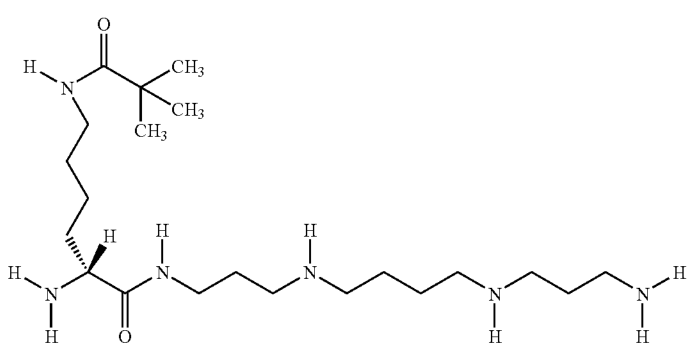 | 0.75 | 4.6 | 8.5 |
| IB6 | 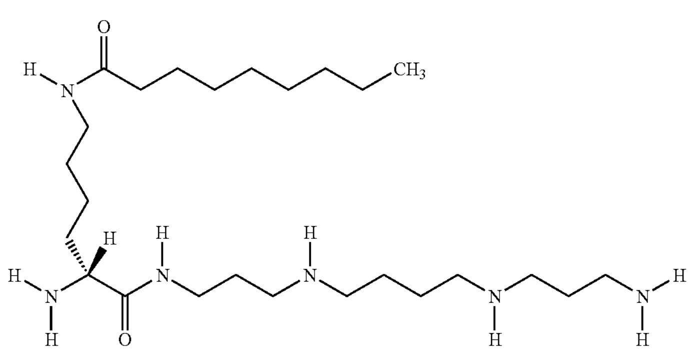 | 2.48 | 10.48 | 2.2 |

TABLE 5-continued

Chemical structure (with ID relative to FIG. 2), logP Calculations, HPLC data and average EC$_{50}$ values for D-stereoisomers of ε-acyl-substituted spermine based analogs (FIG. 2, Series I). Compound 1426 and one Series V compound are included for comparison.

| ID | Structure | LogP | Ret Time-Std | Ave EC$_{50}$ value |
|---|---|---|---|---|
| IB7 | 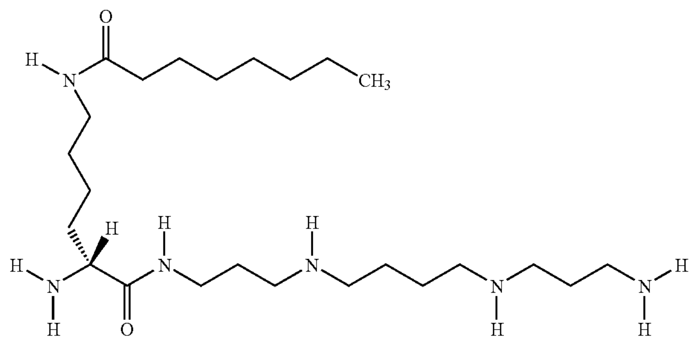 | 2.03 | 6.83 | 13 |
| IB9 | 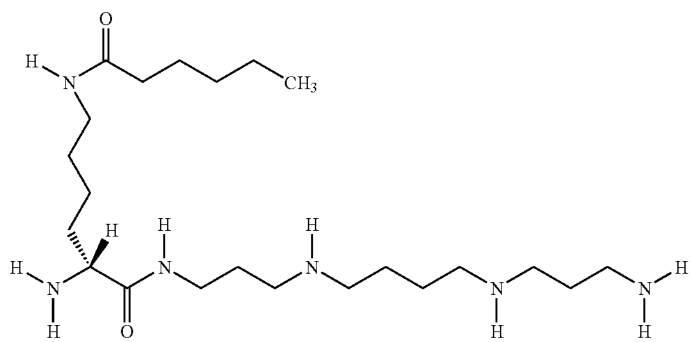 | 1.12 | 5.16 | 12 |
| IB33 | 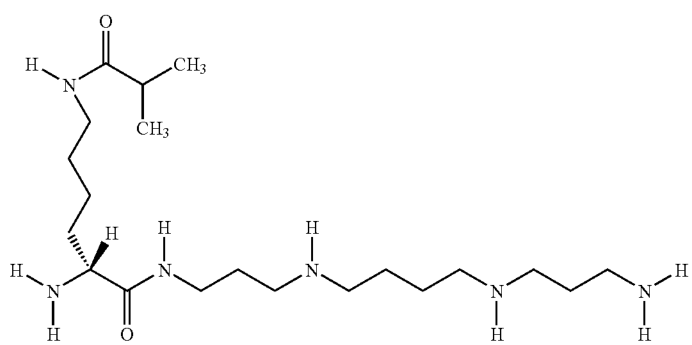 | −0.05 | 3.56 | 8.4 |
| IB10 | 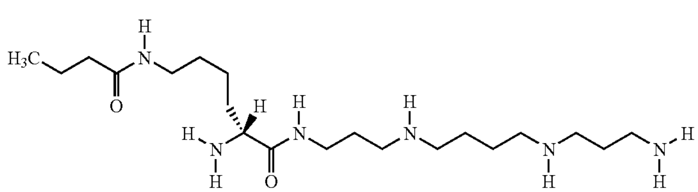 | 0.2 | 3.46 | 12 |
| IB32 | 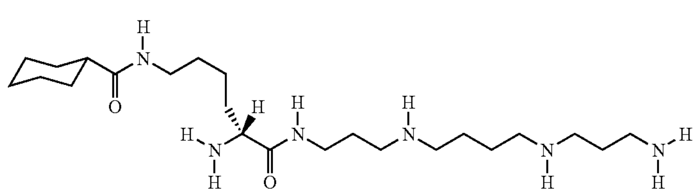 | 0.97 | 5.29 | 3.6 |

TABLE 5-continued

Chemical structure (with ID relative to FIG. 2), logP Calculations, HPLC data and average $EC_{50}$ values for D-stereoisomers of ε-acyl-substituted spermine based analogs (FIG. 2, Series I). Compound 1426 and one Series V compound are included for comparison.

| ID | Structure | LogP | Ret Time-Std | Ave $EC_{50}$ value |
|---|---|---|---|---|
| IB30 | 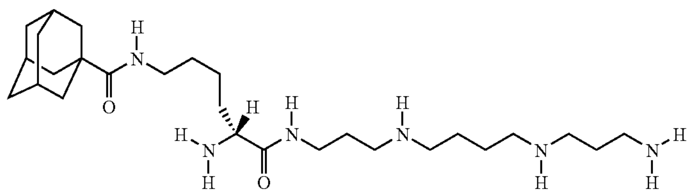 | 1.68 | 7.4 | 2 |
| IB29 | 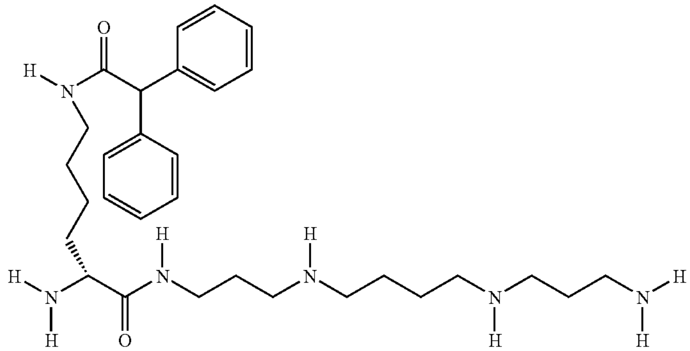 | 1.99 | 6.08 | 2.1 |
| IB25 | 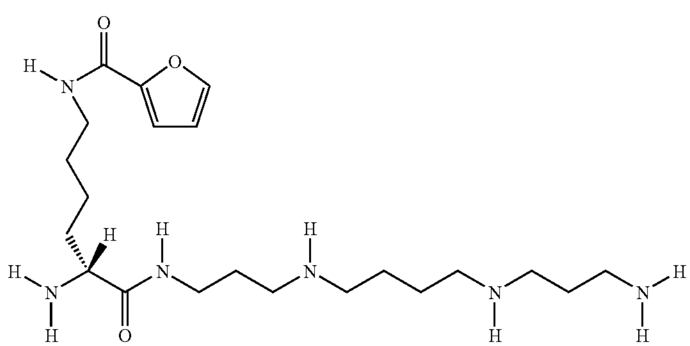 | −0.44 | No Data | 10 |
| IB24 | 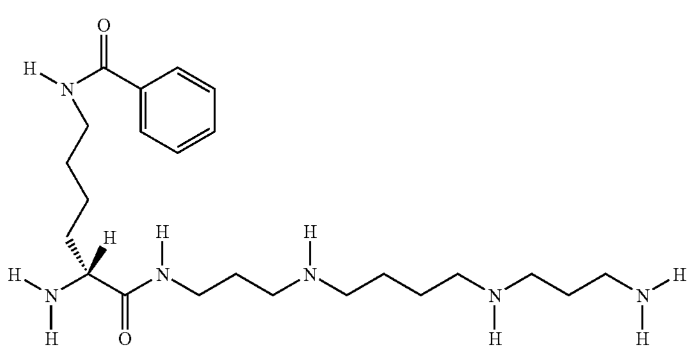 | 0.58 | 4.23 | 30 |
| VA21 | 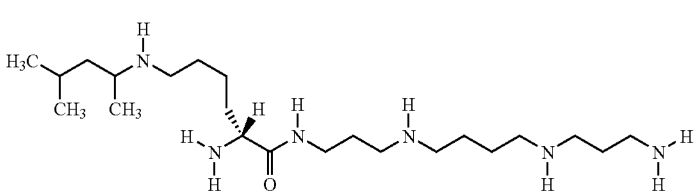 | 1.04 | 10.11 | 0.65 |

TABLE 5-continued

Chemical structure (with ID relative to FIG. 2), logP Calculations, HPLC data and average $EC_{50}$ values for D-stereoisomers of ε-acyl-substituted spermine based analogs (FIG. 2, Series I). Compound 1426 and one Series V compound are included for comparison.

| ID | Structure | LogP | Ret Time-Std | Ave $EC_{50}$ value |
| --- | --- | --- | --- | --- |
| 1426 | 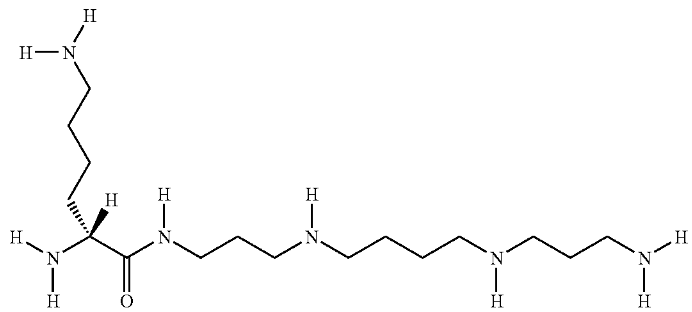 | Not calc'd | 6.68 | 3.7 |
| 1A4 | 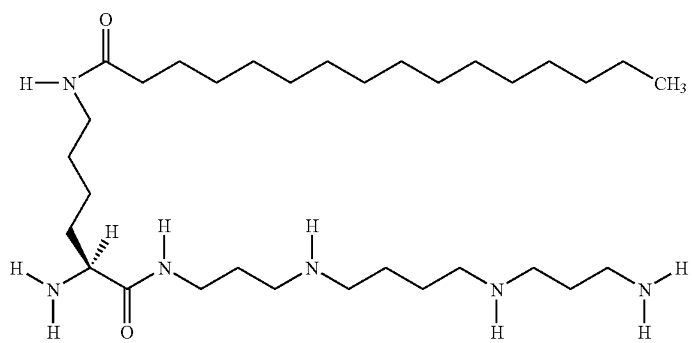 | 5.68 | 15.79 | 0.13 |

Particular PAs used according to this disclosure with respect to Series I type compounds are those with low $EC_{50}$ values, such as those with below about 5, about 6, about 7, about 8, about 9, about 10, about 15, about 20 or about 25 minute HPLC retention times.

TABLE 6

Chemical structure (with ID relative to FIG. 2), calculated logP value, HPLC retention time, and average $EC_{50}$ value for ε-alkylated spermine based analogs (FIG. 2, Series IV and V). Compound 1426 and one Series I compound are included for comparison.

| ID | Structure | LogP | Ret Time-Std | Ave $EC_{50}$ Value |
| --- | --- | --- | --- | --- |
| VB28 | 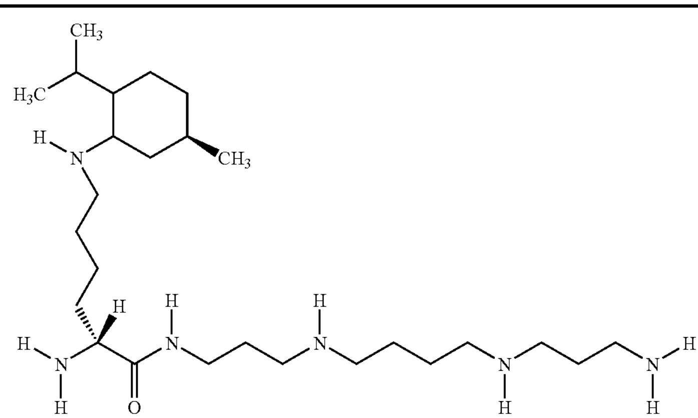 | 2.01 | 13.89 | 1.45 |

TABLE 6-continued

Chemical structure (with ID relative to FIG. 2), calculated logP value, HPLC retention time, and average $EC_{50}$ value for ε-alkylated spermine based analogs (FIG. 2, Series IV and V). Compound 1426 and one Series I compound are included for comparison.

| ID | Structure | LogP | Ret Time-Std | Ave $EC_{50}$ Value |
|---|---|---|---|---|
| IVB28 | 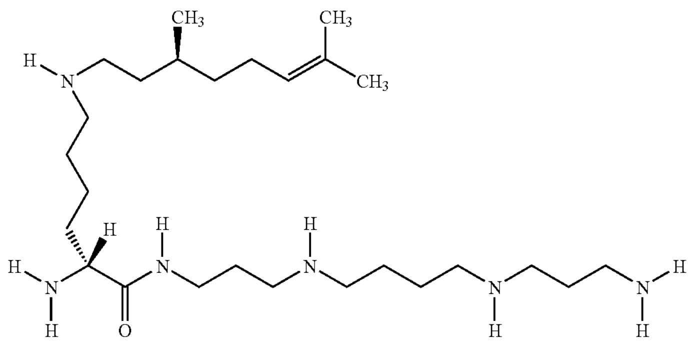 | 2.21 | 9.4 | 12.8 |
| VA22 | 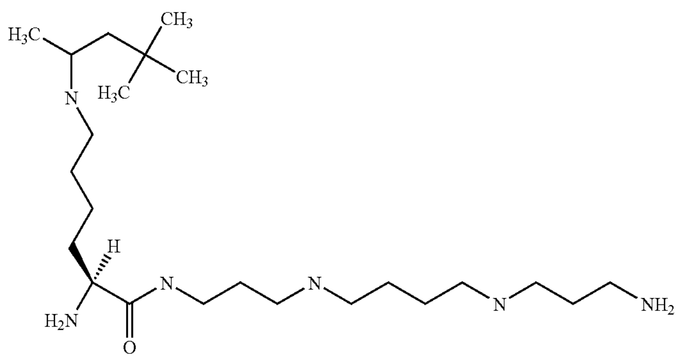 | 1.84 | 10 | 2.42 |
| VA27 | 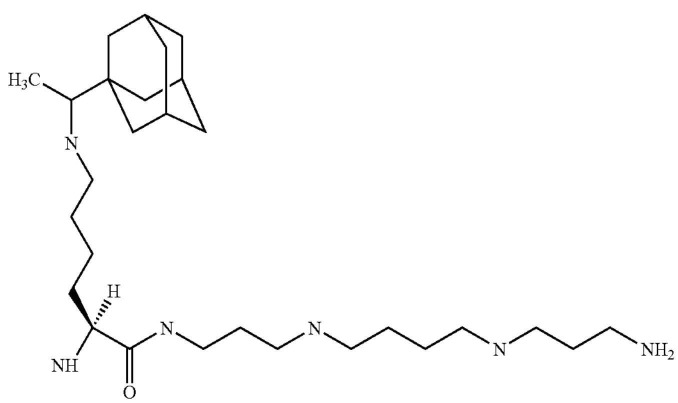 | 2.31 | 12.71 | 26.8 |
| VA26 | 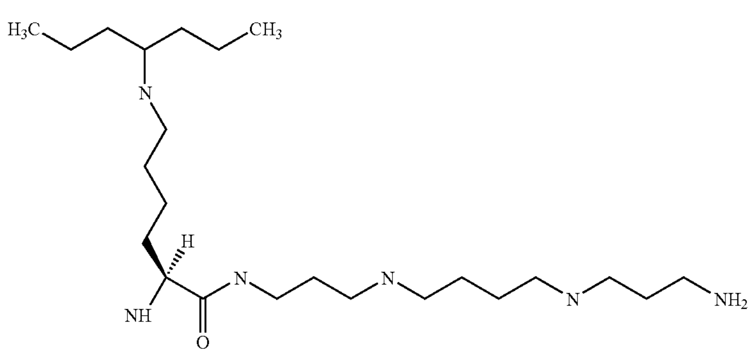 | 1.74 | 10.84 | 4.14 |

TABLE 6-continued

Chemical structure (with ID relative to FIG. 2), calculated logP value, HPLC retention time, and average EC$_{50}$ value for ε-alkylated spermine based analogs (FIG. 2, Series IV and V). Compound 1426 and one Series I compound are included for comparison.

| ID | Structure | LogP | Ret Time-Std | Ave EC$_{50}$ Value |
|---|---|---|---|---|
| IVB23 | 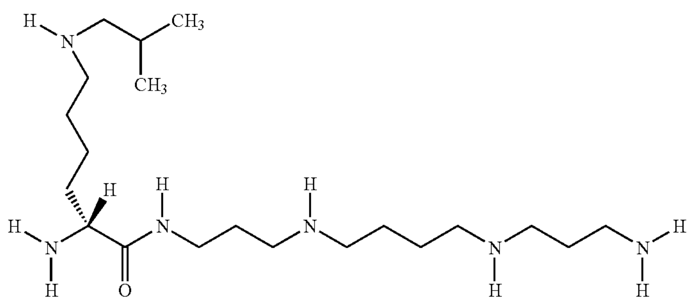 | 0.66 | 9.05 | 1.79 |
| IVB3 | 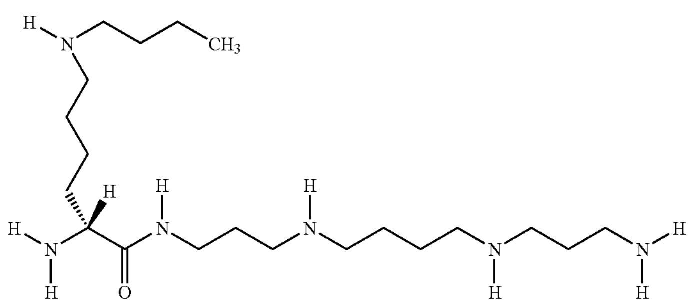 | 0.91 | 9.16 | 2.19 |
| IVB21 | 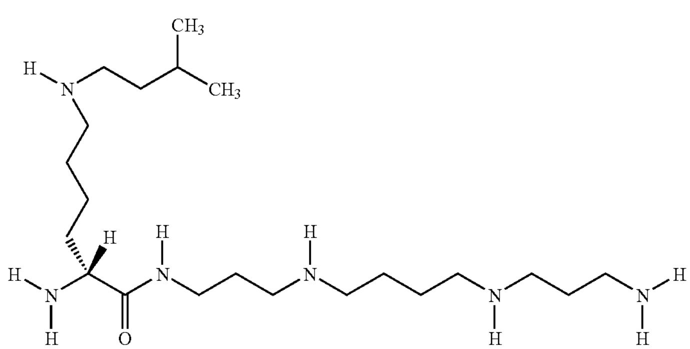 | 1.12 | 9.62 | 1.32 |
| IVB24 | 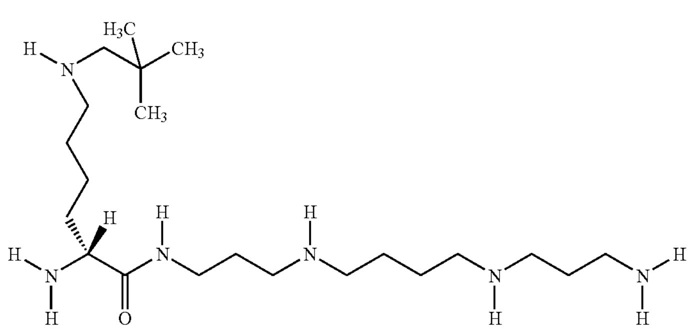 | 1.46 | 9.35 | 1.32 |

TABLE 6-continued

Chemical structure (with ID relative to FIG. 2), calculated logP value, HPLC retention time, and average EC$_{50}$ value for ε-alkylated spermine based analogs (FIG. 2, Series IV and V). Compound 1426 and one Series I compound are included for comparison.

| ID | Structure | LogP | Ret Time-Std | Ave EC$_{50}$ Value |
|---|---|---|---|---|
| IVB22 | 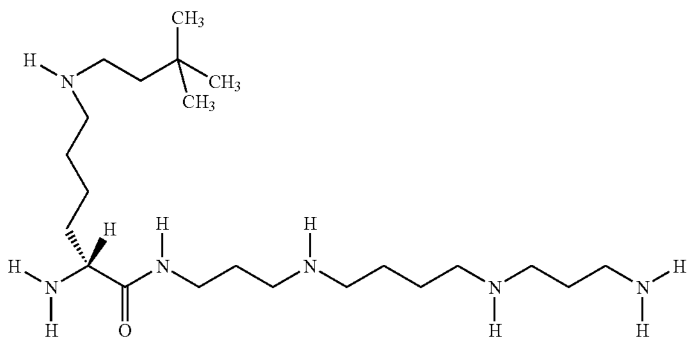 | 1.92 | 9.85 | 0.68 |
| IVB6 | 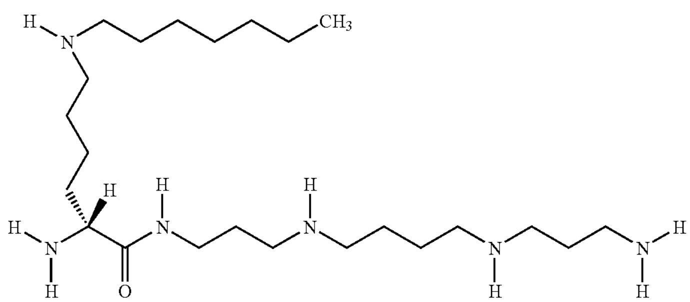 | 2.28 | 10.87 | 0.89 |
| IVB5 | 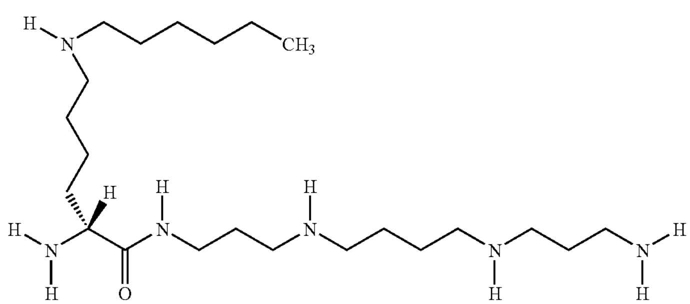 | 1.83 | 10.27 | 0.71 |
| IVB33 | 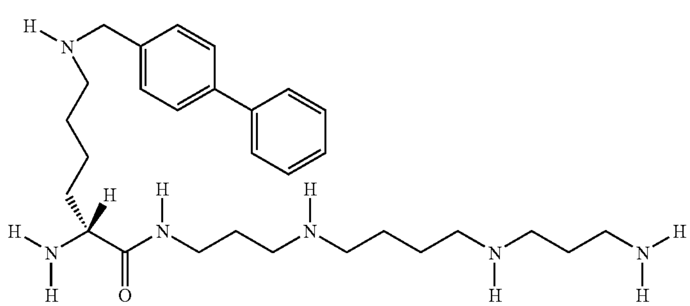 | 2.45 | 10.01 | 1.38 |

TABLE 6-continued

Chemical structure (with ID relative to FIG. 2), calculated logP value, HPLC retention time, and average EC$_{50}$ value for ε-alkylated spermine based analogs (FIG. 2, Series IV and V). Compound 1426 and one Series I compound are included for comparison.

| ID | Structure | LogP | Ret Time-Std | Ave EC$_{50}$ Value |
|---|---|---|---|---|
| IVB27 | 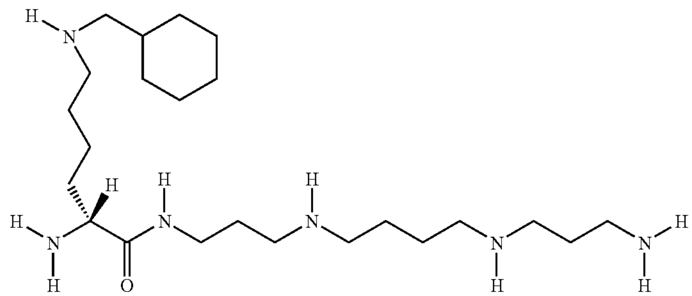 | 1.68 | 10.31 | 0.61 |
| IVB25 | 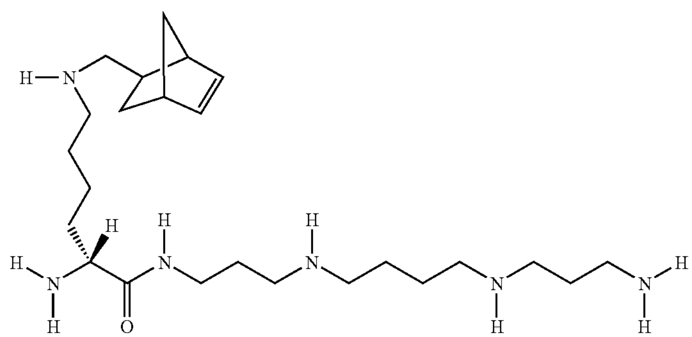 | 0.57 | 9.89 | 0.89 |
| VA21 | 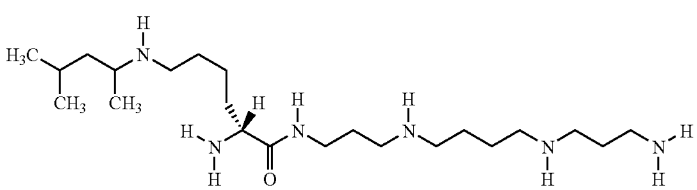 | 1.04 | 10.11 | 0.65 |
| 1426 | 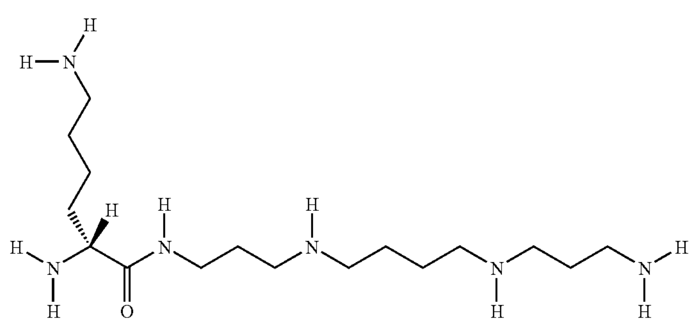 | Not calc'd | 6.68 | 3.68 |

TABLE 6-continued

Chemical structure (with ID relative to FIG. 2), calculated logP value, HPLC retention time, and average EC$_{50}$ value for ε-alkylated spermine based analogs (FIG. 2, Series IV and V). Compound 1426 and one Series I compound are included for comparison.

| ID | Structure | LogP | Ret Time-Std | Ave EC$_{50}$ Value |
|---|---|---|---|---|
| IA4 | [chemical structure] | 5.68 | 15.79 | 0.13 |

Particular PAs used according to this disclosure with respect to Series IV and V type compounds are those with low EC$_{50}$ values, such as those with below about 5, about 6, about 7, about 8, about 9, about 10, about 12, about 14, about 16, about 18, or about 20 minute HPLC retention times.

Another way to measure relative hydrophobicity would be chromatographic techniques such as comparison of HPLC retention times on C18 reverse phase columns, longer retention times would represent greater relative hydrophobicity. A dansylation protocol was utilized to form dansyl derivatives of the described analogs and analyzing these derivatives by fluorescence detection on C18 reverse phase HPLC. The difference between the elution of the peak due to the analog and the peak due to an internal standard (1,7-diaminoheptane) is shown for several representative analogs in Tables 5 and 6 above.

An additional compound hydrophobicity scale, specific for amino acids, was devised and measured by R. Wolfenden (Wolfenden, R.; Andersson, L.; Cullis, P. M.; Southgate, C. C. B. Affinities of amino acid side chains for solvent water. *Biochemistry*, 1981, 20, 849-855). They measured the equilibria of distribution of amino acid side chains between their dilute aqueous solutions and the vapor phase. They describe a scale of "hydration potentials" whereby buffered H$_2$O-vapor phase distribution measurements were made on the side-chain portions of the amino acids (e.g. methane for alanine, methanol for serine, n-butylamine for lysine or n-propylguanidine for arginine). If a side-chain had the potential for ionization a correction was made such that only the un-ionized fraction considered. This was based on calculation of the un-ionized fraction using literature pKa values. The side chains for the twenty naturally occurring amino acids span a range of free energy values for the transfer from the vapor phase to H$_2$O from 2.39 kcal/mol for hydrogen (glycine) or 1.94 kcal/mol for methane (alanine) to −7.00 kcal/mol for n-butylamine (lysine) or −14.6 kcal/mol for n-propylguanidine (arginine).

These values form a "hydration potential" scale, which is correlated with a potential that a given amino acid would be present on the outside, or hydrophilic portion of a protein versus the more hydrophobic interior of a protein. The authors state "that the energetic cost of removing hydrophilic side chains from water is much greater than the cost of pulling hydrophobic side chains into water, and, indeed, it has been observed that hydrophobic residues occur rather often at the surfaces of proteins." This scale could be used to described the lipophilicity of the substituent attached to the polyamine. The polyamine portion is removed before this analysis. As an example, it is also required that the α-amino and α-carboxylate groups of any analogs containing an α-amino acid be removed before analysis. By using this scale, any substituent with a free energy of transfer from the vapor phase of H$_2$O less than that determined for n-butylamine (and thus correlated to lysine) of −7.00 kcal/mol would be expected to be preferred polyamine transport inhibitor in comparison to the lysine-spermine conjugate (ORI 1202). This means any substituent that gives a hydration potential greater (more positive) than −7.00 kcal/mol, as defined in this scale, results in polyamine transport inhibitors with significant activity (values of free energy of transfer which are more negative mean a given compound would have a greater solubility in H$_2$O than the vapor phase).

The particular group of PAs wherein d is 4 and e is 0 includes both the L and D-stereoisomers due to the chiral carbon indicated by * in the above formula. Exemplary PAs such as ORI 1202 (L-Lys-spm), 1426 (D-Lys-spm), and those containing IA4 (FIG. 2) demonstrated potency in both the transporter inhibition and cell growth inhibition assays described below. PA ORI 1202 also displayed effectiveness in several anti-cancer mouse xenograft models. See Weeks, R. S., Vanderwerf, S. M., Carlson, C. L., Burns, M. R., O'Day, C. L., Cai, C. F., Devens, B. H., and Webb, H. K. *Exp. Cell Res.* 2000, 261, 293-302 and Devens, B. H., Weeks, R. S., Burns, M. R., Carlson, C. L., and Brawer, M. K. Prostate Cancer and Prostatic Diseases 2000, 3, 275-279.

Additional modification of the two primary amine groups in the acyl group in the above formula is readily accomplished by the availability of the primary amine groups for selective functionalization together with the commercial availability of orthogonally di-protected versions of H$_2$N(CH$_2$)$_d$CH(NH$_2$)COOH type molecules (where d ranges from 1 to 30 for example), such as lysine or ornithine.

Without being bound by theory, increases in the lipophilicity of the substituent at the above R$_1$ and R$_2$ positions may dramatically increase the affinity for the polyamine transporter. Increases in lipophilicity in the PAs of the invention may improve the inhibition of polyaminc transport due to the presence of both hydrophilic and hydrophobic domains. Biological systems have a significant chemical problem when they attempt to move a very hydrophilic substance, such as polycationic polyamines, across their very hydrophobic outer membrane barriers. If the transporter moves the polyamines in their polycationic forms across this barrier, the transporter may do so via some mechanism for masking or minimizing their hydrophilicity. Mechanisms for this may include the formation of specific salt bridges between the polyamine and negatively charged residues on the protein or formation of a charged interior in the intermembrane pore. Because polyamine transport is known to be an energy dependent process, the transporter may have the task of providing a very specific polyamine shaped hydrophilic pore in the presence of the hydrophobic environment of the membrane. For these reasons the transporter likely has hydrophobic residues for interactions with the membrane in close proximity to hydrophilic residues specific for interactions with the polyamine.

By designing PAs that contain both hydrophobic and hydrophilic domains, the present disclosure exploits the likely characteristics of a polyamine transporter to improve transport inhibition. Thus the present invention provides several series of PAs that contain both a polyamine-mimicking portion and a hydrophobic membrane-mimicking portion. These PAs have been inferred to have great affinity to the transporter, and they show substantially increased growth inhibition (in combination with a polyamine synthesis inhibitor) in comparison to PAs lacking a significantly hydrophobic domain. Probably for very similar reasons, the present PAs are also expected to show improved bioavailability through oral administration. Increases in lipophilicity are expected to enhance absorption after oral uptake.

It is also expected that the introduction of both hydrophilic and hydrophobic domains in the same molecule, as shown by those in the present disclosure, will also enable them to facilitate the transfer of nucleic acids through biological membranes. This property gives the analogs usefulness as transfer agents for anti-sense DNA for a number of scientific, analytical, diagnostic and therapeutic applications.

The above is supported by analysis of the results of extending a straight-chain aliphatic saturated hydrocarbon at position R (see FIG. 2, Series I) results in increases in cell growth inhibition in the presence of a polyamine synthesis inhibitor. The clear trend that longer hydrocarbon chains on this amide position increase potency is indicated by a comparison of spermine based compounds IA4 or IB4 with IB4, IB7, and IB8 (see Tables 5 and 6). FIG. 4 shows the relationship between the length of the hydrocarbon substituent at the R position and the resulting $EC_{50}$ value in the presence of a polyamine synthesis inhibitor.

Tables 5 and 6 show the results from analysis of various exemplary PAs for their ability to inhibit cellular growth in combination with DFMO relative to control cells left untreated. $EC_{50}$ refers to the concentration of PA resulting in 50% of maximum cell growth inhibition in the presence of both DFMO and PA. $K_i$ refers to the inhibition constant for polyamine transport based on double reciprocal Lineweaver-Burke plot analyses of four radioactive substrate concentrations (0.3-3 µM) and five inhibitor concentrations (0.01-1.0 µM) and a control. Compounds ORI 1202 and 1426 are included for comparison. See the Examples below.

A set of PAs wherein positions $R_1$ and $R_2$ of formula I are substituted by an aliphatic chain with varying degrees of unsaturation in the hydrocarbon chain are represented in FIG. 2, Series III. These compounds include those with internal geometrically cis (zusammen or Z-form) and trans (entgegen or E-form) isomers are also presented in this series.

In addition to lipophilicity effects, the disclosure incorporates considerations based on the charge character of the PA. As obvious from the above general formula II for PAs of the invention, the introduction of the $R_1X\{O\}_{n^-}$ and $R_2X\{O\}_{n^-}$ moieties reduces the number of positive charges in the analog or derivative by one. At physiological pH of 7.2 the vast majority of amine groups will be in their positively charged ammonium state. The importance of positive charges for inhibiting polyamine transport is suggested by the observation that a PA with acetamide (IA11) showed a higher $EC_{50}$ in comparison to analogous PAs wherein both $R_1X\{O\}_{n^-}$ and $R_xX\{O\}_{n^-}$ are replaced by hydrogen atoms (see IA11 versus ORI 1202 and ORI 1426 in Tables 5 and 6).

Series IV (see FIG. 2) incorporates the above considerations for both lipophilicity and positive charges by incorporating both a long hydrocarbon chain and retaining the positively charged ammonium function. The reductive amination used to produce these structures results in alkylated (instead of acylated) amines. These compounds are inferred to have great affinity for the polyamine transporter. PAs with a dimerized spermine structure, represented by structures such as IA19, showed no improvement over the original lysine-spermine conjugate.

An alternative group of PAs, based on the long-chain hydrocarbon containing carboxamides (FIG. 2, Series I), may be prepared by incorporating the lipophilic and biologically stable sulfonamide group. These PAs are shown in FIG. 2, Series II. Without being bound by theory, it may be that the addition of an additional carbonyl-like oxygen atom in the sulfonamide series increases the interactions at an amide-binding domain of polyamine transporters. An additional factor which may be playing a role is the increased lipophilicity in sulfonamides versus carboxamides. Additionally sulfonamides are known to be more biologically stable in comparison to carboxamides.

Additional ways exist to increase the lipophilicity of the substituents on the PA molecule. Alternatives with additional alkyl groups on the acyl portion of the molecule will increase the lipophilicity of this group and thus give an analog with higher activity. One additional method to increase this lipophilicity is through an attachment of an additional alkyl chain alpha to the amino group (substituent which is attached to the carbon atom attached to the nitrogen). These analogs are produced by reductive amination of the free amino precursor with one of the ketone reagents shown in Series V. An additional advantage provided by inclusion of a methyl, or other substituent, at the alpha position of the amine group is decreased rate of biological metabolism.

An additional method to increase the lipophilicity of the analogs is through the production of a tertiary amine at the proximal or distal, or both, nitrogen atoms of the molecule. These molecules, which are shown in Series VI, are produced via the reductive amination reaction using a free mono- or di-amine precursor and an excess of the carbonyl containing reagent shown in Series VI. An alternative method to produce these di-substituted tertiary amine containing molecules is the conjugate addition of the selectively protected amine precursor to an α,β-unsaturated carbonyl compound or an α,β-unsaturated nitrile compound.

The present disclosure further provides methods for the synthesis of the disclosed PAs. In general, an orthogonally protected diamine containing compound, such as, but not limited to, certain amino acids, is coupled to a primary amine group of a polyamine followed by deprotection of one or both of the protected amine groups followed optionally by further derivatization of the amine. Without limiting the scope of the disclosure, an exemplary scheme for the production of spermine based PAs according to the above formula wherein d is 4, e is 0, X is C, and either $R_1X\{O\}_{n-}$ or $R_2X\{O\}_{n-}$ is H is shown in Scheme 1, where the 4-nitrophenyl activated ester Boc-L-Lys-(Cbz)-ONP is used in combination with spermine. This scheme is for illustrative purposes only, and any other diamino containing amino acid including, but not limited to, D-lysine, L-ornithine, D-ornithine, L-2,4-diaminobutyric acid, D-2,4-diaminobutyric acid, L-2,3-diaminopropionic acid and D-2,3-diaminopropionic acid can be likewise orthogonally di-protected and coupled to spermine. Any appropriate protecting group(s) may be used in the practice of the invention, and the indication of Boc-(butoxycarbonyl-) and Cbz-(carbobenzoxy-) protecting groups are for illustrative purposes only. Other protective group strategies are known in the art (see, for example, "Protective Groups in Organic Synthesis-Third Ed. 1999, eds. T. W. Greene and P. G. M. Wuts. John Wiley and Sons, Inc. New York).

In another aspect, polyamine analogs may be prepared via the coupling of distal carboxylic acid containing amino acids with suitable protecting groups on this distal carboxylic acid (e.g. methyl or benzyl ester) such as N-$^t$Boc-Asp(OCH$_3$)—OH or N-$^t$Boc-Glu(OCH$_3$)—OH with a primary amine group of a polyamine (such as, but not limited to, spermine) followed by exhaustive protection of the remaining amino groups. After purification by silica gel chromatography the distal carboxylic acid is deprotected and reacted with long chain hydrocarbon containing amines or alcohols to give amides or esters respectively. Such polyamine analogs can be represented by the following structure.

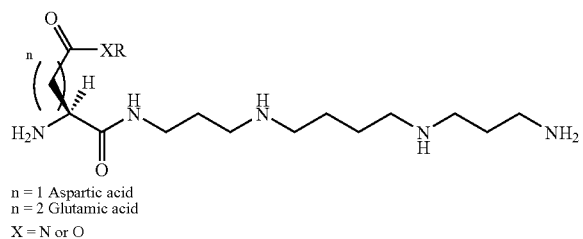

n = 1 Aspartic acid
n = 2 Glutamic acid
X = N or O wherein n can also be greater than 2, preferably up to about 10 (including 3, 4, 5, 6, 7, 8 and 9) and R is defined as provided for $R_1$ and $R_2$ in the formula II above. The alpha amino group of the distal carboxylic acid containing amino acid may also be derivatized as described above in Formula II. Such compounds may be described as "inverted" amide or ester derivatives of the compounds described in FIG. 2.

Figure 1B:
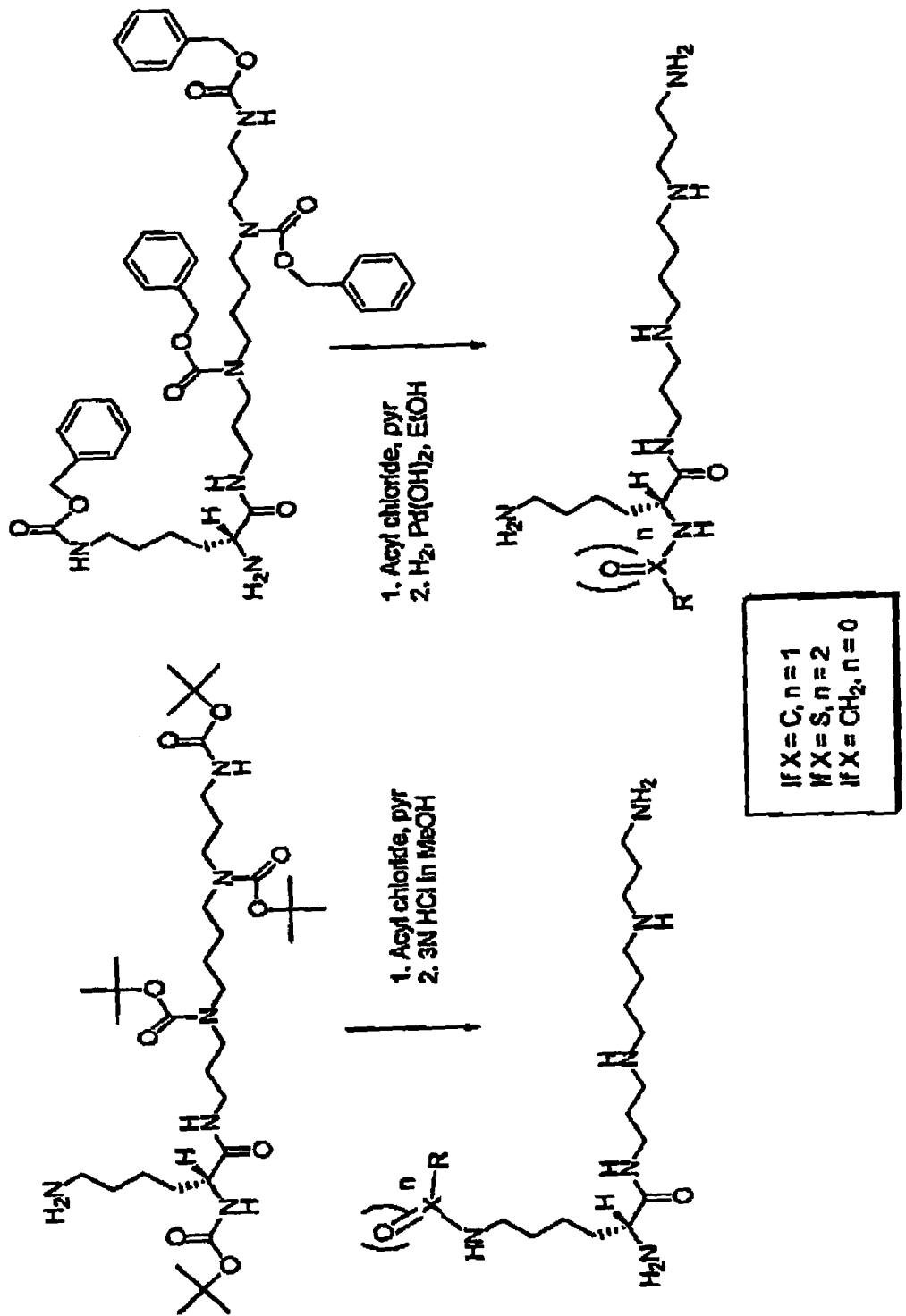

Similar hydrophobic PAs can be prepared by the use of cysteine, serine, or homo serine to link the hydrophobic and polyamine moieties indirectly. The hydrophobic PAs may also be linked via an ester linkage (like that possible via serine), a thioester linkage (like that possible via cysteine), a urea linkage (—N—CO—N—), a carbamate linkage (—O—CO—N— or —N—CO—O—), or an extended sulfonamide linkage (—NH—SO$_2$—), As shown in FIG. 1, the active ester is added to an excess of polyamine to produce a mixture of substituted and unsubstituted acyl polyamines. The remaining free amino groups of the polyamines can then be protected, such as via the $^t$Boc or Cbz carbamates, and the desired orthogonally-protected products can be isolated. Full protection of the amino groups produces a more lipophilic product mixture which facilitates purification of the desired compound. The exemplary reaction scheme in FIG. 1 results in two synthetic intermediates, one with 4 Boc and 1 Cbz carbamates and the other with 4 Cbz and 1 Boc carbamates. These intermediates allow the exposure of selectively either the distal or proximal (relative to the starting spermine polyamine) amino groups to be selectively deprotected by catalytic hydrogenation (see left branch of scheme) or acid treatment (see right branch of scheme), respectively. When viewed relative to the lysine moiety, the distal and proximal amino groups may be considered ε- or α-amino positions, respectively.

The deprotected amino groups may then be further modified via conventional amide chemistry. For example, and without limiting the disclosure, the deprotected amino groups may be acylated or alkylated with either an acyl chloride or sulfonyl chloride to produce PAs shown in FIG. 2 as Series I and II, respectively. The positions may also be carboxylic acid activated with standard peptide coupling reagents such as DCC, PyPOP or HBTU (to produce Series III PAs) or aldehydes using reductive amination conditions (to produce Series IV PAs). Additional analogs are produced by reductive amination of the free amino precursor with one of the ketone reagents shown in Series V. Series VI analogs are produced via the reductive amination reaction using a free mono- or di-amine precursor and an excess of the carbonyl containing reagent shown in Series VI portion of FIG. 2. An alternative method to produce these di-substituted tertiary amine-containing molecules is the conjugate addition of the selectively protected amine precursor to an α, β-unsaturated carbonyl compound or an α, β-unsaturated nitrile compound.

The above described synthetic schemes may be conducted in a parallel fashion to permit the simultaneous production of multiple PAs. For example, the reaction scheme shown in FIG. 1 may be started with a mixture of L- and D-forms of Boc-Lys-(Cbz)-ONP and spermine. This results in a possible 4 different amino groups (two based on each of the L- and D-forms, and two based on each of the distal and proximal amino groups) deprotection and subsequent modification. There are also two additional possible modifications where both amino groups are simultaneously deprotected for subsequent modification. This results in a total of 6 possible routes for modification.

Parallel acylation with just two acyl chlorides, such as by solution phase methods, would produce twelve different PAs. Each individual PA may then be purified and the protective groups on the polyamine portion removed before further characterization and use.

The polyamine biosynthesis inhibitors employed according to this disclosure include ODC inhibitors, spermidine synthase inhibitors, spermine synthase inhibitors, deoxyhypusine synthase inhibitors, inhibitors of ODC enzyme induction and antizyme inducing agent.

Examples of inhibitors or ornithine decarboxylase are DFMO, acetylenic putrescine, 1-aminooxy-3-aminopropane, antizyme, 2-butylputrescine, cadaverine, L-canaline, 5'-deoxy-5'-[N-methyl-N-[3-(aminooxy)ethyl]amino]adenosine, 5'-deoxy-5'[N-methyl-N-[3-(hydrazinopropyl)amino]adenosine, diaminopropane, 1,3-diamino-2-propanol, 2-difluoromethyl putrescine, difluorophenylethyl(4-aminopropylamidinohydrazone), 2,3-dimethylputrescine, N-dimethylputrescine, 2-ethylputrescine, (+ or −)-alpha-fluoromethylornithine, 2-fluoro methylputrescine, 2-hexylputrescine, 2-hydrazinoornithine, ibuprofen, D-methyl acetylenic putrescine, methylglyoxal bis(3-aminopropylamininohydrazone), 2-methylornithine, 2-methylputrescine, 2-monofluoromethyl-trans-dehydoromithine, 2-monofluoromethyl dehydroputrescine, monofluoromethylornithine, 2-monofluoromethyl putrescine, neomycin, D-ornithine, 2-pentylputrescine, p-phenylenediamine, phosphopeptide MG 25000, phosphothreonine, phosphotyrosine, 2-propylputrescine, putrescine, allo-S-adenosyl-L-methionine, S-ethylthioadenosine, methylthioadenosine, and 5'-m-ethyl-thioadenosine as discussed in Zollner H. (1993) Handbook of Enzyme Inhibitors, $2^{nd}$ Ed. Weinheim, Basel (Switzerland).

Examples of some other polyamine synthesis inhibitors are S-adenosylmethionine decarboxylase inhibitors— SAM486A (4-aminoindanon-1-(2'amidino)hydrazone dihydrochloride monohydrate), S-adenosyl-1,8-diamino-3-thiooctane, S-(5'-adenosyl)methylthio-2-aminooxyethan, S-adenosyl-3-methylthio-1-proplyamine, 5'-{[(Z)-4-amino-2-butenyl]methylamino}-5'-deoxyadenosine, 5'-amino-5'-deoxyadenosine, 5'-[(aminoiminomethyl)amino]-5']deoxyadenosine dihydrogensulphate, 1-aminooxy-3-aminopropane, [2-(aminooxy)ethyl](5'-deoxyadenosine-5'-yl)(methyl)sulphonium, 5'-[(3-aminopropyl]-amino)-5'-deoxyadenosine, 5'-[(3-aminopropyl]-nethylamino)-5'-deoxyadenosine, 9-[6(RS)-amino-5,6,7-trideoxy-beta-D-ribo-octofuranosyl]-9H-purin-6-amin, borohydride, n-butylglyoxal bis(guanylhydrazone), 9-[6(RS)-c-carboxamido-5,6,7-trideoxy-beta-D-ribo-octofuranosyl]-9H-purin-6-amine, cyanide, cyanoborohydride, S-(5'deoxy-5'adenosyl)methionylethylhydroxylamine, S-(5'deoxy-5'adenosyl) methionylthiohydroxylamine, 5'-deoxy-5'-[N-methyl-N-[2-(aminooxy)ethyl]amino]adenosine, 9-[6(S)-diamino-5,6,7,8,9-pentadeoxy-beta-D-ribo-nanofuranosyl]-9H-purin-6-amine, diethylglyoxal bis(guanylhydrazone), difluorophynylethyl (4-aminopropylamidinohydrazone), dimethyl(5'-adenosyl)sulfonium, dimethylglyoxal bis(guanylhydrazone), ethylglyoxal bis(guanylhydrazone), hydroxylamine, 4-hydroxypenenal, MDL 73811, 5'[[3-methylamino)propyl]amino]-5'-deoxyadenosine(1,1'-(methyl-ethanediylidine)dinitro)bis(3aminoguanididne), methylglyoxal bis(3-aminopropylamidinohydrazone), methylglyoxal bis(cyclohexylamidinohydrazone), methylglyoxal bis(guanylhydrazone), pentanedialdehyde bis guanylhydrazone), phenylhydrazine, propanedialdehyde bis(guanylhydrazone), semicarbazide, sodium borohydride, sodium cyanoborohydride, and spermine as discussed in Zollner H. (1993) Handbook of Enzyme Inhibitors, 2nd Ed.

The polyamine transport inhibitor and polyamine biosynthesis inhibitor can be administered together or sequentially. When administer sequentially, they are typically administered within about 12 hours of each other, more typically within about 6 hours and even more typically within about 2 hours or less of each other. For convenience, both the polyamine transport inhibitor and polyamine biosynthesis inhibitor are formulated into the same composition and more typically a topical composiiton.

The disclosure is especially concerned with inhibiting or reducing hair growth and treating a patient suffering from auto-immune disease. Examples of autoimmune diseases are clinical autoimmune diseases including host versus graft disease, graft versus host disease and lupus; and other autoimmune diseases including cutaneous lupus, multiple sclerosis, atopic dermatitis, rheumatoid arthritis, scleroderma, inflammatory bowel disease, transplantation rejection and diabetes.

For topical application, the polyamine transport inhibitor and polyamine biosynthesis inhibitor may be incorporated into topically applied vehicles such as a salve or ointment. The carrier for the active ingredient may be either in sprayable or nonsprayable form. Non-sprayable forms can be semi-solid or solid forms comprising a carrier indigenous to topical application and having a dynamic viscosity preferably greater than that of water. Suitable formulations include, but are not limited to, solution, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams; gels; as well as petroleum jelly and the like.

Also suitable for topical application are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or anti-oxidants in addition to the compounds of the invention.

For the typical topical applications, especially for humans, it is typical to administer an effective amount of the polyamine transport inhibitor and polyamine biosynthesis inhibitor to a target area, e.g., skin surface, mucous membrane, eyes, etc. The amounts will generally range from about 0.001 mg to about 1 g per application, depending upon the area to be treated, the severity of the symptoms, and the nature of the topical vehicle employed. A particular example contains about 1% by weight of the polyamine transport inhibitor and about 1% by weight of the polyamine biosynthesis inhibitor. The amount of the polyamine transport inhibitor employed is effective in inhibiting or reducing polyamine transport and the amount of polyamine biosynthesis inhibitor employed is effective for inhibiting or reducing polyamine biosynthesis.

In addition, the polyamine transport inhibitor and polyamine biosynthesis inhibitor may be incorporated into convenient dosage forms, such as capsules, impregnated wafers, tablets or injectable preparations. Solid or liquid pharmaceutically acceptable carriers may also be employed. Pharmaceutical compositions designed for timed or delayed release may also be formulated.

Optionally, the compositions contain anti-oxidants, surfactants and/or glycerides. Examples of anti-oxidants include, but not limited to, BHT, vitamin E and/or C. Examples of glycerides include, but are not limited to, one or more selected from acetylated or unsubstituted monoglycerides; medium chain triglycerides, such as those found in oils; and caprylocaproyl macrogol-8 glycerides.

The compositions can also be administered systemically, e.g., by injection or oral administration. When used, injection may be by any known route, preferably intravenous, subcutaneous, intramuscular, intracranial or intraperitoneal. Injectables can be prepared in conventional forms, either as solutions or suspensions, solid forms suitable for solution or suspension in liquid prior to injection, or as emulsions.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, liquid containing capsule, sterile injectable liquid (e.g., a solution), such as an ampule, or an aqueous or nonaqueous liquid suspension. A summary of such pharmaceutical compositions may be found, for example, in *Remington's Pharmaceutical Sciences*, Mack Publishing Company, Easton Pa. (Gennaro $18^{th}$ ed. 1990).

The pharmaceutical preparations are made following conventional techniques of pharmaceutical chemistry involving such steps as mixing, granulating and compressing, when necessary for tablet forms, or mixing, filling and dissolving the ingredients, as appropriate, to give the desired products for oral or parenteral administration. Other preparations for transdermal, intravaginal, intranasal, intrabronchial, intracranial, intraocular, intraaural and rectal administration may also be prepared. The pharmaceutical compositions may also contain minor amounts of nontoxic auxiliary substances such as wetting or emulsifying agents, pH buffering agents and so forth.

The pharmaceutical composition may be administered topically as mentioned above or trandermally, e.g., as an ointment, cream or gel; orally; rectally; e.g., as a suppository, parenterally, by injection or continuously by infusion; intravaginally; intranasally; intrabronchially; intracranially; intraaurally; or intraocularly.

The pharmaceutical compositions employed may also comprise one or more other medicaments such as anti-infectives including antibacterial, anti-fungal, anti-parasitic, antiviral, and anti-coccidial agents.

Typical single dosages of the polyamine transport inhibitor and polyamine biosynthesis inhibitor are between about 1 ng and about 10 g/kg body weight. The dose is more typically between about 0.01 mg and about 1 g/kg body wt. and, even more typically, between about 0.1 mg and about 100 mg/kg body wt. For the topical administration, dosages in the range of about 0.01-20% concentration of the compound, more particularly 1-5%, are suggested. Especially the foregoing ranges are, however, suggestive, as the number of variables in regard to an individual treatment regime is large, and considerable excursions from these recommended values are expected and may be routinely made by those skilled in the art.

Effective amounts of doses can be determined using recognized in vitro systems or in vivo animal models for the particular disease or condition.

The following non-limiting examples are presented to further illustrate the present disclosure:

EXAMPLE 1

Chemical Synthesis of Polyamine Agents (PAs)

PAs analogs were synthesized in a parallel fashion starting from the orthogonally protected diamino containing amino acid starting materials. The use of the 4-nitrophenyl activated ester L-Boc-Lys-(Cbz)-ONP in FIG. 1 provides an exemplary illustration of the synthetic process. The active ester is added dropwise to a solution of 1.5 equivalents of polyamine in methanol to give a statistical mixture of unsubstituted, mono-substituted and di-substituted acyl polyamines. Following evaporation of the solvent, the remaining free amino groups in the polyamine moiety are protected either as their $^t$Boc or Cbz carbamates. Standard workup results in a completely protected crude product mixture. The desired orthogonally-protected product is isolated in pure form by silica gel chromatography suing standard organic solvents. This purification process is based on separation of polyamine molecules with the remaining amino groups being fully protected, which provides a much more lipophilic product mixture that greatly facilitates the purification process. Thus the exemplary intermediates containing either 4 Boc groups or 4Cbz groups in addition to the acyl functionality remained lipophilic enough to purify using standard solvents including a one to one mixture of ethyl acetate and hexanes containing various proportions of methanol (0 to 10%).

As shown in FIG. 1, the approach provides two synthetic intermediates, one with 4 Boc and 1 Cbz carbamates and the other with 4 Cbz and 1 Boc carbamates. These intermediates allow the exposure of only one amino group, either the proximal ($\alpha$-) or distal ($\epsilon$-), in a selective manner. It is also possible to modify this approach such that both amino groups are exposed for further modification. The selective deprotection of either the proximal ($\alpha$-) or distal ($\epsilon$-) amino group as shown in FIG. 1 may occur via catalytic hydrogenation or acid treatment, respectively. The exposed amino groups were then acylated or alkylated with either an acyl chloride or sulfonyl chloride to produce Series I and II (see FIG. 2) type PAs, respectively. The exposed amino groups may also be carboxylic acid activated with standard peptide coupling reagents such as DCC, PyPOP or HBTU (to produces Series III type PAs) or aldehydes under reductive amination conditions (to produce Series IV type PAs). Additional analogs are produced by reductive amination of the free amino precursor with one of the ketone reagents shown in Series V. Series VI analogs are produced via the reductive amination reaction using a free mono- or di-amine precursor and an excess of the carbonyl reagent that are shown in the Series VI chart. An alternative method to produce these di-substituted tertiary amine-containing molecules is the conjugate addition of the selectively protected amine precursor to an $\alpha$, $\beta$-unsaturated carbonyl compound or an $\alpha$, $\beta$-unsaturated nitrile compound.

Deprotections of isolated PAs using standard conditions gave the desired products in pure form. The PAs were characterized by thin layer chromatography (TLC) analysis (using $^i$PrOH/HOAc/pyr/H$_2$O, 4:1:1:2); high performance liquid chromatography (HPLC) analysis (dansylation followed by HPLC using fluorescent detection); liquid chromatography-mass spectroscopy (LC-MS) by electrospray ionization; and $^1$H and $^{13}$C NMR analysis. All PAs were estimated to be 90 to 98% pure following synthesis.

EXAMPLE II

Cell Culture and Reagents

All cell lines were obtained from ATCC (Manassas, Va.) and cultured in the recommended media, serum, and CO$_2$ concentration. Medias were obtained from Mediatech, Inc. (Hemdon, Va.) and serums from Gibco BRL (Gaithersburg, Md.). 50 U/ml penicillin, 50 μg/ml streptomycin and 2 mM L-glutamine (all from Bio Whittaker, Walkersville, Md.) were included in all cultures. DFMO was obtained from Marion Merrell Dow (Cinncinati, Ohio). When cells were cultured with polyamines or ORI compounds, 1 mM aminoguanidine (AG; Sigma) was included to inhibit serum amine oxidase activity. IC$_{50}$ refers to the concentration of PA that results in 50% of maximum cell growth inhibition in the presence of PA alone.

EXAMPLE III

Polyamine Transport and Ki Assays

[2,9-$^3$H]spermidine (SPD) from DuPont NEN, Boston, Mass. was added alone or simultaneously with PAs to 24-well plates containing MDA-MB-231 cells in log growth. The cells were incubated in 37° C. for 15 min to determine initial rate polyamine uptake. The cells were then washed three times with cold PBS, lysed with 0.1% SDS, and the amount of polyamine incorporation into the cells was determined by scintillation counting of cell lysates. To determine of K$_i$, four radioactive substrate concentrations (0.3-3 μM) and five inhibitor concentrations (0.01-1.0 µM) and a control were tested. The $K_i$ values were determined using double reciprocal Lineweaver-Burke plot analyses. $K_i$ values were determined from linear equations derived from graphing the slopes of Lineweaver-Burke plots vs. inhibitor concentration, with $K_i$=y-intercept/slope.

EXAMPLE IV

Growth Inhibition Assay

Cells were plated in 96-well plates such that they would be in log growth for the duration of the assay. The day after plating, PAs were added to the cells, and growth, if any, permitted to continue for six days in the presence of 1 mM AG and 0.5 µM SPD to insure that any growth inhibition was not the result of depletion of external polyamines in the media. At the end of the six days, cell growth was measured by MTS/PMS dye assay (Cell Titer 96 Aqueous Non-Radioactive Cell Proliferation Assay; Promega, Madison, Wis.). $EC_{50}$ represents the concentrations of PA that resulted in 50% of maximum growth inhibition achievable in the presence of both DFMO (5 mM in all cell lines except MDA) and PA (at different concentrations depending in part on the cell line used) compared to controls. $IC_{50}$ represents the concentration of PA that resulted in 50% maximum growth inhibition when used alone. Results are shown in Tables 5 and 6 above.

EXAMPLE V

HPLC Analysis of Dansylated Derivative

Sample handling for Polyamine Analysis (see Kabra et al., Solid-Phase Extraction and Determination of Dansyl Derivatives of Unconjugated and Acetylated Polyamines by Reverse-Phase Liquid Chromatography: Improved Separation Systems for Polyamines in Cerebrospinal Fluid, Urine and Tissue. Journal of Chromatography 380 (1986) 19-32)

Plasma samples (from blood)—remove 125-150 µl sample (optimally) into a microfuge tube and mix 1:1 with 0.4M perchloric acid. Vortex and spin down sample at 13000 rpm for 10 minutes in 5° C. centrifuge. Remove 200 µl supernatant for dansylation as described in dansylation protocol. Plasma samples as small as 25 µl may be analyzed (for this and the following discussion, any sample that does not yield 200 µl supernatant for dansylation may have its volume increased to 200 µl with perchloric acid for the dansylation protocol).

Cell Culture Samples

Media—remove 1.5 ml into 1.7 ml microfuge tube and spin at 3000 rpm for 5 minutes in 5° C. centrifuge. Remove 300 µ supernatant and mix 1:1 with cold 0.4M perchloric acid. Vortex and spin down sample at 13000 rpm for 10 minutes in 5° C. centrifuge. Remove 200 µl supernatant for dansylation as described in dansylation protocol.

Cells—Trypsinize as usual and spin in 15 ml tube 6 min at 4° at 1500 rpm. Pour off supernatant and resuspend pellet in 1.5 ml 1×PBS. Transfer to large microfuge tube. Spin at 3000 rpm at 4° for 5 minutes. Remove supernatant. Resuspend pellet in 1.0 ml 1×PBS. Remove 20 µl for counting and spin @ 3000 rpm @4° for 5 minutes. Remove supernatant. To the dry pellet, add 200 µl 0.4M perchloric acid per $10^6$ cells. Pipette up and down to mix. Vortex and spin down sample at 13000 rpm for 10 minutes in 5° C. centrifuge. Remove 200 µl supernatant for dansylation as described in dansylation protocol. Remainder of supernatant can be stored at −70° C.

Tissues—Keep samples on ice during preparation. Cut an approximately 100 mg piece from tissue sample and place into 15 ml conical tube. Add 1.2M perchloric acid in a 20:1 vol/weight ratio (i.e. 2 ml/100 mg). Homogenize tissue using a tissue grinder. Vortex sample and remove 1 ml into a microfuge tube. Spin at 13000 rpm for 10 minutes in 5° C. centrifuge. Remove 200 µl supernatant for dansylation as described in dansylation protocol.

Dansylation Protocol for Polyamine Analysis

200 µl sample Perchloric acid

10 µl Internal Standard (IS) (1,7-diaminoheptane, 100 µM stock); p use 20 µl for 25 min and

1483 HPLC

120 µk saturated sodium carbonate solution (360 µl is used for tissue samples)

400 µl dansyl chloride solution (made fresh, 10 mg/ml in acetone)

Add all ingredients to a 4 ml screw cap glass vial and vortex for 30 seconds. Float vials in 70° C. water bath for 10 minutes. Remove and allow cooling to room temp in dark, as samples are light sensitive. Proceed to sample prep protocol once samples have cooled.

Sample Prep Protocol

Altech C-18 maxi-prep cartridges are used, one for each sample dansylated, to clean any interfering reactions from the samples. This process also places the samples in methanol for application to the HPLC system.

Each cartridge is placed on a vacuum manifold and washed once with 3 ml MeOH followed by 3 ml $H_2O$. Samples are then removed by 1 ml syringe from the glass vials and applied to the Alltech cartridges. Each cartridge is then washed with 10 ml $H_2O$ and dried 2× with 30 cc syringe of air.

All steps to this point are allowed discarded. The cartridges are placed with a tube rack with labeled 1.7 ml microfuge tubes for elution. Samples are eluted with 1 ml MeOH into the microfuge tubes. Samples are now ready for injection onto HPLC or can be stored at −70° C. for up to several months if necessary.

The solvents used in the above are as follows:

Solvent A: HPLC grade Acetonitrile

Solvent B: 10 mM Na acetate pH 4.5/10% acetonitrile (8.9L $H_2O$, 1 L Acetonitrile, 100 ml 1M Na acetate pH 4.5, mix well, filter and store at room temp).

Sample Injection: loop overfill is achieved by injecting 100 µl onto 20 µl loop. Samples are kept at 4° C. until injection by a water cooled storage rack on the 231XL auto injector.

| Gradient: | 40 minute PA analysis: | | |
|---|---|---|---|
| | time | % A | % B |
| | 0 | 48 | 52 |
| | 25 | 90 | 10 |
| | 30 | 100 | 0 |
| | 35 | 48 | 52 |
| | 40 | 48 | 52 |

Flow rate is 3 ml/minute

Solutions and Sources are as follows:

Internal Standard: 1,7-Diaminoheptane (Sigma D-3266)

Made up 20 mM in $H_2O$ and stored at −70° C. Diluted to 100 µM working stock in $H_2O$ and also stored at −70° C.

Perchloric acid: 70% ACS reagent (Aldrich 244252)
 For 0.4M, mix 3.4 ml in a total of 100 ml $H_2O$. Store at room temp.
 For 1.2M, mix 10.2 ml in a total of 100 ml $H_2O$. Store at room temp.
Sodium carbonate: anhydrous (Acros 42428-5000)
 Make a saturated solution in $H_2O$.
Sodium acetate: anhydrous (Sigma S-2889)
 Make up 1M in $H_2O$, then pH to 4.5 with glacial acetic acid. Filter and store at room temp.
Dansyl chloride: 95% (Sigma D-2625)
Acetonitrile: HPLC grade (Fisher A998-4)
Methanol: HPLC grade (Fisher A452-4)
Acetone: HPLC grade (Fisher A949-1)
Glacial acetic acid: ACS reagent (Fisher A38212)

TABLE 7

Effectiveness of agents in animal hair growth inhibition assay.[a]

| Compound | Biosynthesis inhibitor[b] | % HGI[c] | $EC_{50}$ value[d] (μM) |
|---|---|---|---|
| None | DFMO | 28% | n.a. |
| None | Vaniqua ™ (13.9% DFMO) | 65% | n.a. |

TABLE 7-continued

Effectiveness of agents in animal hair growth inhibition assay.[a]

| Compound | Biosynthesis inhibitor[b] | % HGI[c] | $EC_{50}$ value[d] (μM) |
|---|---|---|---|
| Agmatine (2%) | (antizyme inducer) | 30% | n.a. |
| MQT 1 | DFMO | 31% | 3.0 |
| MQT 2 | DFMO | 97% | 0.044 |
| MQT 3 | DFMO | 93% | 0.78 |
| MQT 3 | BHT 0.5% | 68% | " |
| MQT 4 | DFMO | 63% | 1.6 |
| MQT 4 | None | 66% | " |
| MQT 5 | DFMO | 47% | 2.2 |
| MQT 6 | DFMO | 79% | 0.38 |
| MQT 7 | (antizyme inducer) | 94% | n.a. |
| MQT 8 | (antizyme inducer) | 53% | n.a. |

[a]Conditions: Compounds dissolved in 70% ethanol as their per-HCl salts, pH adjusted to 7.0 and applied once a day for 18 days.
[b]Biosynthesis inhibitor at 2% in the above solution when DFMO was used. No additional biosynthesis inhibitor is needed for the antizyme inducers agmatine, MQT 7 and MQT 8.
[c]Ten mice in group and hair shaven before assay. Hair regrowth was scored from 0 to 5 and averaged over group. Hair re-grew following stopping of treatment.
[d]$EC_{50}$ value determined as previously disclosed in Weeks R S, Vanderwerf S M, Carison C L, Burns M R, O'Day C L, Cai F, Devens B H, Webb H K. Novel lysine-spermine conjugate inhibits polyamine transport and inhibits cell growth when given with DFMO. Exp Cell Res. 2000, 261(1), 293-302.

TABLE 8

Compound structures.

| Analog | Structure | Formula | MW |
|---|---|---|---|
| MQT 1 | 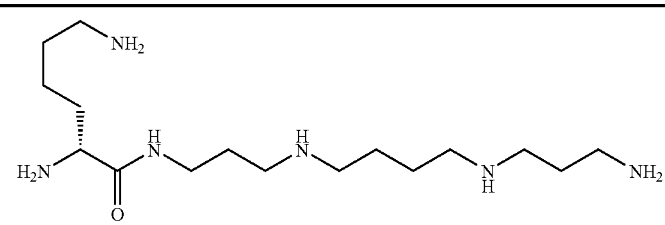 | $C_{16}H_{38}N_6O$ | 330.5 |
| MQT 2 | 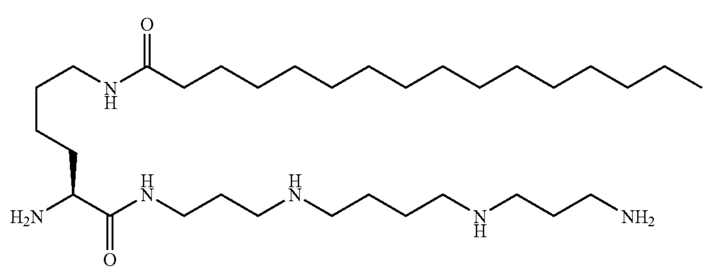 | $C_{32}H_{68}N_6O_2$ | 568.9 |
| MQT 3 | 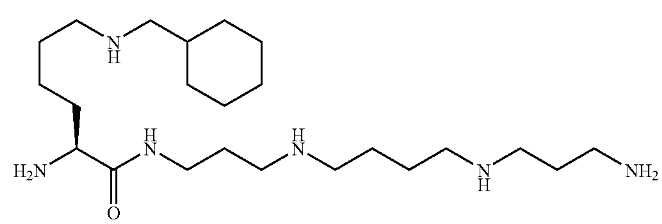 | $C_{23}H_{50}N_6O$ | 426.7 |

TABLE 8-continued

Compound structures.

| Analog | Structure | Formula | MW |
|---|---|---|---|
| MQT 4 | 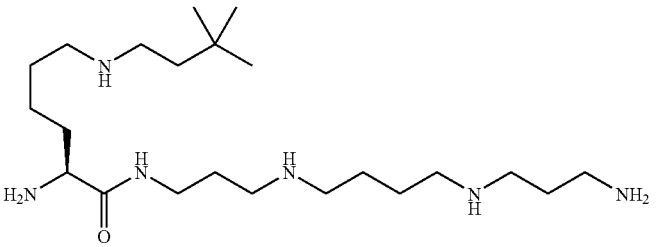 | $C_{22}H_{50}N_6O$ | 414.7 |
| MQT 5 | 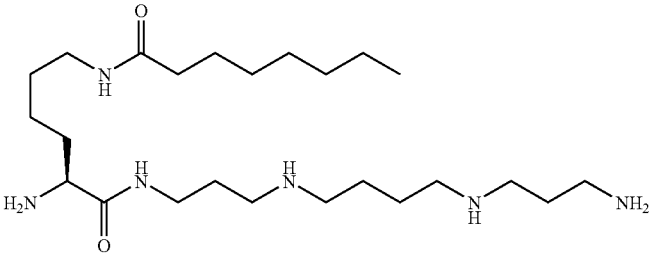 | $C_{24}H_{52}N_6O_2$ | 456.7 |
| MQT 6 | 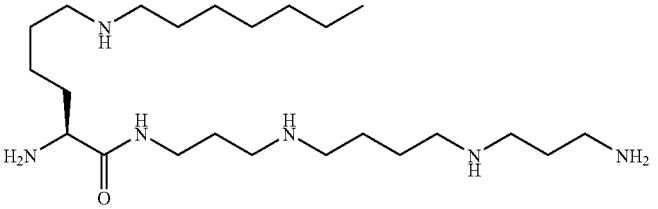 | $C_{23}H_{52}N_6O$ | 428.7 |
| MQT 7 | 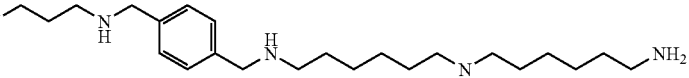 | $C_{23}H_{45}N_5$ | 391.6 |
| MQT 8 | 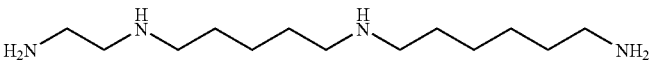 | $C_{13}H_{32}N_4$ | 244.4 |

All references cited herein, including patents, patent applications, and publications, are hereby incorporated by reference in their entireties, whether previously specifically incorporated or not. As used herein, the terms "a", "an", and "any" are each intended to include both the singular and plural forms.

It will be appreciated by those skilled in the art that the disclosure can be performed within a wide range of equivalent parameters, concentrations, and conditions without departing from the spirit and scope of this disclosure and without undue experimentation. While this disclosure has been described in connection with specific embodiments thereof, it will be understood that it is capable of further modifications. This application is intended to cover any variations, uses, or adaptations, in general, the principles of and including such departures from the present disclosure as come within known or customary practice within the art to which the disclosure pertains and as may be applied to the essential features hereinbefore set forth.

What is claimed is:

1. A method for inhibiting or reducing hair growth, which comprises administering to a patient in need thereof a polyamine transport inhibitor, wherein the polyamine transport inhibitor is selected from the compounds

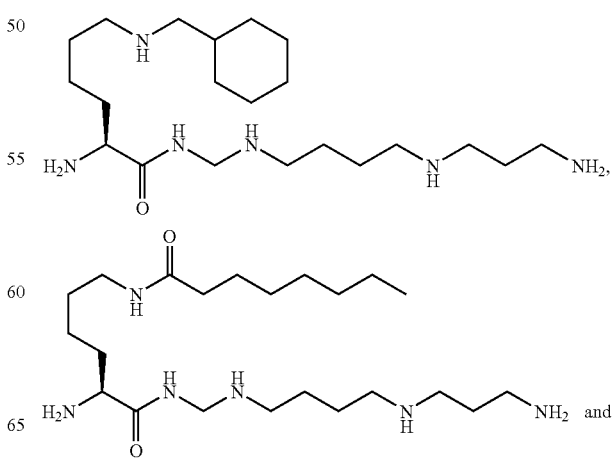

-continued

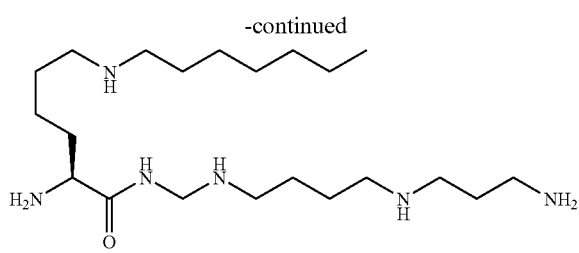

or pharmaceutically acceptable salts thereof or prodrugs thereof, and a polyamine biosynthesis inhibitor.

2. The method of claim 1 wherein the polyamine biosynthesis inhibitor is an ornithine decarboxylate (ODC) inhibitor.

3. The method of claim 1 wherein the biosynthesis inhibitor is a spermidine synthase inhibitor.

4. The method of claim 1 wherein the biosynthesis inhibitor is a spermine synthase inhibitor.

5. The method of claim 1 wherein the biosynthesis inhibitor is a deoxyhypusine synthase inhibitor.

6. The method of claim 1 wherein the biosynthesis inhibitor is an inhibitor of ODC enzyme induction.

7. The method of claim 1 wherein the biosynthesis inhibitor is an antizyme inducing agent.

8. The method of claim 1 wherein the polyamine transport inhibitor and polyamine biosynthesis inhibitor are administered simultaneously.

9. The method of claim 1 wherein the polyamine transport inhibitor and polyamine biosynthesis inhibitor are administered sequentially.

* * * * *